United States Patent
Treiber et al.

(12)

(10) Patent No.: US 6,214,822 B1
(45) Date of Patent: Apr. 10, 2001

(54) SUBSTITUTED AZA AND DIAZACYCLOHEPTANE AND CYCLOOCTANE COMPOUNDS AND THEIR USE

(75) Inventors: Hans-Jörg Treiber, Brühl; Stefan Blank, Ludwigshafen; Dorothea Starck, Ludwigshafen; Liliane Unger, Ludwigshafen; Hans-Jürgen Teschendorf, Dudenhofen; Karsten Wicke, Altrip, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/101,265
(22) PCT Filed: Jan. 10, 1997
(86) PCT No.: PCT/EP97/00106
  § 371 Date: Jul. 6, 1998
  § 102(e) Date: Jul. 6, 1998
(87) PCT Pub. No.: WO97/25324
  PCT Pub. Date: Jul. 17, 1997

(30) Foreign Application Priority Data

Jan. 12, 1996 (DE) ............................................. 196 00 934

(51) Int. Cl.$^7$ .................... A61K 31/5513; C07D 243/06
(52) U.S. Cl. .......................... 514/218; 540/484; 540/553
(58) Field of Search ................................... 540/484, 553; 514/183, 218

(56) References Cited

U.S. PATENT DOCUMENTS

| | | | |
|---|---|---|---|
| 5,034,390 | 7/1991 | Olsson et al. | 514/252 |
| 5,407,823 | 4/1995 | Sokoloff et al. | 435/252 |
| 5,872,119 | 2/1999 | Wermuth et al. | 514/254 |

FOREIGN PATENT DOCUMENTS

| | | |
|---|---|---|
| 628766 | 2/1963 | (BE) . |
| 2195241 | 2/1996 | (CA) . |
| 2195242 | 2/1996 | (CA) . |
| 2195243 | 2/1996 | (CA) . |
| 2915240 | 2/1996 | (CA) . |
| 2258561 | 6/1973 | (DE) . |
| 4425143 | 7/1994 | (DE) . |
| 4425144 | 7/1994 | (DE) . |
| 4425145 | 7/1994 | (DE) . |
| 4425146 | 7/1994 | (DE) . |
| 369627 | 5/1990 | (EP) . |
| 452107 | 10/1991 | (EP) . |
| 454489 | 10/1991 | (EP) . |
| 4134070 | 5/1992 | (JP) . |
| 92/07937 | 5/1992 | (WO) . |

OTHER PUBLICATIONS

*Chem. Abst.*, vol. 78, AN 124619p, 1973 (abstract of DE 21 39 082).

Murray et al., *Biorg. & Med. Chem. Letters*, vol. 5, No. 3, pp. 219–222, 1995.

Schwartz et al., *Novel Antipsychotic Drugs*, 1992, pp. 135–144.

Sokoloff et al., *Arzneim. Forsch./Drug Res.*, vol. 42, No. 1, 1992, pp. 224–230.

Sokoloff et al., *Nature*, vol. 347, 1990, pp. 146–151.

Van Der Brink et al., *Handb. Exp. Pharm.*, 1978, pp. 333–367.

Shiozawa et al., *Chem. Pharm. Bull*, 1984, 32(2), pp. 553–563.

Primary Examiner—Mukund J. Shah
Assistant Examiner—Pavanaram K Sripada
(74) Attorney, Agent, or Firm—Keil & Weinkauf

(57) ABSTRACT

Aza- and diazacyclohexane and -cyclooctane compounds of the following formula:

$$Ar^1\text{—}A\text{—}B\text{—}Ar^2 \qquad (I)$$

where $Ar^1$, A, B and $Ar^2$ have the meanings stated in the description have a high affinity for the dopamine $D_3$ receptor and can therefore be used to treat disorders which respond to dopamine $D_3$ ligands.

12 Claims, No Drawings

SUBSTITUTED AZA AND DIAZACYCLOHEPTANE AND CYCLOOCTANE COMPOUNDS AND THEIR USE

This application is a 371 of PT/EP97/00106 filed Jan. 10, 1997.

The invention relates to substituted aza- and diazacycloheptane and -cyclooctane compounds and to the use of such compounds. Said compounds have valuable therapeutic properties and can be used in particular for treating disorders which respond to dopamine $D_3$ ligands.

Compounds of the type under discussion here and having physiological activity have in some cases been disclosed. Thus, DE 21 39 082 and DE 22 58 561 describe pyrimidine derivatives and pyrimidone derivatives with basic substituents as drugs for lowering blood pressure. These pyrimidine and pyrimidone derivatives have the formulae:

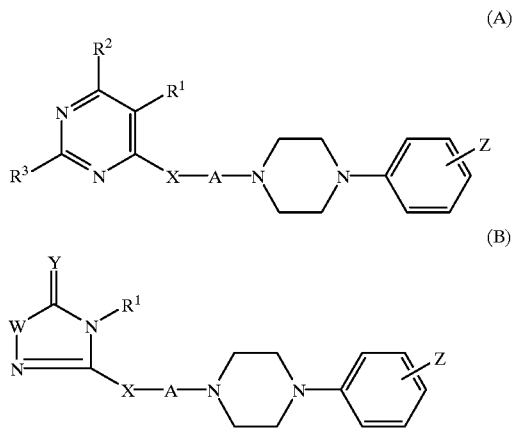

where in (A) X is, inter alia, a sulfur atom, A is a $C_1$–$C_6$-alkylene group, and $R^1$, $R^2$, $R^3$ and Z are various substituents. In (B), X and Y are an oxygen or sulfur atom, A is a $C_2$–$C_6$-alkylene group, W is a vinylene group and R and Z are various substituents.

EP-A-361271 describes pyridyl and pyrimidyl derivatives of the formula:

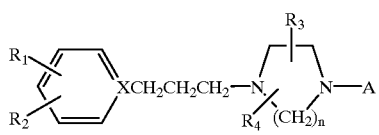

where $R_1$ is halogen or hydrogen, and $R_2$ is halogen; X is oxygen, sulfur or methylene; $R_3$ and $R_4$, which are identical or different, are hydrogen or lower alkyl; n is 2 or 3; A is a 2-pyrimidyl group or a 2- or 3-pyridyl group, it being possible for these groups to be substituted.

These compounds can be used to treat mental disturbances.

EP-A-454498 describes compounds of the formula

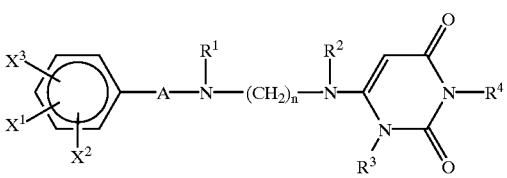

where A is, inter alia, —$(CH_2)_m$— or —B—$(CH_2)_k$—, where B is O, S, an unsubstituted or substituted amino group, —CONH— or —COO—, $R^1$ and $R^2$ can, inter alia, together form an alkylene chain, $R^3$ and $R^4$ are a hydrogen atom or a lower alkyl group, and $X^1$, $X^2$ and $X^3$ are various substituents. These compounds can be used to treat cardiac arrhythmias.

EP-A-452107 and EP-A-369627 describe structurally similar compounds which can likewise be used for treating cardiac arrhythmias.

In addition, BE-A-628 766 describes compounds of the formula

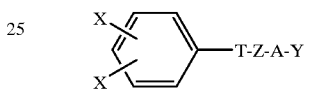

where X is a halogen atom or a lower alkyl radical, T is piperazine, methylpiperazine, homopiperazine or methylhomopiperazine; Z is alkylene or alkenylene; A is O or S; and Y is a naphthyl, halonaphthyl or an unsubstituted or mono- to trisubstituted phenyl radical. These compounds can be used to treat schistosomiasis.

Neurones obtain their information inter alia via G-protein-coupled receptors. There are numerous substances which exert their effect via these receptors. One of these is dopamine.

Confirmed information on the presence of dopamine and its physiological function as neurotransmitter is available. Cells responding to dopamine are connected with the etiology of schizophrenia and Parkinson's disease. These and other diseases are treated with drugs which interact with dopamine receptors.

Up to 1990, two subtypes of dopamine receptors had been clearly defined pharmacologically, mainly the $D_1$ and $D_2$ receptors.

More recently, a third subtype has been found, namely the $D_3$ receptor, which appears to mediate some of the effects of antipsychotics (J. C. Schwartz et al., The Dopamine $D_3$ Receptor as a Target for Antipsychotics, in Novel Antipsychotic Drugs, H. Y. Meltzer, Ed. Raven Press, New York 1992, pages 135–144).

$D_3$ receptors are mainly expressed in the limbic system. It is therefore assumed that a selective $D_3$ antagonist is likely to have the antipsychotic properties of the $D_2$ antagonists but not their neurological side effects (P. Sokoloff et al., Localization and Function of the $D_3$ Dopamine Receptor, *Arzneim. Forsch./Drug Res.* 42(1), 224 (1992); P. Sokoloff et al. Molecular Cloning and Characterization of a Novel Dopamine Receptor ($D_3$) as a Target for Neuroleptics, *Nature*, 347, 146 (1990)).

P. J. Murray et al., Bioorganic & Medicinal Chemistry Letters, Vol. 5, No. 3, 219–222 (1995), have described arylpiperazines of the formula

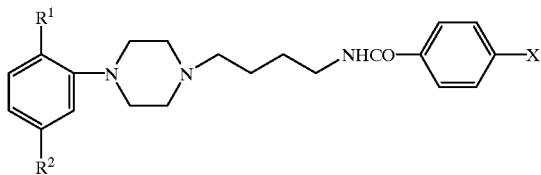

where $R^1$ and $R^2$ are H or $CH_3O$, and X is Br, 4-acetylphenyl, 4-methylsulfonylphenyl or 4-aminophenyl, with higher affinity and selectivity for the dopamine $D_3$ receptor.

We have now found, surprisingly, that certain aza- and diazacycloheptane and -cyclooctane compounds have a high affinity for the dopamine $D_3$ receptor and a low affinity for the $D_2$ receptor. They are thus selective $D_3$ ligands.

The present invention therefore relates to the compounds of the general formula I:

$$Ar^1-A-B-Ar^2 \qquad (I)$$

where
$Ar^1$ is

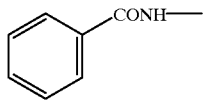

or a 5- or 6-membered heteroaromatic ring with 1, 2 or 3 heteroatoms which are selected, independently of one another, from O, N and S, where $Ar^1$ may have 1, 2, 3 or 4 substituents which are selected, independently of one another, from $OR^1$, alkyl which is unsubstituted or substituted by OH, $OC_1-C_8$-alkyl or halogen, or $C_2-C_6$-alkenyl, $C_2-C_6$-alkynyl, cycloalkyl, halogen, CN, $CO_2R^1$, $NO_2$, $NR^1R^2$, $SR^1$, $CF_3$, $CHF_2$, phenyl which is unsubstituted or substituted by $C_1-C_6$-alkyl, $OC_1-C_6$-alkyl, acyl, phenyl, amino, nitro, cyano or halogen, or phenoxy which is unsubstituted or substituted by $C_1-C_6$-alkyl, $OC_1-C_6$-alkyl or halogen, or $C_1-C_6$-alkanoyl or benzoyl;

$R^1$ is H, alkyl which is unsubstituted or substituted by OH, $OC_1-C_6$-alkyl, phenyl or halogen;

$R^2$ has the meanings stated for $R^1$ or is $COR^1$ or $CO_2R^1$;

A is a $C_3-C_{15}$-alkylene group when $Ar^1$ is $C_6H_5CONH$, or, when $Ar^1$ is a 5- or 6-membered heteroaromatic ring, is a $C_4-C_{15}$-alkylene group or a $C_3-C_{15}$-alkylene group which comprises at least one group Z which is selected from O, S, $NR^1$, a double and a triple bond, where $R^1$ is as defined above, B is a 7- or 8-membered saturated ring with one or two nitrogen heteroatoms, the nitrogen heteroatoms being located in the 1,4 or 1,5 position and the ring being bonded in position 1 to the radical A and in position 4 or 5 to the radical $Ar^2$, and it additionally being possible for the ring to have a double bond in position 3 or 4 in the monoaza ring and in position 6 in the 1,4-diaza ring;

$Ar^2$ is phenyl, pyridyl, pyrimidinyl or triazinyl, it being possible for $Ar^2$ to have 1, 2, 3 or 4 substituents which are selected, independently of one another, from $OR^1$, alkyl, $C_2-C_6$-alkenyl, $C_2-C_6$-alkynyl, alkoxyalkyl, haloalkyl, halogen, CN, $CO_2R^1$, $NO_2$, $SO_2R^1$, $NR^1R^2$, $SO_2NR^1R^2$, $SR^1$, a 5- or 6-membered carbocyclic, aromatic or non-aromatic ring and a 5- or 6-membered heterocyclic aromatic or non-aromatic ring with 1 to 3 heteroatoms which are selected from O, S and N, the carbocyclic or heterocyclic ring being unsubstituted or substituted by $C_1-C_8$-alkyl, phenyl, phenoxy, halogen, $OC_1-C_8$-alkyl, OH, $NO_2$ or $CF_3$, where $R^1$ and $R^2$ have the abovementioned meanings, and $Ar^2$ may also be fused to a carbocyclic ring of the type defined above, and where $Ar^2$ cannot be a pyrimidinyl radical substituted by 2 hydroxyl groups, and the salts thereof with physiologically tolerated acids.

The compounds according to the invention are selective dopamine $D_3$ receptor ligands which intervene regioselectively in the limbic system and, because of their low affinity for the $D_2$ receptor, have fewer side effects than classical neuroleptics, which are $D_2$ receptor antagonists. The compounds can therefore be used to treat disorders which respond to dopamine $D_3$ receptor antagonists or agonists, eg. for treating disorders of the central nervous system, in particular schizophrenia, depression, neuroses and psychoses.

For the purpose of the present invention, the following terms have the meanings indicated thereafter:

alkyl (also in radicals such as alkoxy, alkylamino etc.) is a straight-chain or branched alkyl group with 1 to 8 carbon atoms, preferably 1 to 6 carbon atoms and, in particular, 1 to 4 carbon atoms. The alkyl group may have one or more substituents which are selected, independently of one another, from OH and $OC_1-C_8$-alkyl.

Examples of an alkyl group are methyl, ethyl, n-propyl, i-propyl, n-butyl, isobutyl, t-butyl, etc.

Cycloalkyl is in particular $C_3-C_6$-cycloalkyl, such as cyclopropyl, cyclobutyl, cyclopentyl and cyclohexyl.

Alkylene is a straight-chain or branched radical with, preferably, 4 to 15 carbon atoms, particularly preferably 4 to 10 carbon atoms, or with 3 to 15, in particular 3 to 10, carbon atoms when the alkylene group comprises one of said groups.

The alkylene groups may comprise at least one of the groups Z indicated above in the definition of A. This may, just like the said double or triple bond, be located anywhere in the alkylene chain or in position 1 or 2 of group A (seen from the $Ar^1$ radical). A is particularly preferably compounds according to formula I where A is $-Z-C_3-C_6$-alkylene, in particular $-Z-CH_2CH_2CH_2-$, $-Z-CH_2CH_2CH_2CH_2-$, $-Z-CH_2CH=CHCH_2-$, $-Z-CH_2C(CH_3)=CHCH_2-$, $-Z-CH_2C(=CH_2)CH_2-$, $-Z-CH_2CH(CH_3)CH_2-$ or a linear $-Z-C_7-C_{10}$-alkylene radical. In this case, A is particularly preferably $-Z-C_3-C_6$-alkylene when $Ar^1$ is an unsubstituted or substituted pyrimidine or triazole residue, and a linear $-Z-C_7-C_{10}$-alkylene radical when $Ar^1$ is an unsubstituted or substituted thiadiazole residue. In this case, Z can also be $CH_2$ and is preferably $CH_2$, O and, in particular, S.

Halogen is F, Cl, Br or I.

Haloalkyl may comprise one or more, in particular 1, 2 or 3, halogen atoms which can be located on one or more carbon atoms, preferably in the α or ω position. $CF_3$, $CHF_2$, $CF_2Cl$ or $CH_2F$ is particularly preferred.

Acyl is preferably HCO or $C_1-C_6$-alkyl-CO, in particular acetyl. If $Ar^1$ is substituted, the substituent can also be located on the nitrogen heteroatom.

$Ar^1$ is preferably compounds of the formula I where $Ar^1$ is

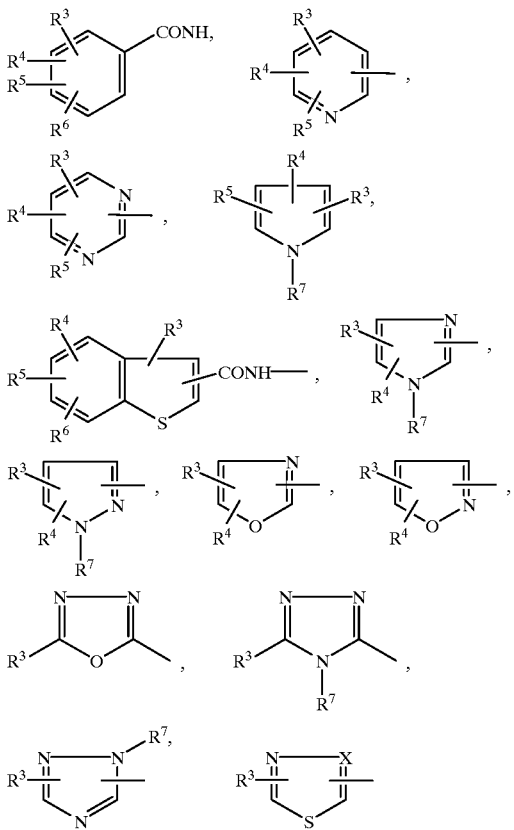

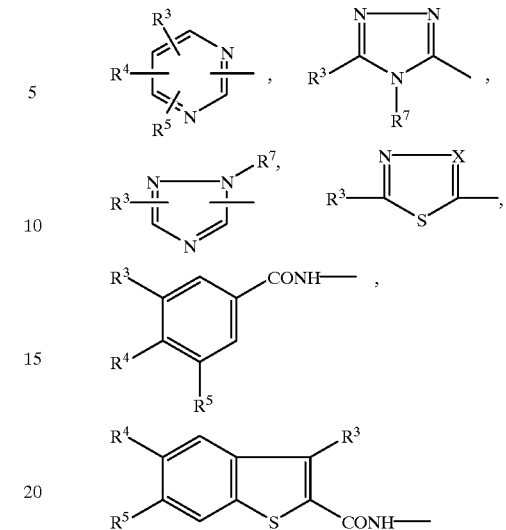

where
R³ to R⁶ are H or one of the abovementioned substituents of the Ar¹ radical,
R⁷ has the meanings indicated above for R², and
X is N or CH. When the benzamide residue is substituted, the substituents are preferably in the m or p position.

Ar¹ is particularly preferably compounds of the formula I where Ar¹ is

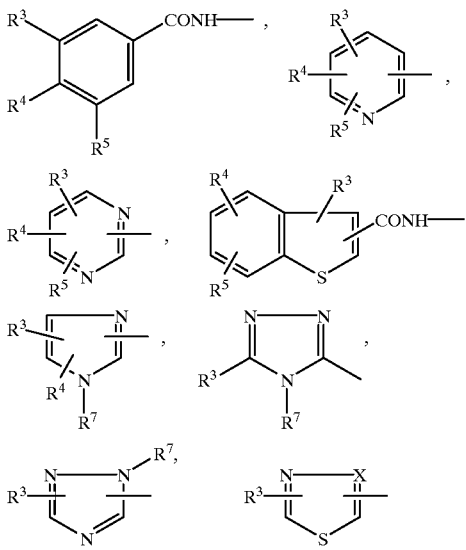

where R³ to R⁵, R⁷ and X have the abovementioned meanings, and in particular compounds of the formula I where Ar¹ is where R³ to R⁵, R⁷ and X have the abovementioned meanings.

The radicals R³ to R⁶ are preferably H, $C_1$–$C_6$-alkyl, $OR^1$, $NR^1R^2$, $SR^1$, phenyl which is substituted or unsubstituted with $C_1$–$C_6$ alkyl, acyl or halogen, and halogen, where $R^1$ and $R^2$ have the abovementioned meanings.

The radical B is preferably

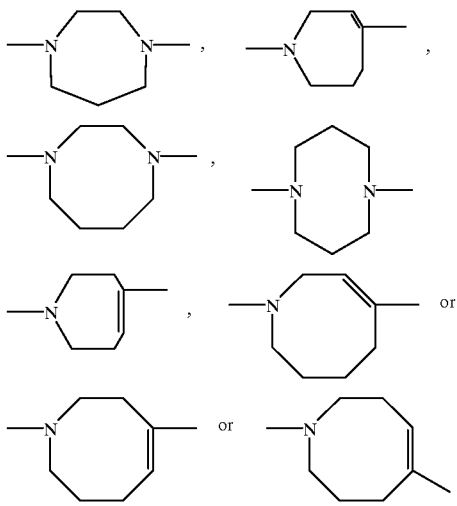

The radical Ar² may have one, two, three or four substituents, preferably one or two substituents, which are located in particular in the m position and/or p position. They are preferably selected, independently of one another, from $C_1$–$C_6$-alkyl, haloalkyl, $NO_2$, halogen, in particular chlorine, phenyl, pyrrolyl, imidazolyl, pyrazolyl, thienyl, cyclopentyl and cyclohexyl. If one of the substituents is $C_1$-Ce-alkyl, a branched group is preferred, in particular isopropyl or t-butyl.

Ar² is preferably unsubstituted or substituted phenyl, 2-, 3- or 4-pyridinyl or 2-, 4(6)- or 5-pyrimidinyl.

If one of the substituents on the radical Ar² is a 5- or 6-membered heterocyclic ring, it is, for example, a pyrrolidine, piperidine, morpholine, piperazine, pyridine, 1,4-dihydropyridine, pyrimidine, triazine, pyrrole, thiophene, thiazole, imidazole, oxazole, isoxazole, pyrazole or thiadiazole residue, with a pyrrole, imidazole, pyrrazole or thienyl radical being preferred.

If one of the substituents on the radical $Ar^2$ is a carbocyclic radical, it is, in particular, a phenyl, cyclopentyl or cyclohexyl radical.

If $Ar^2$ is fused to a carbocyclic radical, it is, in particular, a naphthalene, di- or tetrahydronaphthalene residue.

The invention also comprises the acid addition salts of the compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Other acids which can be used are described in Fortschritte der Arzneimittelforschung, Volume 10, pages 224 et seq., Birkhäuser Verlag, Basel and Stuttgart, 1966.

The compounds of the formula I may have one or more centers of asymmetry. The invention therefore includes not only the racemates but also the relevant enantiomers and diastereomers. The particular tautomeric forms are also included in the invention.

The process for preparing the compounds (I) comprises
a) reacting a compound of the general formula II

 (II)

where $Y^1$ is a conventional leaving group such as Hal, alkanesulfonyloxy, arylsulfonyloxy etc., and Z has the abovementioned meanings, with a compound of the general formula (III)

 (III)

or
b) reacting a compound of the general formula (IV)

 (IV)

where $Z^1$ is O, $NR^1$ or S and $A^1$ is $C_1$–$C_{15}$-alkylene or a bond, with a compound of the general formula V

 (V)

where $Y^1$ has the abovementioned meaning, and $A^2$ is $C_2$–$C_{15}$-alkylene, where $A^1$ and $A^2$ together have 3 to 15 carbon atoms;
or
c) reacting a compound of the general formula (VI)

 (VI)

where $Y^1$ has the abovementioned meaning, with a compound of the general formula VII

 (VII)

where $Z^1$ has the abovementioned meanings; or
d) converting a compound of the formula (VIII)

 (VIII)

into a compound of the type of (IX)

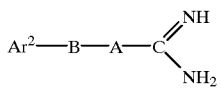 (IX)

and reacting the latter with a dicarbonyl compound in a conventional way; or
e) to prepare a compound of the formula I where $Ar^1$ is a benzamide residue:
reacting a compound of the general formula (X)

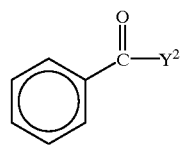 (X)

where $Y^2$ is OH, $OC_1$–$C_4$-alkyl, Cl or together with CO an activated ester group, with a compound of the formula (XI)

 (XI)

where $A^2$ has the abovementioned meanings, and $Z^2$ is OH or $NH_2$.

The compounds of the formula III are starting compounds for preparing compounds of the formulae V, VII and VIII and are prepared by
a) reacting a compound of the general formula (XII)

 (XII)

where $B^1$ is

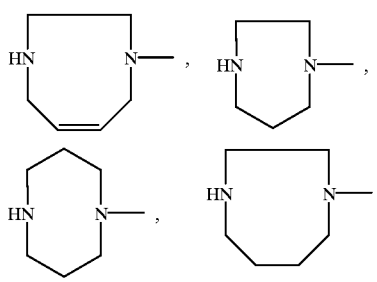

with a compound of the general formula (XIII)

 (XIII)

where $Y^1$ is one of the abovementioned leaving groups and $Ar^2$ has the abovementioned meaning, in a conventional way; or
b) reacting a compound of the general formula (XIV)

where $B^2$ is

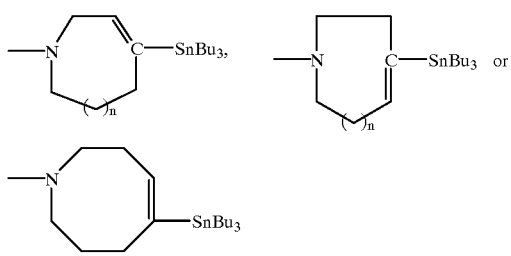

with n=1 or 2,
with a compound of the general formula (XV)

$$Y^2\text{—}Ar^2$$

where $Y^2$ is Br, Cl or I, and $Ar^2$ has the above meanings, by known processes as described, for example, by S. C. Buchwald et al., Angew. Chem. 1995, 107, 1456 or J. F. Hartweg et al., Tetrahedron Lett 1995, 36, 3604 and J. K. Stille et al., Angew. Chem. 1986, 98, 504 or Pereyre M. et al., in Organic Synthesis, Butterworth 1987; or c) reacting a compound of the general formula (XVI)

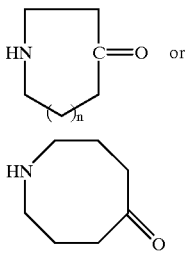

(XVI)

where n=1 or 2,
with a compound M—$Ar^2$ where M is a metal such as Li or Mg$Y^2$. M$Ar^2$ can be obtained from compounds of the formula XV by methods known from the literature.

Compounds of the type of $Ar^1$ and $Ar^2$ are either known or can be prepared by known processes as described, for example, in A. R. Katritzky, C W. Rees (ed.) "Comprehensive Heterocyclic Chemistry", Pergamon Press, or "The Chemistry of Heterocyclic Compounds", J. Wiley & Sons Inc. NY and the literature cited therein.

Compounds of type B are either known or can be prepared by processes similar to known ones, for example 1,4- and 1,5-diazacycloalkanes: L. Börjeson et al. Acta Chem. Scand. 1991, 45, 621 Majahrzah et al Acta Pol. Pharm., 1975, 32, 145

1,4-diazacyclooct-6-enes: W. Schroth et al. Z. Chem. 1969, 9, 143

1-azacyclooctanones: N. J. Leonard et al. J. Org. Chem. 1964, 34, 1066

1-azacyclo-heptanones: A. Yokoo et al. Bull Chem. Soc. Jpn. 1956, 29, 631

The novel compounds and the starting materials and intermediates can also be prepared by methods similar to those described in the patent publications mentioned at the outset.

The reactions described above generally take place in a solvent at temperatures between room temperature and the boiling point of the solvent used. Solvents which can be used are, for example, ethyl acetate, tetrahydrofuran, dimethylformamide, dimethyl sulfoxide, dimethoxyethane, toluene, xylene, a ketone such as acetone or methyl ethyl ketone, or an alcohol such as ethanol or butanol.

An acid-binding agent is present if required. Suitable acid-binding agents are inorganic bases such as sodium or potassium carbonate, sodium methoxide, sodium ethoxide, sodium hydride or organometallic compounds such as butyl-lithium or alkylmagnesium compounds, or organic bases such as triethylamine or pyridine. The latter can also act as solvent.

The reactions take place where appropriate with use of a catalyst such as transition metals or complexes thereof, eg. Pd(PPh$_3$)$_4$, Pd(OAc)$_2$ or Pd(P(oTol)$_3$)$_4$, or of a phase-transfer catalyst, eg. tetrabutylammonium chloride or tetrapropylammonium bromide.

The crude product is isolated in a conventional way, for example by filtration, removal of the solvent by distillation, or extraction from the reaction mixture etc. The resulting compounds can be purified in a conventional way, for example by recrystallization from a solvent, chromatography or conversion into an acid addition compound.

The acid addition salts are prepared in a conventional way by mixing the free base with the appropriate acid, where appropriate in solution in an organic solvent, for example a lower alcohol such as methanol, ethanol or propanol, an ether such as methyl t-butyl ether, a ketone such as acetone or methyl ethyl ketone, or an ester such as ethyl acetate.

To treat the abovementioned disorders, the compounds according to the invention are administered orally or parenterally (subcutaneously, intravenously, intramuscularly, intraperitoneally) in a conventional way. Administration can also take place with vapors or sprays through the nasopharyngeal space.

The dosage depends on the age, condition and weight of the patient and on the mode of administration. As a rule, the daily dose of active substance is about 10 to 1000 mg per patient and day on oral administration and about 1 to 500 mg per patient and day on parenteral administration.

The invention also relates to pharmaceutical compositions which comprise the compounds according to the invention. These compositions are in the form of the conventional solid or liquid pharmaceutical presentations, for example as uncoated or (film-)coated tablets, capsules, powders, granules, suppositories, solutions or sprays. The active substances can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al., Pharmazeutische Technologie, Thieme-Verlag, Stuttgart,1978). The presentations obtained in this way normally contain from 1 to 99% by weight of active substance.

The following examples serve to illustrate the invention without limiting it.

EXAMPLE 1

1-[2-t-Butyl-6-trifluoromethyl-pyrimidin-4-yl]-4-[3-[4-hydroxy-pyrimidin-2-ylmercapto)-propyl]-hexahydro-(1H))-1,4-diazepine fumarate

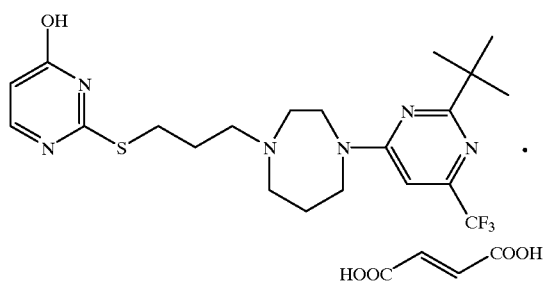

Preparation of the starting materials:

a) 2-t-Butyl-4-hydroxy-6-trifluoromethylpyrimidine.

The above pyridimine was synthesized in a conventional way by condensing 2,2-dimethylpropionamidine with ethyl trifluoroacetoacetate and sodium ethoxide in ethanol, see Heterocyclic Compounds, Vol. 52, The Pyrimidines, page 189 et seq., D. J. Brown et al. (Eds.) John Wiley and Sons, 1994.

Melting point 187–188° C.

The 4-hydroxypyrimidines of the formula

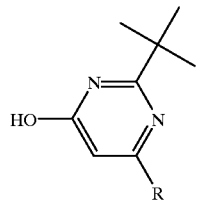

were obtained in a similar way.

| R | M.p. [° C.] |
|---|---|
| t-C$_4$H$_9$ | 169 |
| n-C$_3$H$_7$ | 120 |
| CF$_2$Cl | 135–136 | b) 2-t-Butyl-4-chloro-6-trifluoromethylpyrimidine The hydroxypyrimidine from stage a) was converted with phosphorus oxychloride or thionyl chloride in a conventional way into the chlorine compound, see Heterocyclic Compounds, Vol. 52, The pyrimidines, page 329 et seq., John Wiley and Sons, 1994. The compound is in the form of a yellowish oil.

The 4-chloropyrimidines of the formula

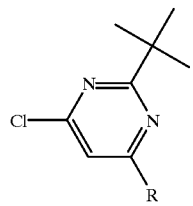

were obtained in a similar way:

| R | M.p. [° C.] |
|---|---|
| t-C$_4$H$_9$ | oil |
| n-C$_3$H$_7$ | oil |
| CF$_2$Cl | oil | c) 1-[2-t-Butyl-6-trifluoromethylpyrimidin-4-yl]hexahydro-(1H))-, 1,4-diazepine 18 g (0.18 mol) of homopiperazine were dissolved in 25 ml of ethanol and, while refluxing, a solution of 7.2 g (0.03 mol) of the chloride obtained in b), dissolved in 10 ml of ethanol, was added dropwise over the course of 1 h. After reacting for a further 30 min, the cooled mixture was worked up by adding 200 ml of water and extracting several times with a total of 200 ml of methylene chloride. The organic phase was then washed with water, dried with anhydrous sodium sulfate and concentrated. The required compound was obtained as a yellowish oil which was further processed unpurified. Yield: 98% of theory.

The following compounds were obtained in a corresponding way: 1-aryl-1,4-diazepine of the formula:

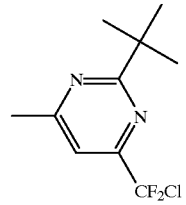

| Ar$^2$ | M.p. [° C.] |
|---|---|
| 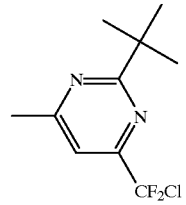 | Oil |
| 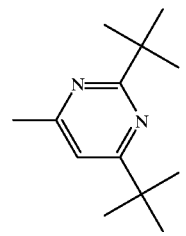 | Oil |
| 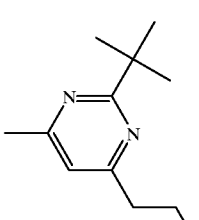 | Oil |

-continued

[Structure: HN-[diazepine ring]-N-Ar²]

| Ar² | M.p. [° C.] |
|---|---|
| 4-methyl-2-CF₃-3-NO₂-phenyl (with CF₃ and NO₂ substituents) | 74–75 | d) 1-[2-t-Butyl-6-trifluoromethylpyrimidin-4-yl]-4-(3-chloropropyl)hexahydro-(1H))-1,4-diazepine 5 g (0.0165 mol) of the compound obtained above under c) were refluxed together with 2.5 g (0.025 mol) of triethylamine and 3.15 g (0.02 mol) of 1-bromo-3-chloropropane in 50 ml of tetrahydrofuran for 10 h. The solvent was then removed by distillation, and the residue was washed with water and extracted with methylene chloride. The residue obtained after drying and concentrating was then purified by flash chromatography (silica gel).

Yield: 4.8 g (77% of theory) of yellow oil

The compounds listed below were obtained in a similar manner:

1-aryl-4-haloalkyl-1,4-diazepines of the formula

Hal—alk—N[diazepine ring]N—Ar²

| Hal | alk | Ar² | M.p. [° C.] |
|---|---|---|---|
| Cl | —CH₂—CH(CH₃)—CH₂— | 2-t-Bu-6-CF₃-pyrimidin-4-yl (methyl substituted) | Oil |
| " | —CH₂C(=CH₂)—CH₂— | " | Oil |
| " | —(CH₂)₃— | 2,6-di-t-Bu-pyrimidin-4-yl (methyl substituted) | Oil |
| " | " | 2-t-Bu-6-propyl-pyrimidin-4-yl (methyl substituted) | Oil |

-continued

Hal—alk—N‾N—Ar²

| Hal | alk | Ar² | M.p. [° C.] |
|---|---|---|---|
| " | " | 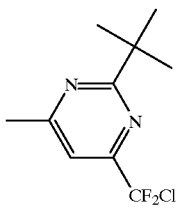 | Oil |
| " | —CH₂—C(CH₃)=CH—CH₂— | 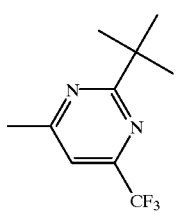 | Oil |
| " | —(CH₂)₃— | 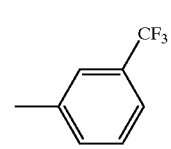 | Oil |
| " | " | 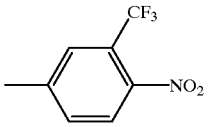 | Oil |

Preparation of the final product 5 g (0.013 mol) of the product obtained in d) were dissolved in 25 ml of dimethylformamide and added dropwise to a stirred solution at 100° C. of 2.03 g (0.016 mol) of 2-thiouracil, 0.38 g (0.016 mol) of lithium hydroxide and 1 g of sodium iodide in 50 ml of dimethylformamide over the course of 1 h. After reaction for 3 hours, the solvent was removed by distillation under reduced pressure, and the residue was mixed with 150 ml of water and extracted twice with ethyl acetate. The residue obtained after washing with water, drying with sodium sulfate and concentrating was purified by chromatography. (Flash chromatography, silica gel, mobile phase methylene chloride with 2.5–5% methanol)

Yield: 4 g of pale oil

NMR:CDCl₃.δ 1.3(s,9H); 1.85–2.25(m,4H); 2.6(m,4H); 2.8(m,2H); 3.2(t,2H); 3.5(m,2H); 4.0(m,2H); 6.2(d,1H); 6.5 (s,1H); 7.8(d;1H)

The substance was obtained as fumarate by adding an ethanolic solution of fumaric acid.

$C_{21}H_{29}F_3N_6OS \cdot C_4H_4O_4$ MW 586.6

Melting point: 188–189° C.

The compounds listed in the following Table 1 were obtained in a similar way using various haloalkyl-1,4-diazepines (eg. 1d) and various mercapto-substituted heterocycles such as thiouracil, 5-amino-2-mercaptotriazoles and 5-amino-2-mercaptothiadiazole:

TABLE 1
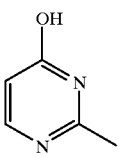
| Ex. No. | Ar¹ | alk | Ar² | M.p. [° C.] |
|---|---|---|---|---|
| 2 | 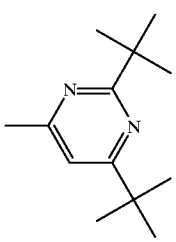 | —(CH$_2$)$_3$— | 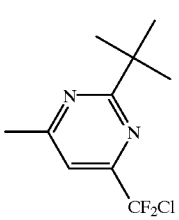 | 155–162 Oxalate |
| 3 | " | " | 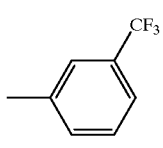 | 83–85 Oxalate |
| 4 | " | " | 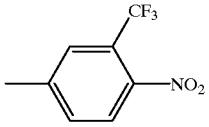 | 177–182 Fumarate |
| 5 | " | " | 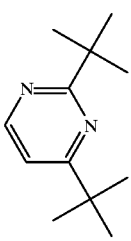 | 72–74 |
| 6 | " | —CH$_2$—CH—CH$_2$—<br>        \|<br>        CH$_3$ | 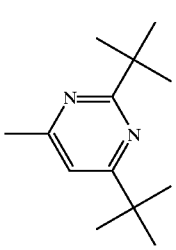 | 116–119 |
| 7 | " | —CH$_2$—C—CH$_2$—<br>       \|\|<br>       CH$_2$ | | 174–180 Oxalate |

TABLE 1-continued $$Ar^1-S-alk-N\underset{\underset{}{\diagdown}}{\overset{\overset{}{\diagup}}{N}}-Ar^2$$

| Ex. No. | Ar¹ | alk | Ar² | M.p. [° C.] |
|---|---|---|---|---|
| 8 | " | " | 2-tert-butyl-4-methyl-6-propyl-pyrimidin-...yl | 60–70 Oxalate |
| 9 | 5-amino-1,4-dimethyl-1,2,4-triazol-3-yl | —(CH₂)₃— | 2-tert-butyl-4-methyl-6-trifluoromethyl-pyrimidin-...yl | 166–167 Fumarate |
| 10 | " | " | 2,6-di-tert-butyl-4-methyl-pyrimidin-...yl | 55–60 |
| 11 | " | " | 2-tert-butyl-6-chlorodifluoromethyl-4-methyl-pyrimidin-...yl | 110–115 Oxalate |
| 12 | " | " | 3-trifluoromethyl-phenyl | 136–140 Hydrochloride |
| 13 | " | " | 2-trifluoromethyl-3-nitro-phenyl | 95–98 |
| 14 | 1-isopropyl-4-methyl-5-methylamino-1,2,4-triazol-3-yl | " | 2-tert-butyl-4-methyl-6-trifluoromethyl-pyrimidin-...yl | 142–144 |

TABLE 1-continued

Ar¹—S—alk—N(piperazine)N—Ar²

| Ex. No. | Ar¹ | alk | Ar² | M.p. [° C.] |
|---|---|---|---|---|
| 15 | 3-amino-1,4-dimethyl-1,2,4-triazol-5-yl | —CH₂—CH(CH₃)—CH₂— | 2,6-di-tert-butyl-4-methylpyrimidin-... | 125–128 |
| 16 | " | —CH₂—C(=CH₂)—CH₂— | 2-tert-butyl-4-methyl-6-propylpyrimidinyl | 113–119 Oxalate |
| 17 | " | " | 2-tert-butyl-4-methyl-6-(trifluoromethyl)pyrimidinyl | 230–232 Hydrochloride |
| 18 | 2-amino-5-methyl-1,3,4-thiadiazol-yl | —(CH₂)₃— | 2-tert-butyl-4-methyl-6-(trifluoromethyl)pyrimidinyl | Oil |
| 19 | " | " | 2-tert-butyl-4-methyl-6-(chlorodifluoromethyl)pyrimidinyl | 109–110 |
| 20 | " | " | 2,6-di-tert-butyl-4-methylpyrimidinyl | 60–67 |

TABLE 1-continued

Ar¹—S—alk—N⟨ring⟩N—Ar²

| Ex. No. | Ar¹ | alk | Ar² | M.p. [° C.] |
|---|---|---|---|---|
| 21 | " | —CH₂—CH(CH₃)—CH₂— | " | 180–190 Hydrochloride |
| 22 | " | —CH₂—C(=CH₂)—CH₂— | " | 119–122 |
| 23 | " | —CH₂—CH(CH₃)—CH₂— | 2-t-butyl-6-methyl-4-propyl-pyrimidinyl | 92–97 Oxalate |

EXAMPLE 24

1-(4-Bromobenzamido)-4-[4-(2,6-bis-t-butyl-4-pyrimidinyl)hexahydro-(1H)-1,4-diazepin-1-yl]butane

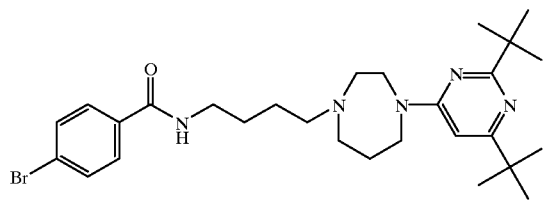

Preparation of the starting materials a) Hexahydro-1-[2-t-butyl-6-trifluoromethyl-4-pyrimidinyl]-4-(4-phthalimidobutyl)-(1H)-1,4-diazepine 10 g (0.033 mol) of the diazepine prepared in Example 1c) were refluxed with 9.8 g (0.035 mol) of N-(4-bromobutyl)phthalimide and 9.1 g (0.066 mol) of potassium carbonate in 120 ml of acetonitrile for 8 h. The mixture was filtered and the filtrate was concentrated. The residue was processed further unpurified.

Yield: 16.2 g (98% of theory)

A sample was recrystallized from ethanol.
Melting point 97–99° C.

The following were obtained in a similar way:

Phthalimido—alk—N⟨ring⟩N—Ar²

| alk | Ar² | M.p. [° C.] |
|---|---|---|
| —(CH₂)₃— | 2-t-butyl-6-methyl-4-CF₃-pyrimidinyl | 89–92 |
| —CH₂—C(CH₃)=CH—CH₂— | " | 130–132 |
| —(CH₂)₃— | 2,6-di-t-butyl-4-methyl-pyrimidinyl | 119–121 |
| —(CH₂)₄— | " | 207–209 |

-continued

| alk | Ar² | M.p. [° C.] |
|---|---|---|
| —(CH₂)₄— | 4-methyl-2-t-butyl-6-(CF₂Cl)-pyrimidinyl | 190–192 | b) Hexahydro-1H-1-[2-t-butyl-6-trifluoromethyl-4-pyrimidinyl]-4-(4-aminobutyl)-1,4-diazepine 15 g (0.03 mol) of the product described above under a) were refluxed with 6 g of hydrazine hydrate in 200 ml of ethanol for 2 h, and then the precipitate was filtered off with suction and the filtrate was evaporated. The residue was taken up in ethyl acetate, filtered again, washed with water, dried and again evaporated.

9.2 g (83% of theory) were obtained as an oil.

The following were obtained in a similar way:

| alk | Ar² | M.p. [° C.] |
|---|---|---|
| —(CH₂)₄— | 4-methyl-2,6-di-t-butyl-pyrimidinyl | Oil |
| —(CH₂)₃— | " | Oil |
| —(CH₂)₄— | 4-methyl-2-t-butyl-6-(CF₂Cl)-pyrimidinyl | Oil |

| alk | Ar² | M.p. [° C.] |
|---|---|---|
| —(CH₂)₃— | 4-methyl-2-t-butyl-6-CF₃-pyrimidinyl | Di-Hydrochloride: 241–245 |

Preparation of the final products:

3 g (0.0083 mol) of the product obtained above under b) were dissolved with 0.9 g (0.009 mol) of triethylamine in 60 ml of tetrahydrofuran, and a solution of 2 g (0.009 mol) of 4-bromobenzoyl chloride in 10 ml of tetrahydrofuran was added dropwise at room temperature over the course of 10 min. After 1 h, the solvent was removed by distillation under reduced pressure, and the residue was mixed with water and extracted twice with methylene chloride. The dried and concentrated solvent phase was purified by flash chromatography (silica gel, mobile phase methylene chloride with 3% methanol).

Yield: 4.2 g (93% of theory)

Melting point 125–127° C. (from diisopropyl ether/isopropanol) $C_{28}H_{42}BrN_5O$ (544.6)

The compounds listed in Table 2 below were obtained using various amino derivatives (similar to 24b) and known benzoyl chlorides.

TABLE 2

R—C₆H₄—CONH—(CH₂)ₙ—N(diazepine)—Ar²

| Ex. No. | R | n | Ar² | M.p. [° C.] |
|---|---|---|---|---|
| 25 | Br | 3 | 4-methyl-2-t-butyl-6-CF₃-pyrimidinyl | 169–171 |
| 26 | " | 4 | " | 74–76 Oxalate |

TABLE 2-continued

R—⟨benzene⟩—CONH—(CH₂)$_n$—N(piperazine)N—Ar²

| Ex. No. | R | n | Ar² | M.p. [° C.] |
|---|---|---|---|---|
| 27 | t-Butyl | 4 | 2,6-di-t-butyl-4-methylpyrimidinyl | 165–167 Oxalate |
| 28 | phenoxy | 4 | " | 104–107 Oxalate |
| 29 | Br | 4 | 2-t-butyl-6-methyl-4-(CF₂Cl)-pyrimidinyl | 92–94 Oxalate |
| 30 | I | 4 | " | 110–115 Oxalate |

EXAMPLE 31
4-[4-{4-Benzyloxy-2-pyrimidinylamino}butyl]-1-[2-t-butyl-6-trifluoromethyl-4-pyrimidinyl]hexahydro-1H-1,4-diazepine oxalate

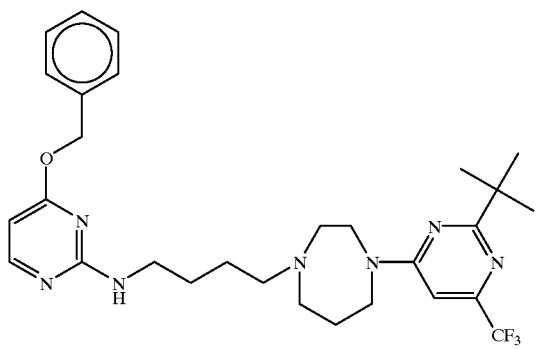

2.7 g (0.007 mol) of the amino compound prepared in Example 24b) were introduced with 0.3 g of sodium hydride (0.009 mol) into 20 ml of dimethylformamide. After reaction for 1 h, 1.6 g (0.006 mol) of 4-benzyloxy-2-methylsulfonylpyrimidine (prepared by oxidizing 4-benzyloxy-2-methylmercaptopyrimidine), dissolved in 10 ml of dimethylformamide, were added, and the mixture was stirred at room temperature for 72 h.

Subsequently, water was added, the mixture was extracted with ethyl acetate, and the solution was dried and concentrated. The residue was purified by column chromatography (silica gel, methylene chloride with 4% methanol)

Pure yield: 1.0 g (30% of theory)

Oxalate: Melting point 145–150° C. $C_{29}H_{38}F_3N_7O.C_2H_2O_4$ (647.7)

EXAMPLE 32
1-[2-t-Butyl-6-trifluoromethyl-4-pyrimidinyl]-4-[4-{4-hydroxy-2-pyrimidinylamino}butyl]hexahydro-(1H))-1,4-diazepine

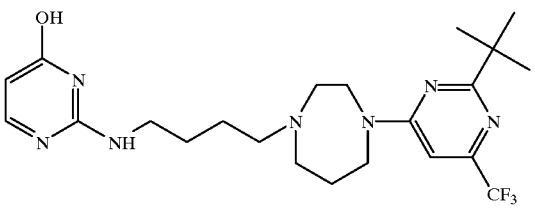

0.7 g (0.001 mol) of the compound described in the previous example was hydrogenated in methanol with palladium on carbon catalyst (10% Pd) under normal conditions.

Yield: 0.6 g (100% of theory)

Melting point 111–115° C. $C_{22}H_{32}F_3N_7O.C_2H_4O_4$ (557.5)

EXAMPLE 33
1-[2-t-Butyl-6-trifluoromethyl-4-pyrimidinyl]-4-[4-(4-hydroxy-2-pyrimidinyl)butyl]hexahydro-1H-1,4-diazepine

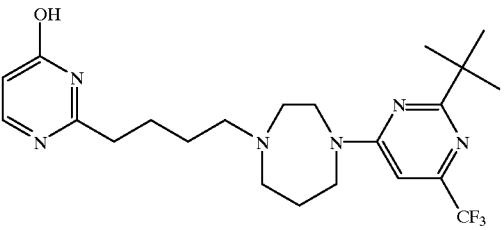

a) 1-[2-t-Butyl-6-trifluoromethyl-4-pyrimidinyl]-4-(4-cyanobutyl)hexahydro-1,4-diazepine 9.1 g (0.03 mol) of the diazepine from Example 1c) were dissolved with 3.5 g (0.03 mol) of 5-chlorovaleronitrile and 9.1 g of triethylamine (0.09 mol) in 100 ml of dimethylformamide and heated at 100° C. for 24 h.

The solvent was then removed by distillation under reduced pressure, water was added, the mixture was extracted with ethyl acetate, and this phase was dried with sodium sulfate and concentrated. The residue was processed further unpurified.

Yield: 9.1 g as brown oil b) 1-[2-t-Butyl-6-trifluoromethyl-4-pyrimidinyl]-4-(4-amidino-butyl)hexahydro-1,4-diazepine hydrochloride 9.1 g (0.024 mol) of the nitrile described above were dissolved in 2 ml of ethanol and 50 ml of methylene chloride (both anhydrous) and, while cooling to 0–10° C., dry hydrogen chloride gas was passed in to saturation. After stirring overnight, the precipitate was filtered off with suction and the filtrate was concentrated.

Yield: 7.6 g (58% of theory)

Preparation of the final product 4.4 g (0.01 mol) of the amidine described above were stirred with the sodium compound of ethyl formylacetate (preparation J. Org. Chem. 35 (1970), 2515 et seq.) (2.8 g (0.02 mol)) in 50 ml of water and 20 ml of tetrahydrofuran overnight. The reaction mixture was then extracted several times with ethyl acetate, and the organic phase was dried and concentrated. The residue was purified by column chromatography (silica gel, eluent methylene chloride with 4% methanol)

Yield: 1.9 g (42%) of oil

NMR: (CDCl$_3$) δ: 1.3(s,9H); 1.8–2.0(m,4H); 2.0(m,2H); 2.4–2.6(m/br,6H); 2.5(t,2H); 3.5(m,1H); 4.0(m,2H); 6.2(d, 1H); 6.5(s,1H); 7.8(d,1H) $C_{22}H_{31}F_3N_6O$ (425.5)

Oxalate: $C_{22}H_{31}F_3N_6O \cdot C_2H_2O_4$ (542.5)

Melting point 173–177° C. (decomposition)

EXAMPLE 34

1-[2-t-Butyl-6-trifluoromethyl-4-pyrimidinyl]-4-[3-{4-benzyloxy-2-pyrimidinyloxy}propyl]hexahydro-(1H))-1,4-diazepine

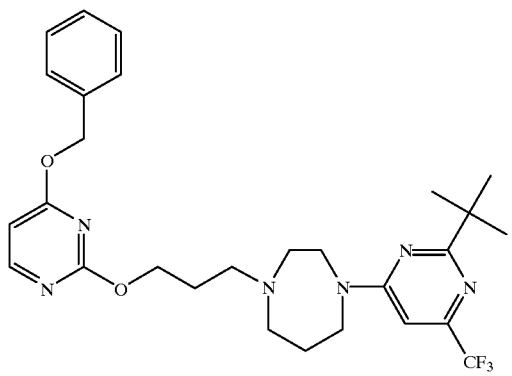

a) Starting material 8.9 g (64.5 mmol) of 3-bromo-1-propanol were taken up in 50 ml of abs. THF, and 6.52 g (64.5 mmol) of triethylamine, a catalytic amount of sodium iodide and 16.2 g (53.7 mmol) of the azepine prepared in Example 1c) were successively added, and the mixture was refluxed for 16 h. For workup, the precipitate salts were filtered off and the mother liquor was concentrated under reduced pressure. The resulting oil was taken up in dichloromethane, and the organic phase was washed with water, dried over sodium sulfate and then purified by column chromatography (SiO$_2$, mobile phase CH$_2$Cl$_2$:MeOH=98:2) to result in a colorless oil.

Yield: 10.11 g (53%)

b) Final product 0.26 g (8.52 mmol) of sodium hydride (80%) was added in portions to 2.45 g of the product described above, dissolved in 25 ml of abs. DMF, at room temperature under a protective gas atmosphere, and the mixture was stirred for 30 min. Then 1.5 g (5.68 mmol) of 2-methanesulfonyl-4-benzyloxypyrimidine (prepared by methods similar to the literature: W. E. Barnett, R. F. Koebel Tetrahedron Lett. 1971, 20, 2867) dissolved in 15 ml of abs. DMF, were added dropwise. After 7 h, the mixture was worked up by pouring into water and extracting with tert-butyl methyl ether. The organic phase was washed with water, dried over sodium sulfate, filtered and concentrated under reduced pressure. The resulting oil was purified by column chromatography (SiO$_2$, mobile phase CH$_2$Cl$_2$:MeOH=98:2) to afford the substance as an oil.

Yield: 1.6 g (2.9 mmol, 52%)

To form the hydrochloride, the oil was dissolved in ethyl acetate/Et$_2$O, ethereal hydrochloric acid was added under protective gas, and the resulting salt was filtered off with suction.

Melting point: 110–112° C. $C_{28}H_{36}ClF_3N_6O_2$ (581.1)

EXAMPLE 35

1-[2-t-Butyl-6-trifluoromethyl-2-pyrimidinyl]-4-[3-(4-hydroxy-2-pyrimidinyloxy)propyl]hexahydro-(1H)-1,4-diazepine

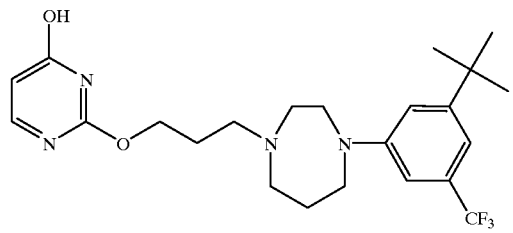

1.4 g (2.6 mmol) of the substance from Example 34, dissolved in 40 ml of ethyl acetate, were mixed at room temperature with 0.2 g of Pd/C (10% Pd) and hydrogenated with hydrogen at 40–50° C. under atmospheric pressure. After the reaction was complete, the catalyst was filtered off with suction and, after washing with ethyl acetate, the filtrated was concentrated under reduced pressure.

Yield: 1.2 g (100%)

To form the hydrochloride, the oil was dissolved in ethyl acetate/Et$_2$O, ethereal hydrochloric acid was added under protective gas, and the resulting salt was filtered off with suction.

Melting point: 78–80° C. $C_{21}H_{30}ClF_3N_6O_2$ (491)

The compounds mentioned in the following Tables 3 to 17 are obtained in a similar way.

TABLE 3

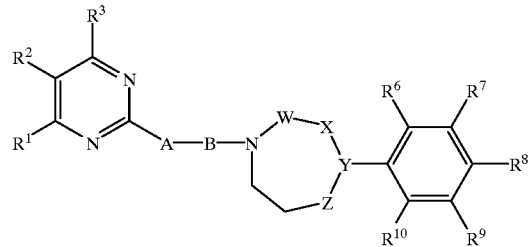

| Example No. | R1 | R2 | R3 | R6 | R7 | R8 | R9 | R10 | W | X—Y—Z | A | B |
|---|---|---|---|---|---|---|---|---|---|---|---|---|
| 36 | H | H | OH | H | tBut | H | Me | H | $CH_2$ | $CH_2$—N—$CH_2$ | —$CH_2$— | —$(CH_2)_3$— |
| 37 | H | H | OH | H | tBut | H | Ph | H | $CH_2$—$CH_2$ | CH=C—$CH_2$ | S | —$(CH_2)_3$— |
| 38 | Me | H | OH | H | tBut | H | 1-Pyrrolyl | H | $CH_2$ | CH=C—$CH_2$ | S | —$(CH_2)_3$— |
| 39 | H | H | $NH_2$ | H | iProp | H | 2-Napht | H | $CH_2$—$CH_2$ | $CH_2$—CH=C | S | —$(CH_2)_3$— |
| 40 | H | Me | OH | H | Et | H | tBut | H | $CH_2$ | $CH_2$—N—$CH_2$ | —$CH_2$— | —$(CH_2)_3$— |
| 41 | H | H | OH | H | $CHF_2$ | H | H | H | $CH_2$ | $CH_2$—CH=C | S | —$(CH_2)_3$— |
| 42 | H | H | $NH_2$ | OMe | $CF_3$ | H | H | H | $CH_2$ | CH=C—$CH_2$ | S | —$(CH_2)_3$— |
| 43 | H | H | OH | H | $CF_3$ | H | tBut | H | $CH_2$—$CH_2$ | $CH_2$—N—$CH_2$ | —$CH_2$— | —$(CH_2)_3$— |
| 44 | H | H | NHMe | H | iProp | H | H | H | $CH_2$ | $CH_2$—N—$CH_2$ | O | —$(CH_2)_4$— |
| 45 | Me | H | OH | H | H | CN | tBut | H | $CH_2$—$CH_2$ | $CH_2$—N—$CH_2$ | —$CH_2$— | —$(CH_2)_3$— |
| 46 | H | H | OH | H | H | F | tBut | H | $CH_2$—$CH_2$ | $CH_2$—CH=C | S | —$(CH_2)_3$— |
| 47 | H | Me | $NH_2$ | H | H | Cl | iProp | H | $CH_2$—$CH_2$ | $CH_2$—N—$CH_2$ | —$CH_2$— | —$(CH_2)_3$— |
| 48 | H | H | NHMe | H | tBut | H | H | OMe | $CH_2$ | $CH_2$—CH=C | S | —$(CH_2)_3$— |
| 49 | H | H | OH | H | iProp | H | H | OMe | $CH_2$ | $CH_2$—N—$CH_2$ | —$CH_2$— | —$(CH_2)_4$— |
| 50 | H | H | OH | H | $CHF_2$ | H | tBut | H | $CH_2$—$CH_2$ | CH=C—$CH_2$ | S | —$(CH_2)_3$— |
| 51 | H | H | OH | OMe | tBut | H | $CF_3$ | H | $CH_2$—$CH_2$ | $CH_2$—N—$CH_2$ | —$CH_2$— | —$(CH_2)_3$— |
| 52 | Me | H | OH | H | $CF_3$ | H | tBut | H | $CH_2$ | $CH_2$—N—$CH_2$ | O | —$(CH_2)_5$— |
| 53 | H | H | $NH_2$ | H | nProp | CN | tBut | H | $CH_2$ | $CH_2$—N—$CH_2$ | —$CH_2$— | —$(CH_2)_3$— |
| 54 | H | Me | OH | H | $CF_3$ | CN | iProp | H | $CH_2$ | CH=C—$CH_2$ | S | —$(CH_2)_3$— |
| 55 | H | H | OH | H | Ph | C≡CH | tBut | H | $CH_2$—$CH_2$ | $CH_2$—N—$CH_2$ | —$CH_2$— | —$(CH_2)_3$— |
| 56 | H | H | $NH_2$ | H | tBut | CN | H | H | $CH_2$ | $CH_2$—CH=C | S | —$(CH_2)_3$— |
| 57 | H | H | NHMe | H | tBut | CN | $CF_3$ | OMe | $CH_2$—$CH_2$ | $CH_2$—N—$CH_2$ | —$CH_2$— | —$(CH_2)_5$— |
| 58 | H | H | OH | OMe | nProp | F | tBut | H | $CH_2$ | $CH_2$—N—$CH_2$ | —$CH_2$— | —$(CH_2)_4$— |
| 59 | H | H | OH | H | Ph | CN | tBut | Me | $CH_2$ | $CH_2$—CH=C | S | —$(CH_2)_3$— |
| 60 | H | H | OH | OMe | tBut | F | H | H | $CH_2$—$CH_2$ | $CH_2$—N—$CH_2$ | —$CH_2$— | —$(CH_2)_3$— |
| 61 | H | H | OH | H | tBut | H | Me | H | $CH_2$ | $CH_2$—N—$CH_2$ | —$CH_2$— | —$CH_2$—C(=$CH_2$)—$CH_2$— |
| 62 | H | H | OH | H | tBut | H | Ph | H | $CH_2$ | $CH_2$—CH=C | S | —$CH_2$—C(=$CH_2$)—$CH_2$— |
| 63 | Me | H | OH | H | tBut | H | 1-Pyrrolyl | H | $CH_2$—$CH_2$ | CH=C—$CH_2$ | S | —$CH_2$—C(=$CH_2$)—$CH_2$— |
| 64 | H | H | $NH_2$ | H | iProp | H | 2-Napht | H | $CH_2$—$CH_2$ | $CH_2$—CH=C | S | —$CH_2$—C($CH_3$)=CH—$CH_2$— |
| 65 | H | Me | OH | H | Et | H | tBut | H | $CH_2$ | $CH_2$—N—$CH_2$ | —$CH_2$— | —$CH_2$—CH($CH_3$)—$CH_2$— |
| 66 | H | H | OH | H | $CHF_2$ | H | H | H | $CH_2$—$CH_2$ | CH=C—$CH_2$ | S | —$CH_2$—C(=$CH_2$)—$CH_2$— |
| 67 | H | H | $NH_2$ | OMe | $CF_3$ | H | H | H | $CH_2$ | $CH_2$—CH=C | S | —$CH_2$—CH($CH_3$)—$CH_2$— |
| 68 | H | H | OH | H | $CF_3$ | H | tBut | H | $CH_2$—$CH_2$ | $CH_2$—N—$CH_2$ | —$CH_2$— | —$CH_2$—C(=$CH_2$)—$CH_2$— |
| 69 | H | H | NHMe | H | iProp | H | H | H | $CH_2$ | $CH_2$—N—$CH_2$ | O | —$CH_2$—C(=$CH_2$)—$CH_2$— |
| 70 | Me | H | OH | H | H | CN | tBut | H | $CH_2$ | $CH_2$—N—$CH_2$ | —$CH_2$— | —$CH_2$—CH=CH—$CH_2$— |
| 71 | H | H | OH | H | H | F | tBut | H | $CH_2$—$CH_2$ | $CH_2$—CH=C | S | —$CH_2$—C($CH_3$)=CH—$CH_2$— |
| 72 | H | Me | $NH_2$ | H | H | Cl | iProp | H | $CH_2$—$CH_2$ | $CH_2$—N—$CH_2$ | —$CH_2$— | —$CH_2$—C(=$CH_2$)—$CH_2$— |
| 73 | H | H | NHMe | H | tBut | H | H | OMe | $CH_2$ | $CH_2$—CH=C | S | —$CH_2$—CH($CH_3$)—$CH_2$— |
| 74 | H | H | OH | H | iProp | H | H | OMe | $CH_2$ | $CH_2$—N—$CH_2$ | —$CH_2$— | —$CH_2$—CH($CH_3$)—$CH_2$— |
| 75 | H | H | OH | H | $CHF_2$ | H | tBut | H | $CH_2$—$CH_2$ | $CH_2$—CH=C | S | —$CH_2$—C(=$CH_2$)—$CH_2$— |
| 76 | H | H | OH | OMe | tBut | H | $CF_3$ | H | $CH_2$ | $CH_2$—N—$CH_2$ | —$CH_2$— | —$CH_2$—CH=CH—$CH_2$— |
| 77 | Me | H | OH | OMe | $CF_3$ | H | tBut | H | $CH_2$ | $CH_2$—N—$CH_2$ | O | —$CH_2$—C(=$CH_2$)—$CH_2$— |
| 78 | H | H | $NH_2$ | H | nProp | CN | tBut | H | $CH_2$—$CH_2$ | $CH_2$—N—$CH_2$ | —$CH_2$— | —$CH_2$—C($CH_3$)=CH—$CH_2$— |
| 79 | H | Me | OH | H | $CF_3$ | CN | iProp | H | $CH_2$ | CH=C—$CH_2$ | S | —$CH_2$—CH($CH_3$)—$CH_2$— |
| 80 | H | H | OH | H | Ph | C≡CH | tBut | H | $CH_2$—$CH_2$ | $CH_2$—N—$CH_2$ | —$CH_2$— | —$CH_2$—CH($CH_3$)—$CH_2$— |
| 81 | H | H | $NH_2$ | H | tBut | CN | H | H | $CH_2$ | $CH_2$—CH=C | S | —$CH_2$—C($CH_3$)=CH—$CH_2$— |
| 82 | H | H | NHMe | H | tBut | CN | $CF_3$ | OMe | $CH_2$—$CH_2$ | $CH_2$—N—$CH_2$ | —$CH_2$— | —$CH_2$—CH=CH—$CH_2$— |
| 83 | H | H | OH | H | nProp | F | tBut | H | $CH_2$ | $CH_2$—N—$CH_2$ | —$CH_2$— | —$CH_2$—CH($CH_3$)—$CH_2$— |
| 84 | H | H | OH | H | Ph | CN | tBut | Me | $CH_2$—$CH_2$ | $CH_2$—CH=C | S | —$CH_2$—C($CH_3$)=CH—$CH_2$— |
| 85 | H | H | OH | H | tBut | F | H | H | $CH_2$ | $CH_2$—N—$CH_2$ | —$CH_2$— | —$CH_2$—C(=$CH_2$)—$CH_2$— |

TABLE 4

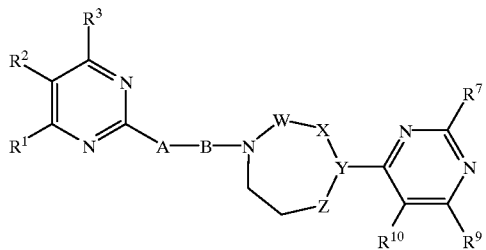

| Example No. | R1 | R2 | R3 | R7 | R9 | R10 | W | X—Y—Z | A | B |
|---|---|---|---|---|---|---|---|---|---|---|
| 86 | H | H | OH | tBut | Ph | H | CH$_2$ | CH$_2$—N—CH$_2$ | —CH$_2$— | —(CH$_2$)$_3$— |
| 87 | H | H | OH | tBut | 2-Napht | H | CH$_2$ | CH$_2$—N—CH$_2$ | S | —(CH$_2$)$_3$— |
| 88 | Me | H | OH | tBut | 1-Pyrrolyl | H | CH$_2$ | CH$_2$—N—CH$_2$ | S | —CH$_2$—C(=CH$_2$)—CH$_2$— |
| 89 | H | H | NH$_2$ | tBut | cHex | H | CH$_2$—CH$_2$ | CH=C—CH$_2$ | —CH$_2$— | —CH$_2$—C(CH$_3$)=CH—CH$_2$— |
| 90 | H | H | OH | tBut | nHex | H | CH$_2$—CH$_2$ | CH$_2$—N—CH$_2$ | S | —(CH$_2$)$_3$— |
| 91 | H | H | OH | tBut | H | OMe | CH$_2$ | CH$_2$—N—CH$_2$ | —CH$_2$— | —CH$_2$—CH(CH$_3$)—CH$_2$— |
| 92 | H | Me | OH | iProp | F | H | CH$_2$—CH$_2$ | CH$_2$—N—CH$_2$ | S | —CH$_2$—CH=CH—CH$_2$— |
| 93 | H | H | NH$_2$ | CH$_3$ | 1-Pyrrolyl | H | CH$_2$ | CH$_2$—C=CH | NH | —(CH$_2$)$_3$— |
| 94 | H | H | OH | OMe | 1-Pyrrolyl | H | CH$_2$ | CH$_2$—N—CH$_2$ | O | —CH$_2$—CH(CH$_3$)—CH$_2$— |
| 95 | H | H | OH | tBut | H | CH$_3$ | CH$_2$—CH$_2$ | CH=C—CH$_2$ | S | —CH$_2$—CH(CH$_3$)—CH$_2$— |
| 96 | H | H | OH | tBut | tBut | OMe | CH$_2$—CH$_2$ | CH$_2$—N—CH$_2$ | S | —(CH$_2$)$_3$— |
| 97 | Me | H | OH | tBut | iProp | H | CH$_2$ | CH$_2$—N—CH$_2$ | S | —CH$_2$—C(=CH$_2$)—CH$_2$— |
| 98 | H | H | NH$_2$ | Ph | Cl | H | CH$_2$ | CH$_2$—C=CH | —CH$_2$— | —CH$_2$—C(CH$_3$)=CH—CH$_2$— |
| 99 | H | H | OH | 2-Napht | tBut | Me | CH$_2$—CH$_2$ | CH=C—CH$_2$ | S | —(CH$_2$)$_3$— |
| 100 | H | H | OH | tBut | CF$_3$ | Me | CH$_2$ | CH$_2$—N—CH$_2$ | —CH$_2$— | —CH$_2$—C(=CH$_2$)—CH$_2$— |

TABLE 5

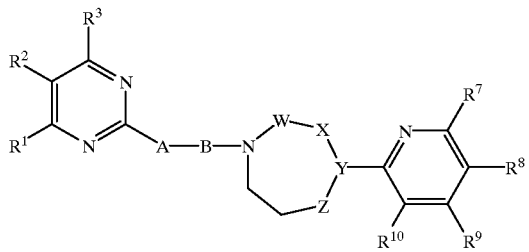

| Example No. | R1 | R2 | R3 | R7 | R8 | R9 | R10 | W | X—Y—Z | A | B |
|---|---|---|---|---|---|---|---|---|---|---|---|
| 101 | H | H | OH | tBut | H | tBut | H | CH$_2$ | CH$_2$—N—CH$_2$ | S | —(CH$_2$)$_3$— |
| 102 | H | H | OH | tBut | CN | H | H | CH$_2$ | CH$_2$—N—CH$_2$ | S | —(CH$_2$)$_3$— |
| 103 | Me | H | OH | tBut | H | Cl | H | CH$_2$ | CH$_2$—N—CH$_2$ | NH | —CH$_2$—C(=CH$_2$)—CH$_2$— |
| 104 | H | H | OH | H | CN | tBu | H | CH$_2$—CH$_2$ | CH$_2$—CH=C | —CH$_2$— | —CH$_2$—CH(CH$_3$)—CH$_2$— |
| 105 | H | H | NH$_2$ | CF$_3$ | H | tBut | H | CH$_2$ | CH$_2$—N—CH$_2$ | S | —(CH$_2$)$_3$— |
| 106 | H | H | OH | nProp | H | iProp | H | CH$_2$—CH$_2$ | CH=C—CH$_2$ | —CH$_2$— | —CH$_2$—CH(CH$_3$)—CH$_2$— |
| 107 | H | me | OH | H | H | iProp | OMe | CH$_2$—CH$_2$ | CH$_2$—CH=C | S | —(CH$_2$)$_3$— |
| 108 | H | H | OH | tBut | H | tBut | H | CH$_2$ | CH$_2$—N—CH$_2$ | NH | —CH$_2$—C(=CH$_2$)—CH$_2$— |
| 109 | H | H | OH | tBut | CN | H | H | CH$_2$—CH$_2$ | CH$_2$—N—CH$_2$ | S | —(CH$_2$)$_4$— |
| 110 | H | H | NH$_2$ | tBut | H | Cl | H | CH$_2$ | CH$_2$—N—CH$_2$ | O | —(CH$_2$)$_3$— |
| 111 | Me | H | OH | H | CN | tBu | H | CH$_2$ | CH=C—CH$_2$ | S | —CH$_2$—C(CH$_3$)=CH—CH$_2$— |
| 112 | H | H | OH | CF$_3$ | H | tBut | H | CH$_2$—CH$_2$ | CH$_2$—N—CH$_2$ | —CH$_2$— | —CH$_2$—C(=CH$_2$)—CH$_2$— |
| 113 | H | H | OH | nProp | H | iProp | H | CH$_2$ | CH$_2$—N—CH$_2$ | S | —(CH$_2$)$_3$— |
| 114 | H | H | NHMe | H | H | iProp | OMe | CH$_2$ | CH$_2$—N—CH$_2$ | S | —(CH$_2$)$_3$— |
| 115 | H | H | OH | nProp | CN | tBut | H | CH$_2$—CH$_2$ | CH$_2$—N—CH$_2$ | S | —(CH$_2$)$_4$— |
| 116 | H | H | OH | CF$_3$ | CN | iProp | H | CH$_2$—CH$_2$ | CH$_2$—CH=C | S | —(CH$_2$)$_3$— |
| 117 | Me | H | OH | Ph | C=CH | tBut | H | CH$_2$ | CH$_2$—N—CH$_2$ | NH | —CH$_2$—CH(CH$_3$)—CH$_2$— |
| 118 | H | H | OH | tBut | CN | tBut | H | CH$_2$—CH$_2$ | CH=C—CH$_2$ | —CH$_2$— | —CH$_2$—CH(CH$_3$)—CH$_2$— |
| 119 | H | H | NH$_2$ | tBut | H | nProp | H | CH$_2$ | CH$_2$—N—CH$_2$ | S | —(CH$_2$)$_3$— |
| 120 | H | H | OH | Ph | H | tBut | OMe | CH$_2$ | CH$_2$—CH=C | —CH$_2$— | —(CH$_2$)$_5$— |
| 121 | H | Me | OH | CF$_3$ | H | tBut | F | CH$_2$—CH$_2$ | CH=C—CH$_2$ | S | —CH$_2$—CH(CH$_3$)—CH$_2$— |
| 122 | H | H | OH | tBut | F | H | Me | CH$_2$ | CH$_2$—N—CH$_2$ | NH | —CH$_2$—CH=CH—CH$_2$— |

TABLE 5-continued

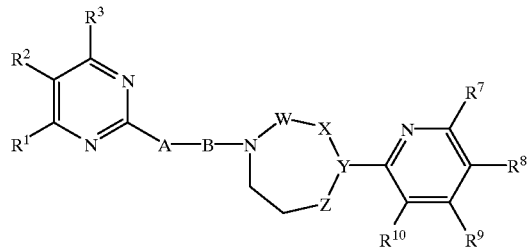

| Example No. | R1 | R2 | R3 | R7 | R8 | R9 | R10 | W | X—Y—Z | A | B |
|---|---|---|---|---|---|---|---|---|---|---|---|
| 123 | H | H | OH | nProp | CN | tBut | Me | CH$_2$—CH$_2$ | CH$_2$—CH=C | S | —CH$_2$—C(=CH$_2$)—CH$_2$— |
| 124 | H | H | NH$_2$ | nProp | C≡CH | tBut | H | CH$_2$ | CH=C—CH$_2$ | —CH$_2$— | —CH$_2$—C(CH$_3$)=CH—CH$_2$— |
| 125 | H | H | OH | tBut | CN | H | Me | CH$_2$ | CH$_2$—N—CH$_2$ | S | —(CH$_2$)$_4$— |

TABLE 6

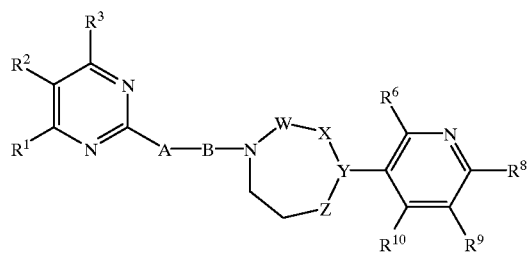

| Example No. | R1 | R2 | R3 | R6 | R8 | R9 | R10 | W | X—Y—Z | A | B |
|---|---|---|---|---|---|---|---|---|---|---|---|
| 126 | H | H | OH | OMe | H | tBut | H | CH$_2$ | CH$_2$—N—CH$_2$ | S | —(CH$_2$)$_3$— |
| 127 | H | H | OH | OMe | H | CF$_3$ | H | CH$_2$ | CH$_2$—N—CH$_2$ | S | —(CH$_2$)$_3$— |
| 128 | Me | H | OH | OMe | H | tBut | H | CH$_2$—CH$_2$ | CH$_2$—N—CH$_2$ | NH | —CH$_2$—C(=CH$_2$)—CH$_2$— |
| 129 | H | H | OH | H | CN | tBut | H | CH$_2$ | CH=C—CH$_2$ | —CH$_2$— | —CH$_2$—C(CH$_3$)=CH—CH$_2$— |
| 130 | H | H | NH$_2$ | H | F | tBut | H | CH$_2$ | CH$_2$—N—CH$_2$ | S | —(CH$_2$)$_3$— |
| 131 | H | H | OH | Me | Cl | iProp | H | CH$_2$ | CH$_2$—CH=C | —CH$_2$— | —CH$_2$—C(=CH$_2$)—CH$_2$— |
| 132 | H | Me | OH | H | H | iProp | H | CH$_2$—CH$_2$ | CH=C—CH$_2$ | S | —(CH$_2$)$_3$— |
| 133 | H | H | OH | H | H | tBut | OMe | CH$_2$—CH$_2$ | CH$_2$—N—CH$_2$ | NH | —CH$_2$—C(=CH$_2$)—CH$_2$— |
| 134 | H | H | OH | CN | H | CF$_3$ | H | CH$_2$—CH$_2$ | CH$_2$—N—CH$_2$ | S | —(CH$_2$)$_4$— |
| 135 | H | H | NH$_2$ | H | CN | H | OMe | CH | CH$_2$—N—CH$_2$ | O | —CH$_2$—CH(CH$_3$)—CH$_2$— |
| 136 | Me | H | OH | H | H | tBu | F | CH$_2$ | CH$_2$—CH=C | S | —CH$_2$—C(CH$_3$)=CH—CH$_2$— |
| 137 | H | H | OH | H | CN | tBut | H | CH$_2$—CH$_2$ | CH$_2$—N—CH$_2$ | —CH$_2$— | —(CH$_2$)$_3$— |
| 138 | H | H | OH | Me | H | iProp | H | CH$_2$ | CH$_2$—N—CH$_2$ | S | —(CH$_2$)$_3$— |
| 139 | H | H | NHMe | OMe | H | iProp | H | CH$_2$—CH$_2$ | CH$_2$—N—CH$_2$ | S | —CH$_2$—CH(CH$_3$)—CH$_2$— |
| 140 | H | H | OH | OMe | CN | tBut | H | CH$_2$ | CH=C—CH$_2$ | S | —(CH$_2$)$_3$— |
| 141 | H | H | OH | OMe | Me | tBut | H | CH$_2$ | CH$_2$—N—CH$_2$ | S | —(CH$_2$)$_3$— |
| 142 | Me | H | OH | H | CN | tBut | H | CH$_2$—CH$_2$ | CH$_2$—N—CH$_2$ | NH | —CH$_2$—CH=CH—CH$_2$— |
| 143 | H | H | OH | Me | H | tBut | H | CH$_2$ | CH$_2$—CH=C | —CH$_2$— | —CH$_2$—C(=CH$_2$)—CH$_2$— |
| 144 | H | H | NH$_2$ | H | Cl | CF$_3$ | Me | CH$_2$—CH$_2$ | CH$_2$—N—CH$_2$ | S | —(CH$_2$)$_3$— |
| 145 | H | H | OH | OMe | CN | tBut | Me | CH$_2$ | CH=C—CH$_2$ | —CH$_2$— | —CH$_2$—CH(CH$_3$)—CH$_2$— |
| 146 | H | me | OH | Me | Me | iProp | Me | CH$_2$ | CH$_2$—CH=C | S | —(CH$_2$)$_3$— |

TABLE 7

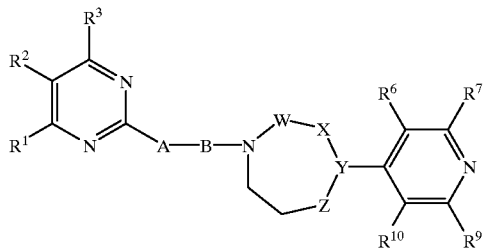

| Example No. | R1 | R2 | R3 | R6 | R7 | R9 | R10 | W | X—Y—Z | A | B |
|---|---|---|---|---|---|---|---|---|---|---|---|
| 147 | H | H | OH | H | tBut | tBut | H | $CH_2$ | $CH_2$—N—$CH_2$ | S | —$(CH_2)_3$— |
| 148 | H | H | OH | H | tBut | Ph | H | $CH_2$ | $CH_2$—N—$CH_2$ | S | —$(CH_2)_3$— |
| 149 | Me | H | OH | H | tBut | 1-Pyrrolyl | H | $CH_2$ | $CH_2$—N—$CH_2$ | NH | —$CH_2$—C(=$CH_2$)—$CH_2$— |
| 150 | H | H | OH | H | nPropyl | tBut | H | $CH_2$—$CH_2$ | $CH_2$—CH=C | —$CH_2$— | —$CH_2$—C($CH_3$)=CH—$CH_2$— |
| 151 | H | H | $NH_2$ | H | $CF_3$ | tBut | H | $CH_2$ | $CH_2$—N—$CH_2$ | S | —$(CH_2)_3$— |
| 152 | H | H | OH | H | 2-Napht | tBut | H | $CH_2$—$CH_2$ | CH=C—$CH_2$ | —$CH_2$— | —$CH_2$—C(=$CH_2$)—$CH_2$— |
| 153 | H | Me | OH | OMe | tBut | H | H | $CH_2$—$CH_2$ | $CH_2$—CH=C | S | —$(CH_2)_3$— |
| 154 | H | H | OH | OMe | iProp | H | H | $CH_2$ | $CH_2$—N—$CH_2$ | NH | —$CH_2$—C(=$CH_2$)—$CH_2$— |
| 155 | H | H | OH | OMe | H | $CF_3$ | H | $CH_2$—$CH_2$ | $CH_2$—N—$CH_2$ | S | —$(CH_2)_4$— |
| 156 | H | H | $NH_2$ | H | tBut | H | H | $CH_2$ | $CH_2$—N—$CH_2$ | O | —$CH_2$—CH($CH_3$)—$CH_2$— |
| 157 | Me | H | OH | H | iProp | H | Me | $CH_2$ | CH=C—$CH_2$ | S | —$CH_2$—C($CH_3$)=CH—$CH_2$— |
| 158 | H | H | OH | CN | tBut | H | H | $CH_2$—$CH_2$ | $CH_2$—N—$CH_2$ | —$CH_2$— | —$(CH_2)_3$— |
| 159 | H | H | OH | H | H | $CF_3$ | Me | $CH_2$ | $CH_2$—N—$CH_2$ | S | —$(CH_2)_3$— |
| 160 | H | H | NHMe | H | nProp | tBut | H | $CH_2$ | $CH_2$—N—$CH_2$ | S | —$CH_2$—CH($CH_3$)—$CH_2$— |
| 161 | H | H | OH | OMe | tBut | iProp | H | $CH_2$—$CH_2$ | $CH_2$—N—$CH_2$ | S | —$(CH_2)_3$— |
| 162 | H | H | OH | OMe | $CF_3$ | tBut | H | $CH_2$—$CH_2$ | CH=C—$CH_2$ | NH | —$(CH_2)_3$— |
| 163 | Me | H | OH | Me | tBut | nProp | H | $CH_2$ | $CH_2$—CH=C | —$CH_2$— | —$CH_2$—CH=CH—$CH_2$— |
| 164 | H | H | OH | Me | tBut | H | H | $CH_2$—$CH_2$ | $CH_2$—N—$CH_2$ | S | —$CH_2$—(=$CH_2$)—$CH_2$— |
| 165 | H | H | $NH_2$ | H | tBut | tBut | H | $CH_2$ | CH=C—$CH_2$ | —$CH_2$— | —$(CH_2)_3$— |
| 166 | H | H | OH | Me | $CF_3$ | tBut | H | $CH_2$ | $CH_2$—CH=C | S | —$CH_2$—CH($CH_3$)—$CH_2$— |

TABLE 8

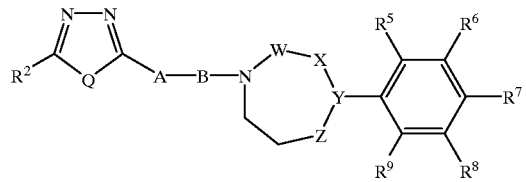

| Example No. | Q | R2 | R5 | R6 | R7 | R8 | R9 | W | X—Y—Z | A | B |
|---|---|---|---|---|---|---|---|---|---|---|---|
| 167 | $NCH_3$ | $NH_2$ | H | tBut | H | Me | H | $CH_2$ | $CH_2$—N—$CH_2$ | S | —$(CH_2)_3$— |
| 168 | S | $NH_2$ | H | tBut | H | Ph | H | $CH_2$ | $CH_2$—N—$CH_2$ | S | —$(CH_2)_3$— |
| 169 | $NCH_3$ | $NH_2$ | H | tBut | H | 1-PYrrolyl | H | $CH_2$—$CH_2$ | $CH_2$—N—$CH_2$ | NH | —$(CH_2)_3$— |
| 170 | $NCH_3$ | $NH_2$ | H | iProp | H | 2-Napht | H | $CH_2$ | $CH_2$—CH=C | —$CH_2$— | —$(CH_2)_3$— |
| 171 | S | $NH_2$ | H | Et | H | tBut | H | $CH_2$—$CH_2$ | $CH_2$—N—$CH_2$ | S | —$(CH_2)_3$— |
| 172 | S | $NH_2$ | H | $CHF_2$ | H | H | H | $CH_2$ | CH=C—$CH_2$ | —$CH_2$— | —$(CH_2)_8$— |
| 173 | $NCH_3$ | $NH_2$ | H | $CHF_2$ | H | tBut | H | $CH_2$ | $CH_2$—CH=C | S | —$(CH_2)_{10}$— |
| 174 | $NCH_3$ | $NH_2$ | H | $CF_3$ | H | tBut | H | $CH_2$ | $CH_2$—N—$CH_2$ | NH | —$(CH_2)_3$— |
| 175 | $NCH_3$ | $NH_2$ | H | iProp | F | H | H | $CH_2$—$CH_2$ | $CH_2$—N—$CH_2$ | S | —$(CH_2)_3$— |
| 176 | $NCH_3$ | $NH_2$ | H | H | CN | tBut | H | $CH_2$ | $CH_2$—CH=C | O | —$(CH_2)_3$— |
| 177 | S | $NH_2$ | H | H | F | tBut | H | $CH_2$—$CH_2$ | CH=C—$CH_2$ | S | —$(CH_2)_3$— |
| 178 | $NCH_3$ | $NH_2$ | H | H | Cl | iProp | H | $CH_2$—$CH_2$ | $CH_2$—N—$CH_2$ | —$CH_2$— | —$(CH_2)_3$— |
| 179 | $NCH_3$ | $NH_2$ | H | tBut | H | H | OMe | $CH_2$ | CH=C—$CH_2$ | S | —$(CH_2)_3$— |
| 180 | S | $NH_2$ | H | nProp | CN | tBut | H | $CH_2$—$CH_2$ | $CH_2$—CH=C | —$CH_2$— | —$(CH_2)_3$— |
| 181 | $NCH_3$ | $NH_2$ | H | $CF_3$ | CN | iProp | H | $CH_2$ | $CH_2$—N—$CH_2$ | S | —$(CH_2)_3$— |
| 182 | $NCH_3$ | $NH_2$ | H | Ph | C=CH | tBut | H | $CH_2$ | CH=C—$CH_2$ | —$CH_2$— | —$(CH_2)_3$— |
| 183 | $NCH_3$ | $NH_2$ | OMe | tBut | CN | H | H | $CH_2$ | $CH_2$—CH=C | S | —$(CH_2)_3$— |
| 184 | $NCH_3$ | $NH_2$ | OMe | tBut | CN | H | H | $CH_2$ | $CH_2$—CH=C | S | —$(CH_2)_3$— |
| 185 | S | $NH_2$ | H | tBut | CN | $CF_3$ | OMe | $CH_2$—$CH_2$ | $CH_2$—N—$CH_2$ | NH | —$(CH_2)_3$— |
| 186 | $NCH_3$ | $NH_2$ | Me | tBut | F | H | H | $CH_2$—$CH_2$ | $CH_2$—CH=C | S | —$(CH_2)_3$— |
| 187 | S | $NH_2$ | H | iProp | H | H | OMe | $CH_2$ | $CH_2$—N—$CH_2$ | S | —$(CH_2)_3$— |
| 188 | N(iProp) | $NH_2$ | H | tBut | H | Me | H | $CH_2$ | $CH_2$—N—$CH_2$ | S | —$(CH_2)_3$— |
| 189 | N(iProp) | $NH_2$ | H | tBut | H | Ph | H | $CH_2$—$CH_2$ | $CH_2$—N—$CH_2$ | NH | —$(CH_2)_4$— |
| 190 | S | $NH_2$ | H | tBut | H | 1-Pyrrolyl | H | $CH_2$ | CH=C—$CH_2$ | S | —$(CH_2)_3$— |
| 191 | N(iProp) | $NH_2$ | H | iProp | H | 2-Napht | H | $CH_2$—$CH_2$ | $CH_2$—N—$CH_2$ | —$CH_2$— | —$(CH_2)_3$— |

TABLE 8-continued

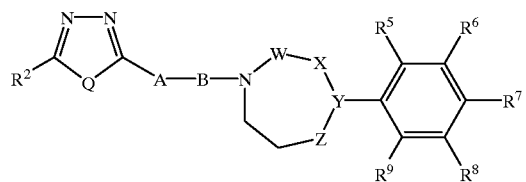

| Example No. | Q | R2 | R5 | R6 | R7 | R8 | R9 | W | X—Y—Z | A | B |
|---|---|---|---|---|---|---|---|---|---|---|---|
| 192 | S | NH$_2$ | H | Et | H | tBut | H | CH$_2$ | CH$_2$—N—CH$_2$ | S | —(CH$_2$)$_{10}$— |
| 193 | N(iProp) | NH$_2$ | H | CF$_3$ | H | tBut | H | CH$_2$—CH$_2$ | CH$_2$—N—CH$_2$ | —CH$_2$— | —(CH$_2$)$_4$— |
| 194 | N(iProp) | NH$_2$ | H | H | CN | tBut | H | CH$_2$—CH$_2$ | CH=C—CH$_2$ | NH | —(CH$_2$)$_3$— |
| 195 | N(iProp) | NH$_2$ | H | H | F | tBut | H | CH$_2$ | CH$_2$—N—CH$_2$ | S | —(CH$_2$)$_3$— |
| 196 | N(iProp) | NH$_2$ | H | H | Cl | iProp | H | CH$_2$ | CH=C—CH$_2$ | —CH$_2$— | —(CH$_2$)$_3$— |
| 197 | S | NH$_2$ | H | tBut | H | H | OMe | CH$_2$—CH$_2$ | CH$_2$—N—CH$_2$ | S | —(CH$_2$)$_8$— |
| 198 | N(iProp) | NH$_2$ | H | nProp | CN | tBut | H | CH$_2$ | CH$_2$—CH=C | —CH$_2$— | —(CH$_2$)$_3$— |
| 199 | S | NH$_2$ | H | CF$_3$ | CN | iProp | H | CH$_2$ | CH$_2$—N—CH$_2$ | S | —(CH$_2$)$_4$— |
| 200 | N(iProp) | NH$_2$ | H | Ph | C=CH | tBut | H | CH$_2$—CH$_2$ | CH=C—CH$_2$ | —CH$_2$— | —(CH$_2$)$_3$— |
| 201 | N(iProp) | NH$_2$ | H | tBut | CN | CF$_3$ | OMe | CH$_2$ | CH$_2$—N—CH$_2$ | NH | —(CH$_2$)$_3$— |
| 202 | N(iProp) | NH$_2$ | H | Ph | CN | tBut | Me | CH$_2$—CH$_2$ | CH$_2$—N—CH$_2$ | O | —(CH$_2$)$_3$— |
| 203 | S | NH$_2$ | H | iProp | H | H | OMe | CH$_2$—CH$_2$ | CH$_2$—N—CH$_2$ | S | —(CH$_2$)$_8$— |
| 204 | N(iProp) | NHMe | H | tBut | H | Me | H | CH$_2$ | CH$_2$—N—CH$_2$ | S | —CH$_2$—C(=CH$_2$)—CH$_2$— |
| 205 | N(iProp) | NHMe | H | tBut | H | Ph | H | CH$_2$ | CH$_2$—CH=C | —CH$_2$— | —CH$_2$—C(=CH$_2$)—CH$_2$— |
| 206 | S | NHMe | H | tBut | H | 1-Pyrrolyl | H | CH$_2$—CH$_2$ | CH=C—CH$_2$ | S | —CH$_2$—CH=CH—CH$_2$— |
| 207 | N(iProp) | NHMe | H | iProp | H | 2-Napht | H | CH$_2$—CH$_2$ | CH$_2$—N—CH$_2$ | NH | —CH$_2$—CH(CH$_3$)—CH$_2$— |
| 208 | N(iProp) | NHMe | H | Et | H | tBut | H | CH$_2$—CH$_2$ | CH$_2$—N—CH$_2$ | S | —CH$_2$—CH(CH$_3$)—CH$_2$— |
| 209 | N(iProp) | OH | H | tBut | H | Cl | H | CH$_2$—CH$_2$ | CH$_2$—N—CH$_2$ | —CH$_2$— | —CH$_2$—CH(CH$_3$)—CH$_2$— |
| 210 | N(iProp) | OH | H | CF$_3$ | H | Cl | H | CH$_2$ | CH=C—CH$_2$ | NH | —CH$_2$—CH(CH$_3$)—CH$_2$— |
| 211 | N(iProp) | OH | H | CF$_3$ | H | tBut | H | CH$_2$—CH$_2$ | CH$_2$—N—CH$_2$ | S | —CH$_2$—C(=CH$_2$)—CH$_2$— |
| 212 | S | OH | H | iProp | CN | F | H | CH$_2$—CH$_2$ | CH=C—CH$_2$ | —CH$_2$— | —CH$_2$—C(=CH$_2$)—CH$_2$— |
| 213 | N(iProp) | OMe | H | H | CN | tBut | H | CH$_2$ | CH$_2$—CH=C | —CH$_2$— | —CH$_2$—C(=CH$_2$)—CH$_2$— |
| 214 | N(iProp) | OMe | H | H | F | tBut | H | CH$_2$ | CH$_2$—CH=C | S | —CH$_2$—C(CH$_3$)=CH—CH$_2$— |
| 215 | S | OMe | H | H | Cl | iProp | H | CH$_2$ | CH=C—CH$_2$ | O | —CH$_2$—CH(CH$_3$)—CH$_2$— |
| 216 | N(iProp) | OMe | H | tBut | H | H | OMe | CH$_2$—CH$_2$ | CH=C—CH$_2$ | NH | —CH$_2$—C(CH$_3$)=CH—CH$_2$— |
| 217 | N(iProp) | NHMe | H | nProp | CN | tBut | H | CH$_2$ | CH$_2$—N—CH$_2$ | NH | —CH$_2$—CH(CH$_3$)—CH$_2$— |
| 218 | S | NHMe | H | CF$_3$ | CN | iProp | H | CH$_2$—CH$_2$ | CH$_2$—N—CH$_2$ | S | —CH$_2$—C(CH$_3$)=CH—CH$_2$— |
| 219 | N(iProp) | OH | H | Ph | C=CH | tBut | H | CH$_2$—CH$_2$ | CH$_2$—N—CH$_2$ | —CH$_2$— | —CH$_2$—C(CH$_3$)=CH—CH$_2$— |
| 220 | N(iProp) | OH | OMe | tBut | CN | H | H | CH$_2$ | CH$_2$—CH=C | NH | —CH$_2$—CH(CH$_3$)—CH$_2$— |
| 221 | N(iProp) | OH | H | tBut | CN | CF$_3$ | OMe | CH$_2$ | CH$_2$—N—CH$_2$ | S | —CH$_2$—C(=CH$_2$)—CH$_2$— |
| 222 | S | OH | H | nProp | F | tBut | H | CH$_2$—CH$_2$ | CH=C—CH$_2$ | —CH$_2$— | —CH$_2$—C(=CH$_2$)—CH$_2$— |
| 223 | S | OMe | H | Ph | CN | tBut | Me | CH$_2$ | CH$_2$—CH=C | —CH$_2$— | —CH$_2$—C(=CH$_2$)—CH$_2$— |
| 224 | N(iProp) | OMe | OMe | tBut | F | H | H | CH$_2$ | CH=C—CH$_2$ | S | —CH$_2$—CH(CH$_3$)—CH$_2$— |
| 225 | N(iProp) | OMe | H | iProp | H | H | OMe | CH$_2$ | CH$_2$—CH=C | S | —CH$_2$—C(CH$_3$)=CH—CH$_2$— |

TABLE 9

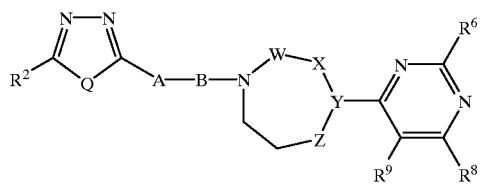

| Example No. | Q | R2 | R6 | R8 | R9 | W | X—Y—Z | A | B |
|---|---|---|---|---|---|---|---|---|---|
| 226 | NCH$_3$ | NH$_2$ | tBut | Ph | H | CH$_2$ | CH$_2$—N—CH$_2$ | —CH$_2$— | —(CH$_2$)$_3$— |
| 227 | NCH$_3$ | NH$_2$ | tBut | 2-Napht | H | CH$_2$ | CH$_2$—N—CH$_2$ | S | —CH$_2$—C(=CH$_2$)—CH$_2$— |
| 228 | NCH$_3$ | NH$_2$ | tBut | 1-Pyrrolyl | H | CH$_2$—CH$_2$ | CH$_2$—N—CH$_2$ | S | —(CH$_2$)$_3$— |
| 229 | NCH$_3$ | NHMe | tBut | cHex | H | CH$_2$—CH$_2$ | CH$_2$—CH=C | —CH$_2$— | —(CH$_2$)$_3$— |
| 230 | NCH$_3$ | NH$_2$ | tBut | nHex | H | CH$_2$ | CH$_2$—N—CH$_2$ | S | —(CH$_2$)$_5$— |
| 231 | S | NH$_2$ | tBut | Ph | H | CH$_2$ | CH$_2$—N—CH$_2$ | —CH$_2$— | —(CH$_2$)$_8$— |
| 232 | S | NHMe | iProp | 1-Pyrrolyl | H | CH$_2$ | CH$_2$—N—CH$_2$ | S | —CH$_2$—CH(CH$_3$)—CH$_2$— |
| 233 | S | NH$_2$ | CH$_3$ | CH$_3$ | H | CH$_2$—CH$_2$ | CH$_2$—CH=C | NH | —(CH$_2$)$_3$— |
| 234 | NCH$_3$ | NH$_2$ | H | CHF$_2$ | H | CH$_2$ | CH$_2$—N—CH$_2$ | O | —CH$_2$—C(=CH$_2$)—CH$_2$— |
| 235 | S | NH$_2$ | tBut | tBut | H | CH$_2$ | CH$_2$—N—CH$_2$ | —CH$_2$— | —(CH$_2$)$_{10}$— |
| 236 | S | NHMe | tBut | iProp | H | CH$_2$—CH$_2$ | CH$_2$—N—CH$_2$ | S | —CH$_2$—C(CH$_3$)=CH—CH$_2$— |
| 237 | NCH$_3$ | NH$_2$ | tBut | tBut | H | CH$_2$ | CH$_2$—N—CH$_2$ | S | —CH$_2$—C(=CH$_2$)—CH$_2$— |
| 238 | NCH$_3$ | NH$_2$ | 2-Napht | tBut | Me | CH$_2$—CH$_2$ | CH=C—CH$_2$ | —CH$_2$— | —CH$_2$—CH(CH$_3$)—CH$_2$— |
| 239 | S | NH$_2$ | tBut | CF$_3$ | H | CH$_2$—CH$_2$ | CH$_2$—CH=C | S | —(CH$_2$)$_8$— |
| 240 | NCH$_3$ | NH$_2$ | tBut | H | CH$_3$ | CH$_2$ | CH$_2$—N—CH$_2$ | S | —(CH$_2$)$_3$— |

TABLE 9-continued

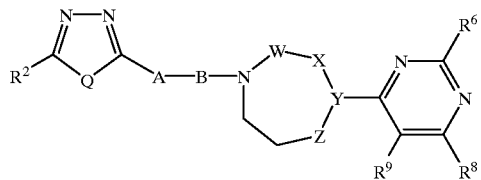

| Example No. | Q | R2 | R6 | R8 | R9 | W | X—Y—Z | A | B |
|---|---|---|---|---|---|---|---|---|---|
| 241 | N(iProp) | NH$_2$ | tBut | Ph | H | CH$_2$—CH$_2$ | CH=C—CH$_2$ | S | —CH$_2$—(=CH$_2$)—CH$_2$— |
| 242 | N(iProp) | NH$_2$ | tBut | 2-Napht | H | CH$_2$ | CH$_2$—CH=C | NH | —(CH$_2$)$_3$— |
| 243 | N(iProp) | NH$_2$ | tBut | 1-Pyrrolyl | H | CH$_2$ | CH$_2$—N—CH$_2$ | O | —CH$_2$—CH(CH$_3$)—CH$_2$— |
| 244 | N(iProp) | NH$_2$ | tBut | cHex | H | CH$_2$—CH$_2$ | CH$_2$—N—CH$_2$ | —CH$_2$— | —(CH$_2$)$_3$— |
| 245 | S | NH$_2$ | tBut | tBut | H | CH$_2$ | CH$_2$—N—CH$_2$ | S | —CH$_2$—C(=CH$_2$)—CH$_2$— |
| 246 | S | OH | tBut | F | H | CH$_2$—CH$_2$ | CH=C—CH$_2$ | S | —(CH$_2$)$_{10}$— |
| 247 | N(nProp) | OMe | iProp | tBut | H | CH$_2$ | CH$_2$—N—CH$_2$ | —CH$_2$— | —CH$_2$—CH=CH—CH$_2$— |
| 248 | N(nProp) | OMe | CH$_3$ | 1-Pyrrolyl | H | CH$_2$ | CH$_2$—N—CH$_2$ | —CH$_2$— | —(CH$_2$)$_3$— |
| 249 | N(nProp) | NCH$_2$Ph | H | iProp | H | CH$_2$—CH$_2$ | CH$_2$—N—CH$_2$ | S | —CH$_2$—CH=CH—CH$_2$— |
| 250 | N(iProp) | OH | tBut | tBut | H | CH$_2$ | CH=C—CH$_2$ | —CH$_2$— | —(CH$_2$)$_4$— |
| 251 | N(iProp) | OH | tBut | iProp | F | CH$_2$—CH$_2$ | CH$_2$—N—CH$_2$ | S | —CH$_2$—CH=CH—CH$_2$— |
| 252 | N(iProp) | OMe | Ph | tBut | Cl | CH$_2$ | CH$_2$—N—CH$_2$ | S | —(CH$_2$)$_5$— |
| 253 | N(nProp) | OMe | 2-Napht | tBut | Me | CH$_2$ | CH=C—CH$_2$ | —CH$_2$— | —(CH$_2$)$_3$— |
| 254 | N(nProp) | NCH$_2$Ph | tBut | CF$_3$ | OMe | CH$_2$—CH$_2$ | CH$_2$—N—CH$_2$ | S | —(CH$_2$)$_4$— |
| 255 | N(nProp) | NHMe | tBut | H | CH$_3$ | CH$_2$ | CH=C—CH$_2$ | S | —CH$_2$—CH(CH$_3$)—CH$_2$— |

TABLE 10

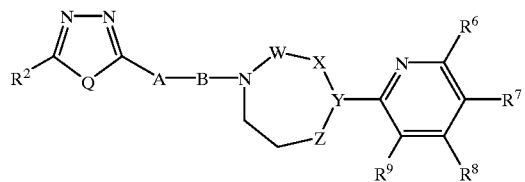

| Example No. | Q | R2 | R6 | R7 | R8 | R9 | W | X—Y—Z | A | B |
|---|---|---|---|---|---|---|---|---|---|---|
| 256 | NCH$_3$ | NH$_2$ | tBut | H | tBut | H | CH$_2$ | CH$_2$—N—CH$_2$ | S | —(CH$_2$)$_3$— |
| 257 | S | OH | tBut | CN | H | H | CH$_2$ | CH$_2$—N—CH$_2$ | S | —(CH$_2$)$_8$— |
| 258 | N(iProp) | NHMe | tBut | H | Cl | H | CH$_2$ | CH$_2$—N—CH$_2$ | NH | —CH$_2$—C(=CH$_2$)—CH$_2$— |
| 259 | NCH$_3$ | NH$_2$ | H | CN | tBu | H | CH$_2$ | CH$_2$—CH=C | —CH$_2$— | —CH$_2$CH(CH$_3$)—CH$_2$— |
| 260 | NCH$_3$ | NHMe | CF$_3$ | H | tBut | H | CH$_2$—CH$_2$ | CH$_2$—N—CH$_2$ | S | —(CH$_2$)$_3$— |
| 261 | N(cProp) | NH$_2$ | nProp | H | iProp | H | CH$_2$—CH$_2$ | CH=C—CH$_2$ | —CH$_2$— | —CH$_2$—C(=CH$_2$)—CH$_2$— |
| 262 | S | NHMe | H | H | iProp | H | CH$_2$ | CH$_2$—CH=C | S | —(CH$_2$)$_{10}$— |
| 263 | NCH$_3$ | NH$_2$ | tBut | H | tBut | H | CH$_2$—CH$_2$ | CH$_2$—N—CH$_2$ | NH | —CH$_2$—C(=CH$_2$)—CH$_2$13 |
| 264 | N(iProp) | NH$_2$ | tBut | CN | H | H | CH$_2$—CH$_2$ | CH$_2$—N—CH$_2$ | S | —(CH$_2$)$_4$— |
| 265 | NOH | NHMe | tBut | H | H | OMe | CH$_2$ | CH$_2$—CH=C | O | —(CH$_2$)$_3$— |
| 266 | NCH$_3$ | OH | H | CN | tBu | H | CH$_2$ | CH=C—CH$_2$ | S | —CH$_2$—CH(CH$_3$)—CH$_2$— |
| 267 | NEt | NH$_2$ | CF$_3$ | H | tBut | H | CH$_2$—CH$_2$ | CH$_2$—N—CH$_2$ | —CH$_2$— | —CH$_2$—CH(CH$_3$)—CH$_2$— |
| 268 | S | NH$_2$ | nProp | H | iProp | H | CH$_2$ | CH$_2$—N—CH$_2$ | S | —CH$_2$—C(=CH$_2$)—CH$_2$— |
| 269 | NCH$_3$ | NH$_2$ | nProp | CN | tBut | H | CH$_2$ | CH$_2$—N—CH$_2$ | S | —(CH$_2$)$_4$— |
| 270 | NCH$_3$ | OH | CF$_3$ | CN | iProp | H | CH$_2$—CH$_2$ | CH=C—CH$_2$ | S | —(CH$_2$)$_3$— |
| 271 | N(iProp) | NHMe | Ph | C=CH | tBut | H | CH$_2$ | CH$_2$—N—CH$_2$ | NH | —CH$_2$—C(=CH$_2$)—CH$_2$— |
| 272 | S | NH$_2$ | tBut | CN | tBut | H | CH$_2$—CH$_2$ | CH$_2$—CH=C | —CH$_2$— | —CH$_2$—CH(CH$_3$)—CH$_2$— |
| 273 | NCH$_3$ | NHMe | tBut | H | nProp | OMe | CH$_2$ | CH$_2$—N—CH$_2$ | S | —(CH$_2$)$_3$— |
| 274 | N(cProp) | NH$_2$ | Ph | H | tBut | H | CH$_2$ | CH=C—CH$_2$ | —CH$_2$— | —(CH$_2$)$_4$— |
| 275 | S | NHMe | CF$_3$ | H | tBut | H | CH$_2$—CH$_2$ | CH$_2$—CH=C | S | —(CH$_2$)$_3$— |
| 276 | NCH$_3$ | NH$_2$ | tBut | F | H | Me | CH$_2$ | CH$_2$—N—CH$_2$ | NH | —CH$_2$—CH=CH—CH$_2$— |
| 277 | S | NH$_2$ | nProp | CN | tBut | Me | CH$_2$—CH$_2$ | CH=C—CH$_2$ | S | —CH$_2$—C(=CH$_2$)—CH$_2$— |
| 278 | NCH$_3$ | OH | nProp | C=CH | tBut | OMe | CH$_2$ | CH=C—CH$_2$ | —CH$_2$— | —CH$_2$—C(CH$_3$)=CH—CH$_2$— |
| 279 | N(iProp) | OMe | tBut | CN | H | H | CH$_2$ | CH$_2$—N—CH$_2$ | S | —(CH$_2$)$_4$— |
| 280 | NCH$_3$ | OMe | H | H | iProp | H | CH$_2$—CH$_2$ | CH$_2$—N—CH$_2$ | S | —(CH$_2$)$_3$— |

TABLE 11

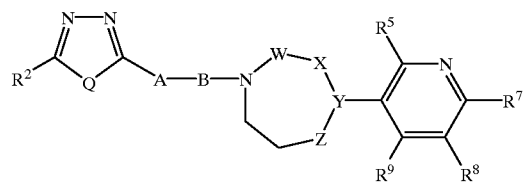

| Example No. | Q | R2 | R5 | R7 | R8 | R9 | W | X—Y—Z | A | B |
|---|---|---|---|---|---|---|---|---|---|---|
| 281 | NCH$_3$ | NH$_2$ | H | CN | tBut | H | CH$_2$ | CH=C—CH$_2$— | —CH$_2$— | —CH$_2$—C(=CH$_2$)—CH$_2$— |
| 282 | NCH$_3$ | NHMe | H | F | tBut | H | CH$_2$ | CH$_2$—N—CH$_2$ | S | —(CH$_2$)$_3$— |
| 283 | N(cProp) | NH$_2$ | Me | Cl | iProp | H | CH$_2$ | CH$_2$—CH=C | —CH$_2$— | —(CH$_2$)$_3$— |
| 284 | S | NHMe | H | H | iProp | H | CH$_2$—CH$_2$ | CH=C—CH$_2$— | S | —(CH$_2$)$_{10}$— |
| 285 | NCH$_3$ | NH$_2$ | H | H | tBut | OMe | CH$_2$—CH$_2$ | CH$_2$—N—CH$_2$ | NH | —CH$_2$—CH(CH$_3$)—CH$_2$— |
| 286 | N(iProp) | NH$_2$ | CN | H | CF$_3$ | H | CH$_2$ | CH$_2$—N—CH$_2$ | S | —(CH$_2$)$_4$— |
| 287 | S | NHMe | H | CN | tBut | H | CH$_2$ | CH$_2$—N—CH$_2$ | O | —(CH$_2$)$_8$— |
| 288 | S | OH | H | H | tBu | H | CH$_2$—CH$_2$ | CH=C—CH$_2$ | S | —CH$_2$—C(=CH$_2$)—CH$_2$— |
| 289 | NEt | NH$_2$ | H | CN | CHF$_2$ | H | CH$_2$ | CH$_2$—N—CH$_2$ | —CH$_2$— | —(CH$_2$)$_3$— |
| 290 | NCH$_3$ | NH$_2$ | Me | H | iProp | H | CH$_2$ | CH$_2$—CH=C | S | —(CH$_2$)$_3$— |
| 291 | N(iProp) | NH$_2$ | F | CN | tBut | H | CH$_2$—CH$_2$ | CH$_2$—N—CH$_2$ | S | —(CH$_2$)$_4$— |
| 292 | S | NH$_2$ | OMe | Me | tBut | H | CH$_2$ | CH$_2$—N—CH$_2$ | S | —(CH$_2$)$_{10}$— |
| 293 | NCH$_3$ | NHMe | H | CN | tBut | F | CH$_2$—CH$_2$ | CH$_2$—N—CH$_2$ | NH | —CH$_2$—CH(CH$_3$)—CH$_2$— |
| 294 | NCH$_3$ | NH$_2$ | H | C≡CH | tBut | H | CH$_2$—CH$_2$ | CH=C—CH$_2$ | —CH$_2$— | —CH$_2$—C(CH$_3$)=CH—CH$_2$— |
| 295 | N(iProp) | NH$_2$ | H | Cl | CF$_3$ | Me | CH$_2$ | CH$_2$—N—CH$_2$ | S | —(CH$_2$)$_5$— |
| 296 | NEt | NHMe | H | CN | tBut | Me | CH$_2$—CH$_2$ | CH$_2$—CH=C | —CH$_2$— | —CH$_2$—C(=CH$_2$)—CH$_2$— |
| 297 | S | OH | H | C≡CH | iProp | Me | CH$_2$ | CH$_2$—CH=C | S | —(CH$_2$)$_8$— |
| 298 | NCH$_3$ | OH | Cl | H | iProp | H | CH$_2$ | CH$_2$—N—CH$_2$ | S | —(CH$_2$)$_3$— |

TABLE 12

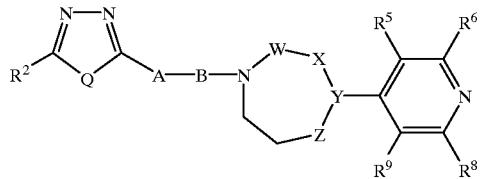

| Example No. | Q | R2 | R5 | R6 | R8 | R9 | W | X—Y—Z | A | B |
|---|---|---|---|---|---|---|---|---|---|---|
| 299 | NCH$_3$ | NH$_2$ | H | tBut | tBut | H | CH$_2$ | CH$_2$—N—CH$_2$ | S | —(CH$_2$)$_3$— |
| 300 | S | OH | H | tBut | Ph | H | CH$_2$ | CH$_2$—N—CH$_2$ | S | —CH$_2$—C(=CH$_2$)—CH$_2$— |
| 301 | N(iProp) | NHMe | H | tBut | 1-Pyrrolyl | H | CH$_2$ | CH$_2$—N—CH$_2$ | NH | —CH$_2$—CH=CH—CH$_2$— |
| 302 | NCH$_3$ | NH$_2$ | H | nPropyl | tBut | H | CH$_2$—CH$_2$ | CH=C—CH$_2$ | —CH$_2$— | —CH$_2$—CH(CH$_3$)—CH$_2$— |
| 303 | NCH$_3$ | NH$_2$ | H | CF$_3$ | tBut | H | CH$_2$ | CH$_2$—N—CH$_2$ | S | —(CH$_2$)$_3$— |
| 304 | N(cProp) | NH$_2$ | H | 2-Napht | tBut | H | CH$_2$—CH$_2$ | CH=C—CH$_2$ | —CH$_2$— | —(CH$_2$)$_3$— |
| 305 | S | NHMe | H | tBut | H | H | CH$_2$—CH$_2$ | CH$_2$—CH=C | S | —(CH$_2$)$_8$— |
| 306 | NCH$_3$ | NH$_2$ | H | iProp | CHF$_2$ | H | CH$_2$ | CH$_2$—N—CH$_2$ | NH | —CH$_2$—C(=CH$_2$)—CH$_2$— |
| 307 | N(iProp) | NH$_2$ | OMe | H | CF$_3$ | H | CH$_2$ | CH$_2$—N—CH$_2$ | S | —(CH$_2$)$_4$— |
| 308 | NOH | NHMe | H | tBut | H | F | CH$_2$—CH$_2$ | CH$_2$—CH=C | O | —(CH$_2$)$_3$— |
| 309 | NCH$_3$ | OH | H | iProp | H | Me | CH$_2$ | CH=C—CH$_2$ | S | —CH$_2$—C(CH$_3$)=CH—CH$_2$— |
| 310 | NEt | NH$_2$ | CN | tBut | H | H | CH$_2$ | CH$_2$—N—CH$_2$ | —CH$_2$— | —(CH$_2$)$_3$— |
| 311 | NCH$_3$ | NH$_2$ | H | H | CF$_3$ | Me | CH$_2$ | CH$_2$—N—CH$_2$ | S | —(CH$_2$)$_3$— |
| 312 | S | NHMe | H | 1-Pyrrolyl | H | H | CH$_2$—CH$_2$ | CH$_2$—N—CH$_2$ | S | —(CH$_2$)$_{10}$— |
| 313 | NCH$_3$ | OH | H | CF$_3$ | tBut | H | CH$_2$ | CH=C—CH$_2$ | NH | —CH$_2$—C(=CH$_2$)—CH$_2$— |
| 314 | NEt | NH$_2$ | Me | tBut | nProp | H | CH$_2$—CH$_2$ | CH$_2$—CH=C | —CH$_2$— | —CH$_2$—CH(CH$_3$)—CH$_2$— |
| 315 | NCH$_3$ | NH$_2$ | Me | tBut | H | H | CH$_2$ | CH$_2$—N—CH$_2$ | S | —(CH$_2$)$_5$— |
| 316 | | NH$_2$ | H | tBut | tBut | H | CH$_2$ | CH=C—CH$_2$ | —CH$_2$— | —CH$_2$—CH(CH$_3$)—CH$_2$— |
| 317 | N(iProp) | NH$_2$ | Me | CF$_3$ | tBut | H | CH$_2$—CH$_2$ | CH$_2$—CH=C | S | —(CH$_2$)$_4$— |
| 318 | NCH$_3$ | OH | H | nProp | tBut | H | CH$_2$ | CH$_2$—N—CH$_2$ | S | —(CH$_2$)$_3$— |

TABLE 13

| Example No. | R1 | R2 | R3 | R6 | R7 | R8 | R9 | R10 | W | X—Y—Z | B |
|---|---|---|---|---|---|---|---|---|---|---|---|
| 319 | H | Br | H | H | tBut | H | Me | H | $CH_2$ | $CH_2$—N—$CH_2$ | —$(CH_2)_4$— |
| 320 | H | I | H | H | tBut | H | Ph | H | $CH_2$—$CH_2$ | CH=C—$CH_2$ | —$(CH_2)_4$— |
| 321 | H | Ph | H | H | tBut | H | 1-Pyrrolyl | H | $CH_2$ | CH=C—$CH_2$ | —$(CH_2)_4$— |
| 322 | H | p(iProp)-Ph | H | H | iProp | H | 2-Napht | H | $CH_2$—$CH_2$ | $CH_2$—CH=C | —$(CH_2)_4$— |
| 323 | H | pAcetyl-Ph | H | H | Et | H | tBut | H | $CH_2$ | $CH_2$—N—$CH_2$ | —$(CH_2)_3$— |
| 324 | H | pBr-Ph | H | H | Et | H | tBut | H | $CH_2$ | $CH_2$—N—$CH_2$ | —$(CH_2)_3$— |
| 325 | H | pI-Ph | H | OMe | $CF_3$ | H | H | H | $CH_2$ | CH=C—$CH_2$ | —$(CH_2)_4$— |
| 326 | H | iProp | H | H | $CF_3$ | H | tBut | H | $CH_2$—$CH_2$ | $CH_2$—N—$CH_2$ | —$(CH_2)_4$— |
| 327 | H | tBut | H | H | iProp | H | H | H | $CH_2$ | $CH_2$—N—$CH_2$ | —$(CH_2)_4$— |
| 328 | H | CN | H | H | H | CN | tBut | H | $CH_2$—$CH_2$ | $CH_2$—N—$CH_2$ | —$(CH_2)_3$— |
| 329 | H | COOEt | H | H | H | F | tBut | H | $CH_2$—$CH_2$ | $CH_2$—CH=C | —$(CH_2)_4$— |
| 330 | H | OPh | H | H | H | Cl | iProp | H | $CH_2$—$CH_2$ | $CH_2$—N—$CH_2$ | —$(CH_2)_4$— |
| 331 | Me | Br | H | H | tBut | H | H | OMe | $CH_2$ | $CH_2$—CH—C | —$(CH_2)_4$— |
| 332 | CN | I | H | H | iProp | H | H | H | $CH_2$ | $CH_2$—N—$CH_2$ | —$(CH_2)_4$— |
| 333 | Me | Ph | H | H | $CHF_2$ | H | tBut | H | $CH_2$—$CH_2$ | CH=C—$CH_2$ | —$(CH_2)_3$— |
| 334 | F | p(iProp)-Ph | H | OMe | tBut | H | $CF_3$ | H | $CH_2$—$CH_2$ | $CH_2$—N—$CH_2$ | —$(CH_2)_4$— |
| 335 | Me | pAcetyl-Ph | H | H | $CF_3$ | H | tBut | H | $CH_2$ | $CH_2$—N—$CH_2$ | —$(CH_2)_5$— |
| 336 | H | pBr-Ph | Me | H | nProp | CN | tBut | H | $CH_2$ | $CH_2$—N—$CH_2$ | —$(CH_2)_4$— |
| 337 | H | pI-Ph | F | H | $CF_3$ | CN | iProp | H | $CH_2$ | CH=C—$CH_2$ | —$(CH_2)_4$— |
| 338 | H | iProp | Me | H | Ph | C=CH | tBut | H | $CH_2$—$CH_2$ | $CH_2$—N—$CH_2$ | —$(CH_2)_3$— |
| 339 | H | tBut | CN | H | tBut | H | H | H | $CH_2$ | $CH_2$—CH=C | —$(CH_2)_4$— |
| 340 | H | CN | Me | H | tBut | CN | $CF_3$ | OMe | $CH_2$—$CH_2$ | $CH_2$—N—$CH_2$ | —$(CH_2)_5$— |
| 341 | H | COOEt | Me | H | nProp | F | tBut | H | $CH_2$ | $CH_2$—N—$CH_2$ | —$(CH_2)_4$— |
| 342 | H | OPh | F | H | Ph | CN | tBut | Me | $CH_2$ | $CH_2$—CH=C | —$(CH_2)_3$— |
| 343 | Cl | F | H | H | tBut | F | H | H | $CH_2$—$CH_2$ | $CH_2$—N—$CH_2$ | —$(CH_2)_4$— |
| 344 | H | Br | H | H | tBut | H | Me | H | $CH_2$ | $CH_2$—N—$CH_2$ | —$CH_2$—$(=CH_2)_{CH2}$— |
| 345 | H | I | H | H | tBut | H | Ph | H | $CH_2$ | $CH_2$—CH=C | —$CH_2$—C(=$CH_2$)—$CH_2$— |
| 346 | H | Ph | H | H | tBut | H | 1-Pyrrolyl | H | $CH_2$—$CH_2$ | CH=C—$CH_2$ | —$CH_2$—C(=$CH_2$)—$CH_2$— |
| 347 | H | $NEt_2$ | H | H | iProp | H | 2-Napht | H | $CH_2$—$CH_2$ | $CH_2$—CH=C | —$CH_2$—C($CH_3$)=CH—$CH_2$— |
| 348 | H | pAcetyl-Ph | H | H | Et | H | tBut | H | $CH_2$ | $CH_2$—N—$CH_2$ | —$CH_2$—CH($CH_3$)—$CH_2$— |
| 349 | H | pBr-Ph | H | H | $CHF_2$ | H | H | H | $CH_2$—$CH_2$ | CH=C—$CH_2$ | —$CH_2$—C(=$CH_2$)—$CH_2$— |
| 350 | H | pI-Ph | H | F | $CF_3$ | H | H | H | $CH_2$ | $CH_2$—CH=C | —$CH_2$—CH($CH_3$)—$CH_2$— |
| 351 | H | iProp | H | H | $CF_3$ | H | tBut | H | $CH_2$—$CH_2$ | $CH_2$—N—$CH_2$ | —$CH_2$—C(=$CH_2$)—$CH_2$— |
| 352 | H | tBut | H | H | iProp | H | H | H | $CH_2$ | $CH_2$—N—$CH_2$ | —$CH_2$—C(=$CH_2$)—$CH_2$— |
| 353 | H | CN | H | H | H | CN | tBut | H | $CH_2$ | $CH_2$—N—$CH_2$ | —$CH_2$—CH=CH—$CH_2$— |
| 354 | H | COOEt | H | H | H | F | tBut | H | $CH_2$—$CH_2$ | $CH_2$—CH=C | —$CH_2$—C($CH_3$)=CH—$CH_2$— |
| 355 | H | OPh | H | H | H | Cl | iProp | H | $CH_2$—$CH_2$ | $CH_2$—N—$CH_2$ | —$CH_2$—C(=$CH_2$)—$CH_2$— |
| 356 | Me | Br | H | H | tBut | H | H | OMe | $CH_2$ | $CH_2$—CH=C | —$CH_2$—CH($CH_3$)—$CH_2$— |
| 357 | Me | I | H | H | iProp | H | H | OMe | $CH_2$ | $CH_2$—N—$CH_2$ | —$CH_2$—CH($CH_3$)—$CH_2$— |
| 358 | Cl | Ph | H | H | $CHF_2$ | H | tBut | H | $CH_2$—$CH_2$ | $CH_2$CH=C | —$CH_2$—C(=$CH_2$)—$CH_2$— |
| 359 | CN | p(iProp)-Ph | H | OMe | tBut | H | $CF_3$ | H | $CH_2$ | $CH_2$—N—$CH_2$ | —$CH_2$—CH=CH—$CH_2$— |
| 360 | F | pAcetyl-Ph | H | OMe | $CF_3$ | H | tBut | H | $CH_2$ | $CH_2$—N—$CH_2$ | —$CH_2$—C(=$CH_2$)—$CH_2$— |
| 361 | Me | pBr-Ph | H | H | nProp | CN | tBut | H | $CH_2$—$CH_2$ | $CH_2$—N—$CH_2$ | —$CH_2$—C($CH_3$)=CH—$CH_2$— |
| 362 | H | pI-Ph | CN | H | $CF_3$ | CN | iProp | H | $CH_2$ | $CH_2$—CH=C | —$CH_2$—CH($CH_3$)—$CH_2$— |
| 363 | H | iProp | Cl | H | Ph | C=CH | tBut | H | $CH_2$—$CH_2$ | $CH_2$—N—$CH_2$ | —$CH_2$—CH($CH_3$)—$CH_2$— |
| 364 | H | tBut | F | H | tBut | CN | H | H | $CH_2$ | $CH_2$—CH=C | —$CH_2$—C($CH_3$)=CH—$CH_2$— |
| 365 | H | CN | Cl | H | tBut | CN | $CF_3$ | OMe | $CH_2$—$CH_2$ | $CH_2$—N—$CH_2$ | —$CH_2$—CH=CH—$CH_2$— |
| 366 | H | COOEt | CN | H | nProp | F | tBut | H | $CH_2$ | $CH_2$—N—$CH_2$ | —$CH_2$—CH($CH_3$)—$CH_2$— |
| 367 | H | OPh | Cl | H | Ph | CN | tBut | Me | $CH_2$—$CH_2$ | $CH_2$—CH=C | —$CH_2$—C($CH_3$)=CH—$CH_2$— |
| 368 | H | F | Me | H | tBut | F | H | H | $CH_2$ | $CH_2$—N—$CH_2$ | —$CH_2$—C(=$CH_2$)—$CH_2$— |

TABLE 14

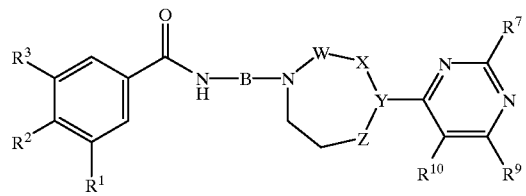

| Example No. | R1 | R2 | R3 | R7 | R9 | R10 | W | X—Y—Z | B |
|---|---|---|---|---|---|---|---|---|---|
| 369 | H | Br | H | tBut | Ph | H | CH$_2$ | CH$_2$—N—CH$_2$ | —(CH$_2$)$_4$— |
| 370 | H | I | H | tBut | 2-Napht | H | CH$_2$ | CH$_2$—N—CH$_2$ | —(CH$_2$)$_4$— |
| 371 | H | Ph | H | tBut | 1-Pyrrolyl | H | CH$_2$ | CH$_2$—N—CH$_2$ | —CH$_2$—C(=CH$_2$)—CH$_2$— |
| 372 | H | p(iProp)-Ph | H | tBut | cHex | H | CH$_2$—CH$_2$ | CH=C—CH$_2$ | —CH$_2$—C(CH$_3$)=CH—CH$_2$— |
| 373 | H | pAcetyl-Ph | H | tBut | nHex | H | CH$_2$—CH$_2$ | CH$_2$—N—CH$_2$ | —(CH$_2$)$_4$— |
| 374 | H | pBr-Ph | H | tBut | H | OMe | CH$_2$ | CH$_2$—N—CH$_2$ | —CH$_2$—CH(CH$_3$)—CH$_2$— |
| 375 | H | pI-Ph | H | iProp | F | H | CH$_2$—CH$_2$ | CH$_2$—N—CH$_2$ | —CH$_2$—CH=CH—CH$_2$— |
| 376 | H | iProp | H | CH$_3$ | 1-Pyrrolyl | H | CH$_2$ | CH$_2$—C=CH | —(CH$_2$)$_4$— |
| 377 | H | tBut | H | OMe | 1-Pyrrolyl | H | CH$_2$ | CH$_2$N—CH$_2$ | —CH$_2$—CH(CH$_3$)—CH$_2$— |
| 378 | H | CN | H | tBut | H | CH$_3$ | CH$_2$—CH$_2$ | CH=C—CH$_2$ | —CH$_2$—(CH$_3$)—CH$_2$— |
| 379 | H | COOEt | H | tBut | tBut | OMe | CH$_2$—CH$_2$ | CH$_2$—N—CH$_2$ | —(CH$_2$)$_4$— |
| 380 | H | OPh | H | tBut | iProp | H | CH$_2$ | CH$_2$—N—CH$_2$ | —CH$_2$—C(=CH$_2$)—CH$_2$— |
| 381 | Me | Br | H | Ph | tBut | Cl | CH$_2$ | CH$_2$—C=CH | —CH$_2$—C(CH$_3$)=CH—CH$_2$— |
| 382 | CN | I | H | 2-Napht | tBut | Me | CH$_2$—CH$_2$ | CH=C—CH$_2$ | —(CH$_2$)$_4$— |
| 383 | Me | Ph | H | tBut | CF$_3$ | Me | CH$_2$ | CH$_2$—N—CH$_2$ | —CH$_2$—C(=CH$_2$)—CH$_2$— |

TABLE 15

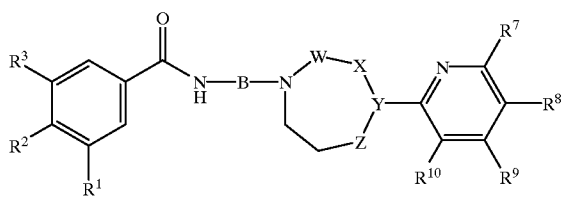

| Example No. | R1 | R2 | R3 | R7 | R8 | R9 | R10 | W | X—Y—Z | B |
|---|---|---|---|---|---|---|---|---|---|---|
| 384 | H | Br | H | tBut | H | tBut | H | CH$_2$ | CH$_2$—N—CH$_2$ | —(CH$_2$)$_4$— |
| 385 | H | I | H | tBut | CN | H | H | CH$_2$ | CH$_2$—N—CH$_2$ | —(CH$_2$)$_4$— |
| 386 | H | Ph | H | tBut | H | Cl | H | CH$_2$ | CH$_2$—N—CH$_2$ | —CH$_2$—C(=CH$_2$)—CH$_2$— |
| 387 | H | p(iProp)-Ph | H | H | CN | tBu | H | CH$_2$—CH$_2$ | CH$_2$—N=C | —CH$_2$—CH(CH$_3$)—CH$_2$— |
| 388 | H | pAcetyl-Ph | H | CF$_3$ | H | tBut | H | CH$_2$ | CH$_2$—N—CH$_2$ | —(CH$_2$)$_4$— |
| 389 | H | pBr-Ph | H | nProp | H | iProp | H | CH$_2$—CH$_2$ | CH=C—CH$_2$ | —CH$_2$—CH(CH$_3$)—CH$_2$— |
| 390 | H | pI-Ph | H | H | H | iProp | OMe | CH$_2$—CH$_2$ | CH$_2$—CH=C | —(CH$_2$)$_4$— |
| 391 | H | iProp | H | tBut | H | tBut | H | CH$_2$ | CH$_2$—N—CH$_2$ | —CH$_2$—C(=CH$_2$)—CH$_2$— |
| 392 | H | tBut | H | tBut | CN | H | H | CH$_2$—CH$_2$ | CH$_2$—N—CH$_2$ | —(CH$_2$)$_4$— |
| 393 | H | CN | H | tBut | H | Cl | H | CH$_2$ | CH$_2$—N—CH$_2$ | —(CH$_2$)$_3$— |
| 394 | H | COOEt | H | H | CN | tBu | H | CH$_2$ | CH=C—CH$_2$ | —CH$_2$—C(CH$_3$)=CH—CH$_2$— |
| 395 | H | OPh | H | CF$_3$ | H | tBut | H | CH$_2$—CH$_2$ | CH$_2$—N—CH$_2$ | —CH$_2$—C(=CH$_2$)—CH$_2$— |
| 396 | Me | Br | H | nProp | H | iProp | H | CH$_2$ | CH$_2$—N—CH$_2$ | —(CH$_2$)$_4$— |
| 397 | CN | I | H | H | H | iProp | OMe | CH$_2$ | CH$_2$—N—CH$_2$ | —(CH$_2$)$_4$— |
| 398 | Me | Ph | H | nProp | CN | tBut | H | CH$_2$—CH$_2$ | CH$_2$—N—CH$_2$ | —(CH$_2$)$_4$— |
| 399 | F | p(iProp)-Ph | H | CF$_3$ | CN | iProp | H | CH$_2$—CH$_2$ | CH$_2$—CH=C | —(CH$_2$)$_4$ |
| 400 | Me | pAcetyl-Ph | H | Ph | C=CH | tBut | H | CH$_2$ | CH$_2$—N—CH$_2$ | —CH$_2$—CH(CH$_3$)—CH$_2$— |
| 401 | H | pBr-Ph | Me | tBut | CN | tBut | H | CH$_2$—CH$_2$ | CH=C—CH$_2$ | —CH$_2$—CH(CH$_3$)—CH$_2$— |
| 402 | H | pI-Ph | F | tBut | H | nProp | H | CH$_2$ | CH$_2$—N—CH$_2$ | —(CH$_2$)$_3$— |
| 403 | H | iProp | Me | Ph | H | tBut | OMe | CH$_2$ | CH$_2$—CH=C | —(CH$_2$)$_5$— |
| 404 | H | tBut | CN | CF$_3$ | H | tBut | F | CH$_2$—CH$_2$ | CH=C—CH$_2$ | —CH$_2$—CH(CH$_3$)—CH$_2$— |
| 405 | H | CN | Me | tBut | F | H | Me | CH$_2$ | CH$_2$—N—CH$_2$ | —CH$_2$—CH=CH—CH$_2$— |
| 406 | H | COOEt | Me | nProp | CN | tBut | Me | CH$_2$—CH$_2$ | CH$_2$—CH=C | —CH$_2$—C(=CH$_2$)—CH$_2$— |
| 407 | H | pAcetyl-Ph | F | nProp | C=CH | tBut | H | CH$_2$ | CH=C—CH$_2$ | —CH$_2$—C(CH$_3$)=CH—CH$_2$— |
| 408 | Cl | F | H | tBut | CN | H | Me | CH$_2$ | CH$_2$—N—CH$_2$ | —(CH$_2$)$_4$— |

TABLE 16

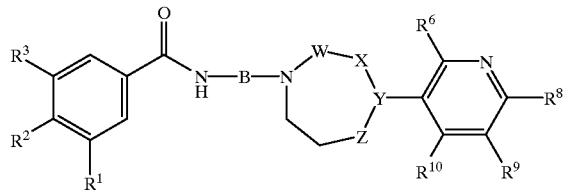

| Example No. | R1 | R2 | R3 | R6 | R8 | R9 | R10 | W | X—Y—Z | B |
|---|---|---|---|---|---|---|---|---|---|---|
| 409 | H | Br | H | OMe | H | tBut | H | CH₂ | CH₂—N—CH₂ | —(CH₂)₄— |
| 410 | H | I | H | OMe | H | CF₃ | H | CH₂ | CH₂—N—CH₂ | —(CH₂)₄— |
| 411 | H | Ph | H | OMe | H | tBut | H | CH₂—CH₂ | CH₂—N—CH₂ | —CH₂—C(=CH₂)—CH₂— |
| 412 | H | p(iProp)-Ph | H | H | CN | tBut | H | CH₂ | CH=C—CH₂ | —CH₂—C(CH₃)=CH—CH₂— |
| 413 | H | pAcetyl-Ph | H | H | F | tBut | H | CH₂ | CH₂—N—CH₂ | —(CH₂)₄— |
| 414 | H | pBr-Ph | H | Me | Cl | iProp | H | CH₂ | CH₂—CH=C | —CH₂—C(=CH₂)—CH₂— |
| 415 | H | pI-Ph | H | H | H | iProp | H | CH₂—CH₂ | CH=C—CH₂ | —(CH₂)₄— |
| 416 | H | iProp | H | H | H | tBut | OMe | CH₂—CH₂ | CH₂—N—CH₂ | —CH₂—C(=CH₂)—CH₂— |
| 417 | H | tBut | H | CN | H | CF₃ | H | CH₂—CH₂ | CH₂—N—CH₂ | —(CH₂)₄— |
| 418 | H | CN | H | H | CN | H | OMe | CH₂ | CH₂—N—CH₂ | —CH₂—CH(CH₃)—CH₂— |
| 419 | H | COOEt | H | H | H | tBu | F | CH₂ | CH₂—CH=C | —CH₂—C(CH₃)=CH—CH₂— |
| 420 | H | OPh | H | H | CN | tBut | H | CH₂—CH₂ | CH₂—N—CH₂ | —(CH₂)₃— |
| 421 | Me | Br | H | Me | H | iProp | H | CH₂ | CH₂—N—CH₂ | —(CH₂)₄— |
| 422 | CN | I | H | OMe | H | iProp | H | CH₂—CH₂ | CH₂—N—CH₂ | —CH₂—CH(CH₃)—CH₂— |
| 423 | Me | Ph | H | OMe | CN | tBut | H | CH₂ | CH=C—CH₂ | —(CH₂)₄— |

TABLE 17

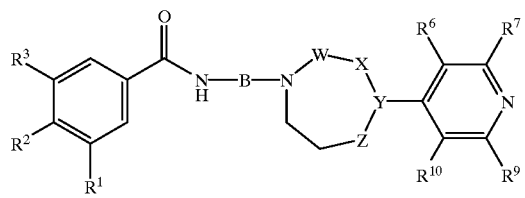

| Example No. | R1 | R2 | R3 | R6 | R7 | R9 | R10 | W | X—Y—Z | B |
|---|---|---|---|---|---|---|---|---|---|---|
| 430 | H | Br | H | H | tBut | tBut | H | CH₂ | CH₂—N—CH₂ | —(CH₂)₄— |
| 431 | H | I | H | H | tBut | Ph | H | CH₂ | CH₂—N—CH₂ | —(CH₂)₄— |
| 432 | H | Ph | H | H | tBut | 1-Pyrrolyl | H | CH₂ | CH₂—N—CH₂ | —CH₂—C(=CH₂)—CH₂— |
| 433 | H | p(iProp)-Ph | H | H | nPropyl | tBut | H | CH₂—CH₂ | CH₂—N=C | —CH₂—C(CH₃)=CH—CH₂— |
| 434 | H | pAcetyl-Ph | H | H | CF₃ | tBut | H | CH₂ | CH₂—N—CH₂ | —(CH₂)₄— |
| 435 | H | pBr-Ph | H | H | 2-Napht | tBut | H | CH₂—CH₂ | CH—C—CH₂ | —CH₂—C(=CH₂)—CH₂— |
| 436 | H | pI-Ph | H | OMe | tBut | H | H | CH₂—CH₂ | CH₂—CH=C | —(CH₂)₄— |
| 437 | H | iProp | H | OMe | iProp | H | H | CH₂ | CH₂—N—CH₂ | —CH₂—C(=CH₂)—CH₂— |
| 438 | H | tBut | H | OMe | H | CF₃ | H | CH₂—CH₂ | CH₂—N—CH₂ | —(CH₂)₄— |
| 439 | H | CN | H | H | tBut | H | H | CH₂ | CH₂—N—CH₂ | —CH₂—CH(CH₃)—CH₂— |
| 440 | H | COOEt | H | H | iProp | H | Me | CH₂ | CH=C—CH₂ | —CH₂—C(CH₃)=CH—CH₂— |
| 441 | H | OPh | H | CN | tBut | H | H | CH₂—CH₂ | CH₂—N—CH₂ | —(CH₂)₃— |
| 442 | Me | Br | H | H | H | CF₃ | Me | CH₂ | CH₂—N—CH₂ | —(CH₂)₄— |
| 443 | CN | I | H | H | nProp | tBut | H | CH₂ | CH₂—N—CH₂ | —CH₂—CH(CH₃)—CH₂— |
| 444 | Me | Ph | H | OMe | tBut | iProp | H | CH₂—CH₂ | CH₂—N—CH₂ | —(CH₂)₄— |
| 445 | F | p(iProp)-Ph | H | OMe | CF₃ | tBut | H | CH₂—CH₂ | CH=C—CH₂ | —(CH₂)₄— |
| 446 | Me | pAcetyl-Ph | H | Me | tBut | nProp | H | CH₂ | CH₂—CH=C | —CH₂—CH=CH—CH₂ |
| 447 | H | pBr-Ph | Me | Me | tBut | H | H | CH₂—CH₂ | CH₂—N—CH₂ | —CH₂—C(=CH₂)—CH₂— |
| 448 | H | pI-Ph | F | H | tBut | tBut | H | CH₂ | CH₂—CH=C | —(CH₂)₃— |
| 449 | H | IProp | Me | Me | CF₃ | tBut | H | CH₂ | CH₂—CH=C | —CH₂—CH(CH₃)—CH₂— |

Examples of pharmaceutical presentations

A) Tablets
Tablets of the following composition were compressed in a tabletting machine in a conventional way:

| | |
|---|---|
| 40 mg | of substance of Example 1 |
| 120 mg | of corn starch |
| 13.5 mg | of gelatin |
| 45 mg | of lactose |
| 2.25 mg | of Aerosil ® (chemically pure silica in submicroscopically fine distribution) |
| 6.75 mg | of potato starch (as 6% paste) |

B) Coated tablets

| | |
|---|---|
| 20 mg | of substance from Example 4 |
| 60 mg | of core composition |
| 70 mg | of sugar-coating composition |

The core composition consists of 9 parts of corn starch, 3 parts of lactose and 1 part of vinylpyrrolidone/vinyl acetate 60:40 copolymer. The sugar-coating composition consists of 5 parts of sucrose, 2 parts of corn starch, 2 parts of calcium carbonate and 1 part of talc. The coated tablets produced in this way are subsequently provided with an enteric coating.
Biological investigations—receptor-binding studies
1) $D_3$ binding assay
Cloned CCL 1,3 mouse fibroblasts which express the human $D_3$ receptor and which are obtainable from Res. Biochemicals Internat. One Strathmore Rd., Natick, Mass. 01760-2418 USA, were employed for the binding studies.
Cell preparation
The $D_3$ expressing cells were grown in RPMI-1640 with 10% fetal calf serum (GIBCO No. 041-32400 N); 100 U/ml penicillin and 0.2% streptomycin (GIBCO BRL, Gaithersburg, Md., USA). After 48 h, the cells were washed with PBS and incubated with 0.05% trypsin-containing PBS for 5 min. After neutralization with medium, the cells were collected by centrifugation at 300 g. For cell lysis, the pellet was briefly washed with lysis buffer (5 mM tris-HCl, pH 7.4 with 10% glycerol) and then incubated at a concentration of 107 cells/ml of lysis buffer at 4° C. for 30 min. The cells were centrifuged at 200 g for 10 min and the pellet was stored in liquid nitrogen.
Binding assays
For the $D_3$ receptor binding assay, the membranes were suspended in incubation buffer (50 mM Tris-HCl, pH 7.4 with 120 mM NaCl, 5 mM KCl, 2 mM $CaCl_2$, 2 mM $MgCl_2$, 10 $\mu$M quinolinol, 0.1% ascorbic acid and 0.1% BSA) at a concentration of about 106 cells/250 Al of assay mixture and incubated with 0.1 nM $^{125}$I-sulpiride in the presence and absence of test substance at 30° C. The non-specific binding was determined with $10^{-6}$ M spiperone.

After 60 min, filtration through GF/B glass fiber filters (Whatman, England) in a Skatron cell collector (Skatron, Lier, Norway) separated the free and the bound radioligand, and the filters were washed with ice-cold tris-HCl buffer, pH 7.4. The radioactivity collected on the filters was quantified using a Packard 2200 CA liquid scintillation counter.

The $K_i$ values were determined by non-linear regression analysis using the LIGAND program.
2) $D_2$ binding assay
Cell culture
HEK-293 cells with stably expressed human dopamine D2A receptors were cultivated in RPMI 1640 with Glutamax I™ and 25 mM HEPES with 10% fetal calf serum albumin. All the media contained 100 units of penicillin per ml and 100 $\mu$g/ml streptomycin. The cells ere maintained at 37° C. in a moist atmosphere with 5% $CO_2$.

The cells were prepared for binding studies by trypsinization (0.05% trypsin solution) at room temperature for 3–5 minutes. The cells were then centrifuged at 250 g for 10 minutes and treated with lysis buffer (5 mM tris-HCl, 10% glycerol, pH 7.4) at 4° C. for 30 minutes. After centrifugation at 250 g for 10 minutes, the residue was stored at −20° C. until used.
Receptor binding assays
1) Dopamine $D_2$ receptor "low affinity state" with $^{125}$I-spiperone (81 TBq/mmol, Du Pont de Nemours, Dreieich)
The mixtures (1 ml) consisted of 1×10$^5$ cells in incubation buffer (50 mM tris,120 mM NaCl, 5 mM KCl, 2 mM $MgCl_2$ and 2 mM $CaCl_2$, pH 7.4 with HCl) and 0.1 nM $^{125}$I-spiperone (total binding) or with the addition of 1 VM haloperidol (nonspecific binding) or test substance.

After incubation at 25° C. for 60 minutes, the mixtures were filtered through GF/B glass fiber filters (Whatman, England) in a skatron cell collector (Zinsser, Frankfurt), and the filters were washed with ice-cold 50 mM tris-HCl buffer, pH 7.4. The radioactivity collected on the filters was quantified using a Packard 2200 CA liquid scintillation counter. Evaluation took place as under a).

The $K_i$ values were determined by nonlinear regression analysis using the ligand program or by conversion of the $IC_{50}$ values using the formula of Cheng and Prusoff.

In these assays, the compounds according to the invention show very good affinities on the $D_3$ receptor and high selectivities for the $D_3$ receptor.

The compounds listed below were obtained in a similar way:

| Ex. No. | Ar¹ | A | Ar² | M. p. [° C.] |
|---|---|---|---|---|
| 450 | 4-OH-2-methylpyrimidin-yl | —S—CH₂—C(=CH₂)—CH₂— | 2-tert-butyl-4-CF₃-6-methylpyrimidinyl | 80–90 (Oxalate) |
| 451 | 4-OH-2-methylpyrimidin-yl | —S—CH₂—CH(CH₃)—CH₂— | 3-CF₃-phenyl | 110–113 |
| 452 | 4-OH-2-methylpyrimidin-yl | —S—CH₂—CH(CH₃)—CH₂— | 2-tert-butyl-4-propyl-6-methylpyrimidinyl | 106–108 |
| 453 | 4-OH-2-methylpyrimidin-yl | —S—CH₂—C(CH₃)=CH—CH₂— | 2-tert-butyl-4-CF₃-6-methylpyrimidinyl | 129–131 |

-continued

| Ex. No. | Ar¹ | A | Ar² | M.p. [° C.] |
|---|---|---|---|---|
| 454 | 2-methyl-6-phenyl-4-hydroxypyrimidine | —S—(CH$_2$)$_3$— | 2-tert-butyl-4-methyl-6-trifluoromethylpyrimidine | 227–131 (Hydrochloride) |
| 455 | 2-methyl-6-(2-methoxyphenyl)-4-hydroxypyrimidine | —S—(CH$_2$)$_3$— | 2-tert-butyl-4-methyl-6-trifluoromethylpyrimidine | 165–166 (Hydrochloride) |
| 456 | N-methyl-4-bromobenzamide | —(CH$_2$)$_5$— | 2-tert-butyl-4-methyl-6-trifluoromethylpyrimidine | 115–118 (Oxalate) |

-continued

| Ex. No. | Ar¹ | A | Ar² | M.p. [° C.] |
|---|---|---|---|---|
| 457 | 4-Br-C₆H₄-C(O)-N(CH₃)H (4-bromo-N-methylbenzamide) | —(CH₂)₄— | 2-tert-butyl-6-methyl-4-(CF₂Cl)-pyrimidinyl | 94–97 (Hydrochloride) |
| 458 | 4-(CH₃C(O))-biphenyl-4'-C(O)-N(CH₃)H | —(CH₂)₄— | 2-tert-butyl-6-methyl-4-(CF₃)-pyrimidinyl | 123–126 (Fumarate) |
| 459 | 4-Br-C₆H₄-C(O)-N(CH₃)H | —(CH₂)₃—CH(CH₃)— | 2-tert-butyl-6-methyl-4-(CF₃)-pyrimidinyl | 130–133 (Fumarate) |

Ar¹—A—N(ring: 1,4-diazepane)—Ar²

-continued

| Ex. No. | Ar¹ | A | Ar² | M.p. [° C.] |
|---|---|---|---|---|
| 460 | N-methyl 4-bromobenzamide | -CH₂-CH=CH-CH₂- | 2-tert-butyl-6-methyl-4-CF₃-pyrimidine | 118-125 (Fumarate) |
| 461 | N-methyl 4-bromobenzamide | -CH₂-CH(CH₃)-CH₂-(CH₂)₂- | 2-tert-butyl-6-methyl-4-CF₃-pyrimidine | 130-132 (Oxalate) |
| 462 | N-methyl 4-bromobenzamide | -(CH₂)₆- | 2-tert-butyl-6-methyl-4-CF₃-pyrimidine | 144-150 (Fumarate) |
| 463 | N-methyl 2-methoxy-5-bromobenzamide | -(CH₂)₄- | 2-tert-butyl-6-methyl-4-CF₃-pyrimidine | 148-154 (Oxalate) |

-continued

Ar¹—A—N⟨...⟩N—Ar²

| Ex. No. | Ar¹ | A | Ar² | M.p. [° C.] |
|---|---|---|---|---|
| 464 | 4-Br-C₆H₄-C(O)-N(CH₃)H | -CH₂-CH(CH₃)-(CH₂)₂- | 2-tBu-4-Me-6-CF₃-pyrimidin-yl | 171–176 (Fumarate) |
| 465 | 4-CH₃O-C₆H₄-C(O)-N(CH₃)H | -(CH₂)₄- | 2-tBu-4-Me-6-CF₃-pyrimidin-yl | 122–124 (Fumarate) |
| 466 | 4-NH₂-5-Cl-2-OCH₃-C₆H₂-C(O)-N(CH₃)H | -(CH₂)₄- | 2-tBu-4-Me-6-CF₃-pyrimidin-yl | 108–112 (Oxalate) |

-continued

| Ex. No. | Ar¹ | A | Ar² | M. p. [° C.] |
|---|---|---|---|---|
| 467 | N-methylbenzamide | —(CH₂)₄— | 2-tert-butyl-4-methyl-6-trifluoromethylpyrimidine | 140–142 (Oxalate) |
| 468 | 4-methoxy-N-methylbenzamide | —(CH₂)₄— | 2-methoxyphenyl | 149–152 (Fumarate) |
| 469 | 4-bromo-N-methylbenzamide | —(CH₂)₄— | 2-methoxyphenyl | 147–149 (Hydrochloride) |
| 470 | N-methyl-4-nitrobenzamide | —(CH₂)₄— | 2-methoxyphenyl | 235–236 (Fumarate) |

-continued

| Ex. No. | Ar¹ | A | Ar² | M.p. [° C.] |
|---|---|---|---|---|
| 471 | 5-amino-2-methyl-thiazole | —S—CH₂—C(CH₂)—CH₂— | 2-tert-butyl-6-methyl-4-(trifluoromethyl)pyrimidine | 92–98 |
| 472 | 5-amino-2-methyl-thiazole | —S—CH₂—CH(CH₃)—CH₂— | 2-tert-butyl-6-methyl-4-propylpyrimidine | 87–90 |
| 473 | N-methyl-benzothiophene-2-carboxamide | —(CH₂)₄— | 2-tert-butyl-6-methyl-4-(trifluoromethyl)pyrimidine | 112–115 (Fumarate) |
| 474 | N-methyl-benzothiophene-2-carboxamide | —(CH₂)₆— | 2-tert-butyl-6-methyl-4-(trifluoromethyl)pyrimidine | 101–105 (Oxalate) |

-continued

| Ex. No. | Ar¹ | A | Ar² | M. p. [° C.] |
|---|---|---|---|---|
| 475 | benzothiophene-2-C(=O)-N(CH₃)H | —(CH₂)₄— | 2-tert-butyl-6-methyl-4-(CF₂Cl)-pyrimidine | 127–129 (Oxalate) |
| 476 | 2-methyl-4-hydroxypyrimidine | —S—(CH₂)₃— | 2-(pyrrol-1-yl)-6-methyl-pyrimidine | |
| 477 | 5-methyl-1-methyl-4-amino-imidazole | —S—(CH₂)₃— | 2-(pyrrol-1-yl)-6-methyl-4-(N(CH₂CH₂Ph))-pyrimidine | |
| 478 | 3-methyl-5-phenyl-1-methyl-pyrazole | —S—(CH₂)₃— | 3-cyanophenyl | 126–128 (Fumarate) |

-continued

Structure: Ar¹—A—N(CH₂CH₂)₂N—Ar² (1,4-diazepane ring)

| Ex. No. | Ar¹ | A | Ar² | M.p. [°C.] |
|---|---|---|---|---|
| 479 | 5-methyl-4-amino-1-methylimidazol-2-yl | —S—(CH₂)₃— | 3-cyanophenyl | 150–156 (Fumarate) |
| 480 | 2-methyl-4-hydroxypyrimidin-6-yl | —S—(CH₂)₃— | 3-cyanophenyl | 158–165 (Fumarate) |
| 481 | 5-methyl-4-phenyl-1-methylimidazol-2-yl | —S—(CH₂)₃— | 3-chlorophenyl | |
| 482 | 5-methyl-4-amino-1-methylimidazol-2-yl | —S—(CH₂)₃— | 3-chlorophenyl | 184–188 (Oxalate) |
| 483 | 2-methyl-4-hydroxypyrimidin-6-yl | —S—(CH₂)₃— | 3-chlorophenyl | 185–187 (Oxalate) |

-continued

| Ex. No. | Ar¹ | A | Ar² | M. p. [° C.] |
|---|---|---|---|---|
| 484 | | | | |
| 485 | | | | 127 |
| 486 | | | | 128 |
| 487 | | | | 123 |

-continued $Ar^1-A\underset{\underset{\displaystyle N}{|}}{\overset{\overset{\displaystyle N-Ar^2}{|}}{}}$

| Ex. No. | Ar¹ | A | Ar² | M.p. [° C.] |
|---|---|---|---|---|
| 488 | 2-methyl-4-hydroxypyrimidine | —S—(CH₂)₃— | 4-tert-butyl-6-methylpyrimidine | 120 |
| 489 | 5-methyl-1-methyl-3-amino-imidazole | —S—(CH₂)₃— | 4-CF₃-6-methylpyrimidine | 187–191 (Oxalate) |
| 490 | 5-methyl-1-methyl-3-(methylamino)-imidazole | —S—(CH₂)₃— | 4-CF₃-6-methylpyrimidine | 187–191 (Oxalate) |
| 491 | 5-methyl-1-methyl-3-phenyl-imidazole | —S—(CH₂)₃— | 4-CF₃-6-methylpyrimidine | |
| 492 | 2-methyl-4-hydroxypyrimidine | —S—(CH₂)₃— | 4-CF₃-6-methylpyrimidine | |

-continued
| Ex. No. | Ar¹ | A | Ar² | M.p. [° C.] |
|---|---|---|---|---|
| 493 | 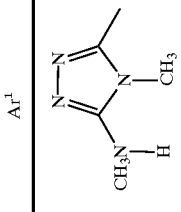 | —S—(CH₂)₃— | 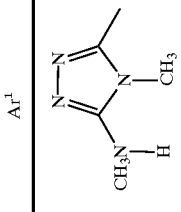 | |
| 494 | 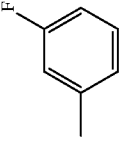 | —S—(CH₂)₃— | 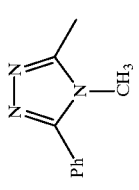 | 93–94 (Oxalate) |
| 495 | 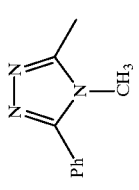 | —S—(CH₂)₃— | 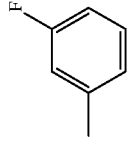 | |
| 496 | 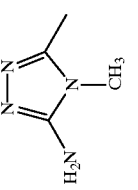 | —S—(CH₂)₃— | 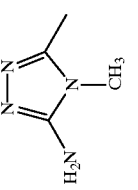 | |
| 497 | 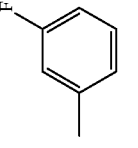 | —S—(CH₂)₃— | 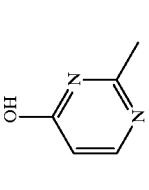 | 168–170 (Fumarate) |

-continued

| Ex. No. | Ar¹ | A | Ar² | M.p. [° C.] |
|---|---|---|---|---|
| 498 | 5-amino-1,2-dimethyl-imidazole | —S—(CH₂)₃— | 2-CF₃-4-tert-butyl-6-methyl-pyrimidine | |
| 499 | 5-amino-1,2-dimethyl-imidazole | CH₂=C(CH₂—)CH₂—S—CH₂— | 2-tert-butyl-6-(3,4-dimethoxyphenyl)-4-methyl-pyrimidine | |
| 500 | 4-hydroxy-2-methyl-pyrimidine | —S—(CH₂)₃— | 2-tert-butyl-4-(CF₂CF₂CF₃)-6-methyl-pyrimidine | |

-continued

| Ex. No. | Ar¹ | A | Ar² | M.p. [° C.] |
|---|---|---|---|---|
| 501 | 5-amino-1,2-dimethyl-imidazol-4-yl | —S—(CH$_2$)$_3$— | 2-tert-butyl-4-methyl-6-(pentafluoropropyl)pyrimidin-... | |
| 502 | 2-methyl-4-hydroxy-pyrimidinyl | —S—CH$_2$—C(=CH$_2$)—CH$_2$— | 2-tert-butyl-4-methyl-6-(pentafluoropropyl)pyrimidin-... | |
| 503 | 1,2-dimethyl-5-phenyl-imidazol-4-yl | —S—CH$_2$—C(=CH$_2$)—CH$_2$— | 2-tert-butyl-4-methyl-6-(pentafluoropropyl)pyrimidin-... | |
| 504 | 5-amino-1,2-dimethyl-imidazol-4-yl | —S—CH$_2$—C(=CH$_2$)—CH$_2$— | 2-tert-butyl-4-methyl-6-(pentafluoropropyl)pyrimidin-... | |

| Ex. No. | Ar¹ | A | Ar² | M.p. [°C] |
|---|---|---|---|---|
| 505 | 4-hydroxy-2-methylpyrimidine | —S—(CH$_2$)$_3$— | 2-tert-butyl-4-methylpyrimidine | |
| 506 | 5-methyl-1-methyl-imidazol-2-amine | —S—(CH$_2$)$_3$— | 2-tert-butyl-4-methylpyrimidine | |
| 507 | 4-hydroxy-2-methylpyrimidine | —S—CH$_2$—C(=CH$_2$)—CH$_2$— | 2-tert-butyl-4-methyl-6-(butyl)pyrimidine | |
| 508 | 5-methyl-1-methyl-imidazol-2-(methylamino) | —S—CH$_2$—C(=CH$_2$)—CH$_2$— | 2-tert-butyl-4-methyl-6-(butyl)pyrimidine | |

-continued

| Ex. No. | Ar¹ | A | Ar² | M.p. [° C.] |
|---|---|---|---|---|
| 509 | 5-methyl-1-methyl-4-amino-imidazole | —S—CH₂—C(=CH₂)—CH₂— | 2-tert-butyl-6-methyl-4-(propyl with CH₃)pyrimidine | |
| 510 | 2-methyl-4-hydroxypyrimidine | —S—CH₂—C(=CH₂)—CH₂— | 2-tert-butyl-6-methylpyrimidine | |
| 511 | 5-methyl-1-methyl-4-amino-imidazole | —S—(CH₂)₃— | 2,6-di-tert-butyl-4-methylpyrimidine | |
| 512 | 2-methyl-4-hydroxypyrimidine | —S—(CH₂)₃— | 2,6-di-tert-butyl-4-methylpyrimidine | |

-continued

| Ex. No. | Ar¹ | A | Ar² | M.p. [° C.] |
|---|---|---|---|---|
| 513 | 3-amino-1,5-dimethyl-1H-pyrazol-4-yl | -S-CH₂-C(=CH₂)-CH₂- | 2-(1-adamantyl)-4-methyl-6-(trifluoromethyl)pyrimidin-5-yl | |
| 514 | 4-hydroxy-2-methylpyrimidin-5-yl | -S-CH₂-C(=CH₂)-CH₂- | 2-(1-adamantyl)-4-methyl-6-(trifluoromethyl)pyrimidin-5-yl | |
| 515 | 4-hydroxy-2-methylpyrimidin-5-yl | -S-(CH₂)₃- | 2-(1-adamantyl)-4-methyl-6-(trifluoromethyl)pyrimidin-5-yl | |

-continued

| Ex. No. | Ar¹ | A | Ar² | M.p. [°C.] |
|---|---|---|---|---|
| 516 | 5-amino-1,2-dimethylimidazole | —S—(CH₂)₃— | 2-(1-adamantyl)-4-methyl-6-trifluoromethylpyrimidine | 81–85 |
| 517 | 5-amino-1,2-dimethylimidazole | —S—CH₂—C(=CH₂)—CH₂— | 2-tert-butyl-4-methylpyrimidine | |
| 518 | 1,2-dimethyl-5-methylaminoimidazole | —S—CH₂—C(=CH₂)—CH₂— | 4-tert-butyl-2-(1-pyrrolyl)-6-methylpyrimidine | |
| 519 | 1,2-dimethyl-5-methylaminoimidazole | —S—CH₂—C(=CH₂)—CH₂— | 2-tert-butyl-4-methyl-6-(1-pyrrolyl)pyrimidine | |

-continued

| Ex. No. | Ar¹ | A | Ar² | M.p. [° C.] |
|---|---|---|---|---|
| 520 | 5-methyl-4-methylamino-1-methyl-1H-1,2,4-triazole | –S–CH₂–C(=CH₂)–CH₂– | 2-(1-adamantyl)-4-tert-butyl-6-methylpyrimidine | 75–80 |
| 521 | 3-amino-5-methyl-1-methyl-1H-1,2,4-triazole | –S–CH₂–C(=CH₂)–CH₂– | 2-(1-adamantyl)-4-tert-butyl-6-methylpyrimidine | 110–112 (Hydrochloride) |
| 522 | 2-methyl-4-hydroxypyrimidine | –S–(CH₂)₃– | 2-(1-adamantyl)-4-tert-butyl-6-methylpyrimidine | 78–80 |

-continued

| Ex. No. | Ar¹ | A | Ar² | M.p. [° C.] |
|---|---|---|---|---|
| 523 | 3-methyl-5-phenyl-1-methyl-pyrazol-4-yl | —S—CH₂—C(=CH₂)—CH₂— | 2-(adamantyl)-4-tert-butyl-6-methylpyrimidin-? | 95–97 (Hydrochloride) |
| 524 | 5-amino-3-methyl-1-methyl-pyrazol-4-yl | —S—CH₂—C(=CH₂)—CH₂— | 2-(adamantyl)-4-tert-butyl-6-methylpyrimidin-? | 142–145 |
| 525 | 4-hydroxy-2-methylpyrimidin-? | —S—CH₂—C(=CH₂)—CH₂— | 2-(adamantyl)-4-tert-butyl-6-methylpyrimidin-? | 80–91 |

-continued

| Ex. No. | Ar¹ | A | Ar² | M. p. [° C.] |
|---|---|---|---|---|
| 526 | 3-methyl-5-phenyl-1-methyl-1H-pyrazol-4-yl | –S–CH₂–C(=CH₂)–CH₂– | 4-tert-butyl-6-methyl-2-(1H-pyrrol-1-yl)pyrimidinyl | Oxalate |
| 527 | 5-amino-3-methyl-1-methyl-1H-pyrazol-4-yl | –S–(CH₂)₈– | 3-(difluoromethyl)phenyl | Hydrochloride |
| 528 | 2-methyl-4-hydroxypyrimidin-6-yl | –S–(CH₂)₃– | 2-tert-butyl-6-methyl-4-butylpyrimidinyl | Oxalate |
| 529 | 5-amino-3-methyl-1-methyl-1H-pyrazol-4-yl | –S–(CH₂)₃– | 2-tert-butyl-6-methyl-4-butylpyrimidinyl | DiHydrochloride |

| Ex. No. | Ar¹ | A | Ar² | M.p. [° C.] |
|---|---|---|---|---|
| 530 | | | | Oxalate |
| 531 | | | | |
| 532 | | | | |

-continued

| Ex. No. | Ar¹ | A | Ar² | M.p. [° C.] |
|---|---|---|---|---|
| 533 | 2-methyl-4-hydroxypyrimidine | —S—CH₂—C(=CH₂)—CH₂— | 2-tert-butyl-6-methyl-4-(pyrrol-1-yl)pyrimidine | 95–96 |
| 534 | 2-methyl-4-hydroxypyrimidine | —S—CH₂—C(=CH₂)—CH₂— | 2-tert-butyl-6-methyl-4-(3,4-dimethoxyphenyl)pyrimidine | |
| 535 | 2-methyl-4-hydroxypyrimidine | —S—(CH₂)₃— | 2-tert-butyl-6-methyl-4-(3,4-dimethoxyphenyl)pyrimidine | 92 |

| Ex. No. | Ar¹ | A | Ar² | M.p. [°C] |
|---|---|---|---|---|
| 536 | 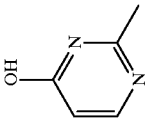 | —S—(CH$_2$)$_3$— | 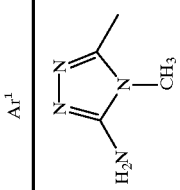 | 90 |
| 537 |  | 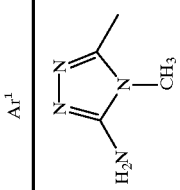 | 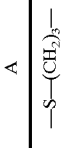 | 97 |
| 538 | 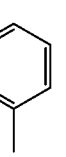 | —S—(CH$_2$)$_3$— | 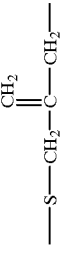 | 98–100 |
| 539 | 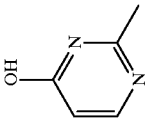 | 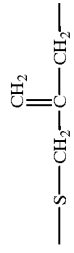 | 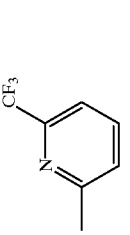 | |

-continued

| Ex. No. | Ar¹ | A | Ar² | M.p. [° C.] |
|---|---|---|---|---|
| 540 | 5-amino-1,2-dimethylimidazole | —S—CH₂—C(=CH₂)—CH₂— | 3-methylphenyl-CHF₂ | |
| 541 | 5-amino-1,2-dimethylimidazole | —S—(CH₂)₃— | 3-methylphenyl-CHF₂ | 66–72 |
| 542 | 4-hydroxy-2-methylpyrimidine | —S—(CH₂)₃— | 2-tert-butyl-4-methyl-6-(CF₂CF₃)pyrimidine | |
| 543 | 5-hydroxy-1,3-dimethyl-1,2,4-triazole | —S—(CH₂)₃— | 2-tert-butyl-4-methyl-6-(CF₂CF₃)pyrimidine | |

| Ex. No. | Ar¹ | A | Ar² | M.p. [° C.] |
|---|---|---|---|---|
| 544 | 5-methyl-4-(methylamino)-1H-1,2,4-triazole | —S—(CH$_2$)$_3$— | 2-tert-butyl-6-methyl-4-(pentafluoroethyl)pyrimidine | |
| 545 | 3-amino-5-methyl-1H-1,2,4-triazole | —S—(CH$_2$)$_3$— | 2-tert-butyl-6-methyl-4-(pentafluoroethyl)pyrimidine | |
| 546 | 4-hydroxy-2-methylpyrimidine | —S—(CH$_2$)$_3$— | 4-tert-butyl-6-methyl-2-(1H-pyrrol-1-yl)pyrimidine | |

-continued
| Ex. No. | Ar¹ | A | Ar² | M.p. [° C.] |
|---|---|---|---|---|
| 547 | 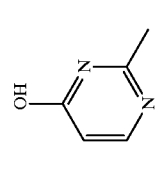 | —S—(CH₂)₃— | 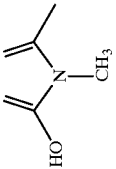 | |
| 548 |  | —S—(CH₂)₃— |  | |
| 549 |  | —S—(CH₂)₃— |  | |

-continued

| Ex. No. | Ar¹ | A | Ar² | M.p. [° C.] |
|---|---|---|---|---|
| 550 | 5-methyl-3-hydroxy-1-methyl-pyrazole | —S—(CH₂)₃— | 2-tert-butyl-6-methyl-4-(pyrrol-1-yl)pyrimidine | |
| 551 | 5-methyl-3-amino-1-methyl-pyrazole | —S—(CH₂)₃— | 2-tert-butyl-6-methyl-4-(pyrrol-1-yl)pyrimidine | |
| 552 | 4-hydroxy-2-methyl-pyrimidine | —S—CH₂—C(=CH₂)—CH₂— | 2-tert-butyl-4-methyl-pyrimidine | |
| 553 | 5-methyl-3-hydroxy-1-methyl-pyrazole | —S—CH₂—C(=CH₂)—CH₂— | 2-tert-butyl-4-methyl-pyrimidine | |

-continued

| Ex. No. | Ar¹ | A | Ar² | M.p. [° C.] |
|---|---|---|---|---|
| 554 | 4-amino-1,5-dimethyl-imidazol-3-yl | —S—CH₂—C(=CH₂)—CH₂— | 2-tert-butyl-4-methyl-pyrimidin-6-yl | |
| 555 | 4-hydroxy-2-methyl-pyrimidin-6-yl | —S—CH₂—C(=CH₂)—CH₂— | 4,6-di-tert-butyl-2-methyl-pyrimidin-... | |
| 556 | 4-amino-1,5-dimethyl-imidazol-3-yl | —S—CH₂—C(=CH₂)—CH₂— | 4,6-di-tert-butyl-2-methyl-pyrimidin-... | |
| 557 | 4-amino-1,5-dimethyl-imidazol-3-yl | —S—CH₂—C(=CH₂)—CH₂— | 2-isopropyl-4-difluoromethyl-6-methyl-pyrimidin-... | |

-continued

| Ex. No. | Ar¹ | A | Ar² | M.p. [° C.] |
|---|---|---|---|---|
| 558 | 2-methyl-4-hydroxypyrimidine | −S−CH₂−C(=CH₂)−CH₂− | 2-isopropyl-4-CHF₂-6-methylpyrimidine | 100–103 |
| 559 | 2-methyl-4-hydroxypyrimidine | −S−(CH₂)₃− | 2-isopropyl-4-CHF₂-6-methylpyrimidine | |
| 560 | 5-amino-1,3-dimethyl-1H-1,2,4-triazole | −S−(CH₂)₃− | 2-isopropyl-4-CHF₂-6-methylpyrimidine | 109–112 |

-continued
| Ex. No. | Ar¹ | A | Ar² | M.p. [° C.] |
|---|---|---|---|---|
| 561 | 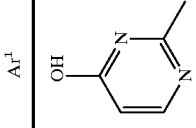 | —S—(CH₂)₃— | 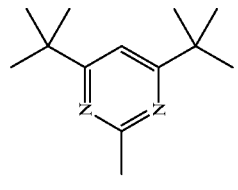 | |
| 562 | 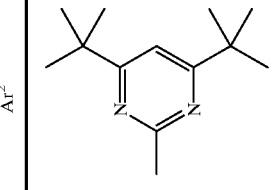 | —S—(CH₂)₃— | 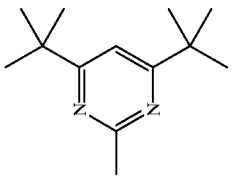 | |
| 563 | 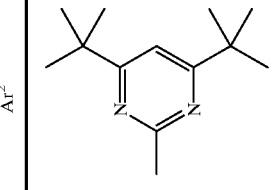 | —S—(CH₂)₃— | 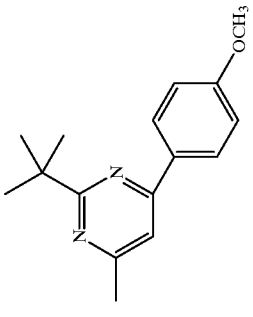 | |

-continued

| Ex. No. | Ar¹ | A | Ar² | M.p. [° C.] |
|---|---|---|---|---|
| 564 | OH-pyrimidine-CH₃ | —S—(CH₂)₃— | tBu,CH₃-pyrimidine-C₆H₄-OCH₃ | |
| 565 | OH-pyrimidine-CH₃ | —S—CH₂—C(=CH₂)—CH₂— | tBu,CH₃-pyrimidine-C₆H₄-OCH₃ | 84–85 |
| 566 | H₂N,CH₃-triazole-N-CH₃ | —S—CH₂—C(=CH₂)—CH₂— | tBu,CH₃-pyrimidine-C₆H₄-OCH₃ | |

-continued

| Ex. No. | Ar¹ | A | Ar² | M.p. [° C.] |
|---|---|---|---|---|
| 567 | 5-methyl-4-amino-imidazole (N-CH₃) | —S—CH₂—C(CH₃)(CH₂—)—CH₂— | 2-methyl-6-CF₃-pyridine | |
| 568 | 5-methyl-4-amino-imidazole (N-CH₃) | —S—(CH₂)₃— | 2-methyl-6-CF₃-pyridine | |
| 569 | 2-methyl-4-hydroxy-pyridine | —S—(CH₂)₃— | 2-methyl-6-CF₃-pyridine | |
| 570 | 2-methyl-4-hydroxy-pyridine | —S—(CH₂)₃— | 2-methyl-4-tert-butyl-pyrimidine | |
| 571 | 5-methyl-2-hydroxy-imidazole (N-CH₃) | —S—(CH₂)₃— | 2-methyl-4-tert-butyl-pyrimidine | |

-continued

| Ex. No. | Ar¹ | A | Ar² | M.p. [° C.] |
|---|---|---|---|---|
| 572 | 3-amino-4-methyl-1-methyl-pyrazole | —S—(CH$_2$)$_3$— | 4-tert-butyl-2-methylpyrimidine | 185–190 |
| 573 | 3-amino-4-methyl-1-methyl-pyrazole | —S—(CH$_2$)$_3$— | 2-trichloromethyl-6-methylpyridine | 145–148 |
| 574 | 3-amino-4-methyl-1-methyl-pyrazole | —S—CH$_2$—C(=CH$_2$)—CH$_2$— | 2,6-di-tert-butyl-4-methylpyrimidine | — |
| 575 | 3-amino-4-methyl-1-methyl-pyrazole | —S—CH$_2$—C(CH$_3$)=CH—CH$_2$— | 2-tert-butyl-6-trifluoromethyl-4-methylpyrimidine | 120–122 |

-continued

| Ex. No. | Ar¹ | A | Ar² | M. p. [° C.] |
|---|---|---|---|---|
| 576 | 5-amino-1-methyl-3-methyl-pyrazole | —S—CH₂—C(=CH₂)—CH₂— | 2-tert-butyl-4-methyl-6-trifluoromethyl-pyrimidine | 70–80 (Oxalate) |
| 577 | 5-amino-1-methyl-3-methyl-pyrazole | —S—CH₂—C(CH₃)=CH—CH₂— | 3-methylphenyl | 155–160 (Hydrochloride) |
| 578 | 1-isopropyl-3-methyl-5-methyl-pyrazole | —S—(CH₂)₃— | 2-tert-butyl-4-methyl-6-trifluoromethyl-pyrimidine | 97–98 (Hydrochloride) |
| 579 | 1-isopropyl-3-methyl-5-methyl-pyrazole | —S—CH₂—C(=CH₂)—CH₂— | 2,6-di-tert-butyl-4-methyl-pyrimidine | 141–143 (Fumarate) |

-continued
| Ex. No. | Ar¹ | A | Ar² | M. p. [° C.] |
|---|---|---|---|---|
| 580 |  |  |  | 105–108 (Hydrochloride) |
| 581 |  |  |  | 139–143 (Hydrochloride) |
| 582 |  |  |  | 89–95 |
| 583 |  |  |  | 160–165 (Oxalate) |

-continued

| Ex. No. | Ar¹ | A | Ar² | M. p. [°C.] |
|---|---|---|---|---|
| 584 | 5-methyl-1-methyl-3-mercapto-1,2,4-triazole | —(CH₂)₄— | 2-tert-butyl-6-methyl-4-CF₃-pyrimidine | 62–64 |
| 585 | 5-methyl-1-phenyl-3-mercapto-1,2,4-triazole | —(CH₂)₄— | 2-tert-butyl-6-methyl-4-CF₃-pyrimidine | 148–149 |
| 586 | 5-methyl-1-(2-methylpropyl)-3-mercapto-1,2,4-triazole | —(CH₂)₄— | 2-tert-butyl-6-methyl-4-CF₃-pyrimidine | 38–41 |
| 587 | 5-methyl-4-phenyl-1-methyl-1,2,4-triazole | —CH=CH—(CH₂)₂— | 2-tert-butyl-6-methyl-4-CF₃-pyrimidine | Oil |

(Ar¹—A—N(CH₂CH₂CH₂)N—Ar²: 1,4-diazepane core linking Ar¹–A– and –Ar²)

-continued
| Ex. No. | Ar¹ | A | Ar² | M. p. [° C.] |
|---|---|---|---|---|
| 588 | 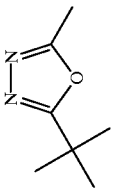 | —S—(CH₂)₃— | 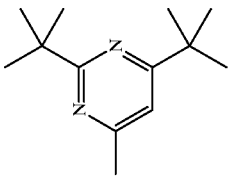 | 90 (Decomposition) (Hydrochloride) |
| 589 | 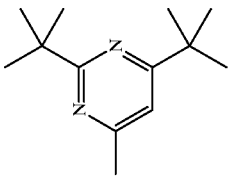 | —S—(CH₂)₃— | 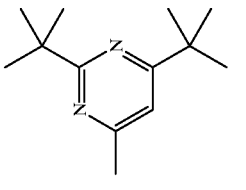 | 90–93 (Fumarate) |
| 590 | 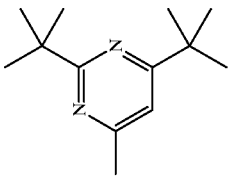 | —S—(CH₂)₃— | 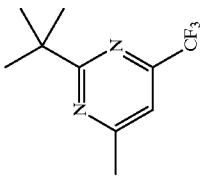 | 75–78 (Fumarate) |

-continued
| Ex. No. | Ar¹ | A | Ar² | M.p. [° C.] |
|---|---|---|---|---|
| 591 |  | 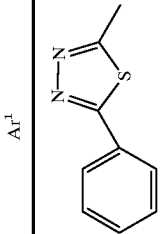 | 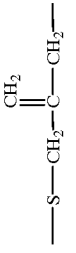 | Oil |
| 592 | 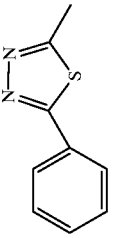 | —S—(CH₂)₃— | 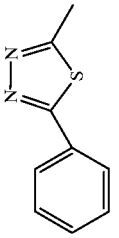 | 130–133 (Hyrochlorid) |
| 593 |  | —S—(CH₂)₃— | 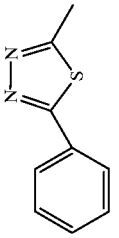 | Oil |

-continued

| Ex. No. | Ar¹ | A $\mathrm{Ar^1-A-N\underset{\underset{N-Ar^2}{\diagdown}}{\diagup}}$ | Ar² | M. p. [° C.] |
|---|---|---|---|---|
| 594 | 2-methyl-5-H₃C-oxazole | —S—CH₂—C(=CH₂)—CH₂— | 2-tert-butyl-4-methyl-6-CF₃-pyrimidine | 126–130 (Hydrochloride) |
| 595 | 2,5-dimethyl-1-methyl-imidazole | —S—(CH₂)₃— | 2,6-di-tert-butyl-4-methyl-pyrimidine | 90–95 (Decomposition) (Hydrochloride) |
| 596 | 2-methyl-5-tert-butyl-oxazole | —S—CH₂—C(=CH₂)—CH₂— | 2-tert-butyl-4-methyl-6-CF₃-pyrimidine | Oil |

-continued

Structure: Ar¹—A—N(ring)N—Ar² (1,4-diazepane linker)

| Ex. No. | Ar¹ | A | Ar² | M.p. [° C.] |
|---|---|---|---|---|
| 597 | 2-tert-butyl-5-methyl-1,3,4-oxadiazol-yl | —S—(CH₂)₃— | 2-tert-butyl-4-methyl-6-trifluoromethylpyrimidin-yl | Oil |
| 598 | 3-(2-iodophenyl)-1,5-dimethyl-1,2,4-triazol-yl | —S—(CH₂)₃— | 2-tert-butyl-4-methyl-6-trifluoromethylpyrimidin-yl | 106 (Hydrochloride) |
| 599 | 3-(4-methylphenyl)-1,5-dimethyl-1,2,4-triazol-yl | —S—(CH₂)₃— | 2-tert-butyl-4-methyl-6-trifluoromethylpyrimidin-yl | 148 (Hydrochloride) |

-continued

| Ex. No. | Ar¹ | A | Ar² | M.p. [° C.] |
|---|---|---|---|---|
| 600 | 3-iodophenyl-4-methyl-1-methylimidazole | —S—(CH$_2$)$_3$— | 2,6-di-tert-butyl-4-methylpyrimidine | 137–139 (Hydrochloride) |
| 601 | 3-iodophenyl-4-methyl-1-methylimidazole | —S—CH$_2$—C(=CH$_2$)—CH$_2$— | 2-tert-butyl-6-CF$_3$-4-methylpyrimidine | 109–115 (Hydrochloride) |
| 602 | 2,4-dinitrophenyl-4-methyl-1-methyltriazole | —S—(CH$_2$)$_3$— | 2-tert-butyl-6-CF$_3$-4-methylpyrimidine | 90 (Decomposition) (Hydrochloride) |

-continued
| Ex. No. | Ar¹ | A | Ar² | M. p. [° C.] |
|---|---|---|---|---|
| 603 | 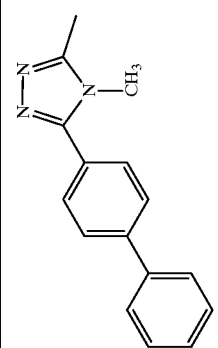 | —S—CH₂—C(=CH₂)—CH₂— |  | 132 (Decomposition) (Hydrochloride) |
| 604 | 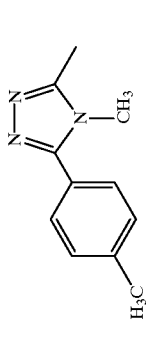 | —S—CH₂—C(=CH₂)—CH₂— | 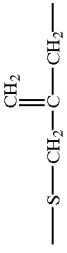 | 103–105 (Hydrochloride) |
| 605 | 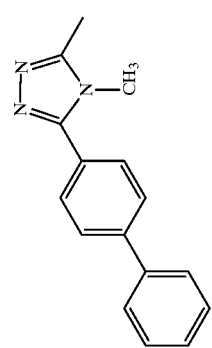 | —S—(CH₂)₃— |  | 142–144 |

-continued

| Ex. No. | Ar¹ | A | Ar² | M.p. [° C.] |
|---|---|---|---|---|
| 606 | 3-iodophenyl-(4-methyl-1-methyl-1H-1,2,4-triazol-3-yl) | —S—(CH₂)₃— | 2-tert-butyl-6-trifluoromethyl-4-methylpyrimidine | Oil |
| 607 | 4-methylphenyl-(4-methyl-1-methyl-1H-1,2,4-triazol-3-yl) | —S—(CH₂)₃— | 2-tert-butyl-6-trifluoromethyl-4-methylpyrimidine | Oil |
| 608 | 4-methylphenyl-(4-methyl-1-methyl-1H-1,2,4-triazol-3-yl) | —S—(CH₂)₃— | 2,6-di-tert-butyl-4-methylpyrimidine | 120–123 (Hydrochloride) |

-continued

| Ex. No. | Ar¹ | A | Ar² | M. p. [° C.] |
|---|---|---|---|---|
| 609 | 5-methyl-1H-imidazol-4-yl, 2-methoxyphenyl | 1,4-diazepane (N–A–N-Ar², Ar¹–A) | 2,6-di-tert-butyl-4-methylpyrimidin-yl | 187–189 (Fumarate) |
| 610 | 5-methyl-1H-imidazol-4-yl, 2-methoxyphenyl | —S—CH₂—C(=CH₂)—CH₂— | 2,6-di-tert-butyl-4-methylpyrimidin-yl | 95–98 (Fumarate) |
| 611 | 5-methyl-1H-imidazol-4-yl, 2-methoxyphenyl | —S—CH₂—C(=CH₂)—CH₂— | 2-tert-butyl-6-trifluoromethyl-4-methylpyrimidin-yl | 68–72 (Fumarate) |

-continued

| Ex. No. | Ar¹ | A | Ar² | M. p. [° C.] |
|---|---|---|---|---|
| 612 | 4-methyl-5-methyl-imidazole with propyl chain | —S—(CH$_2$)$_3$— | 2-tert-butyl-4-methyl-6-CF$_3$-pyrimidine | 240 (Hydrochloride) |
| 613 | 4-methyl-5-methyl-imidazole with propyl chain | —S—CH$_2$—C(=CH$_2$)—CH$_2$— | 2-tert-butyl-4-methyl-6-CF$_3$-pyrimidine | 190 (Hydrochloride) |
| 614 | 4-methyl-5-methyl-imidazole with propyl chain | —S—(CH$_2$)$_3$— | 2,6-di-tert-butyl-4-methyl-pyrimidine | 243 (Hydrochloride) |

-continued
| Ex. No. | Ar¹ | A | Ar² | M.p. [° C.] |
|---|---|---|---|---|
| 615 | 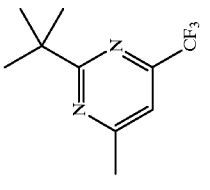 | —S—(CH$_2$)$_3$— | 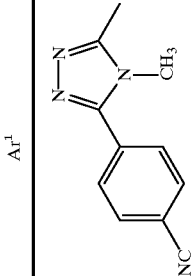 | 101–104 |
| 616 | 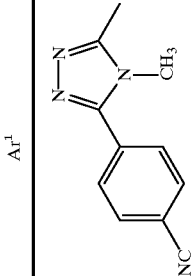 | —S—(CH$_2$)$_3$— | 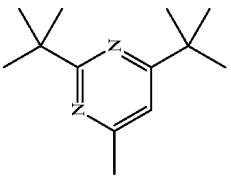 | Oil |
| 617 | 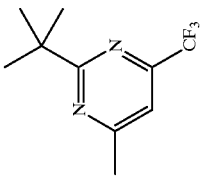 | 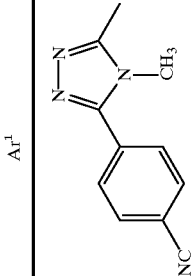 | 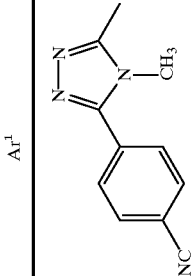 | 90–94 (Decomposition) (Hydrochloride) |

-continued

| Ex. No. | Ar¹ | A | Ar² | M.p. [° C.] |
|---|---|---|---|---|
| | | Ar¹—A—N⌒N—Ar² | | |
| 618 | 3-methyl-1-phenyl-imidazole (5-yl) | —S—CH₂—C(=CH₂)—CH₂— | 2,6-di-tert-butyl-4-methylpyrimidin-yl | 152 (Hydrochloride) |
| 619 | 3-methyl-1-methyl-imidazole (5-yl) | —S—(CH₂)₃— | 2,6-di-tert-butyl-4-methylpyrimidin-yl | Oil |
| 620 | 3-methyl-1-methyl-5-phenyl-imidazol-yl | —S—(CH₂)₃— | 2,6-di-tert-butyl-4-methylpyrimidin-yl | Oil |

-continued

| Ex. No. | Ar¹ | A | Ar² | M.p. [° C.] |
|---|---|---|---|---|
| 621 | 3-methyl-1-methyl-imidazole (H at 5) | —S—CH₂—C(CH₂)(CH₂)—CH₂— | 2,6-di-tert-butyl-4-methylpyrimidine | 152 (Hydrochloride) |
| 622 | 3-methyl-1-methyl-5-Ph-imidazole | —S—(CH₂)₃— | 2,6-di-tert-butyl-4-methylpyrimidine | 110 (Hydrochloride) |
| 623 | 3-methyl-1-methyl-5-(4-iodophenyl)-imidazole | —S—(CH₂)₃— | 2-tert-butyl-6-CF₃-4-methylpyrimidine | 126–131 (Hydrochloride) |

-continued

| Ex. No. | Ar¹ | A | Ar² | M. p. [° C.] |
|---|---|---|---|---|
| 624 | | —S—(CH₂)₃— | | 91 (Hydrochloride) |
| 625 | | —S—(CH₂)₃— | | 116–120 (Hydrochloride) |
| 626 | | —S—CH₂—C(=CH₂)—CH₂— | | 103 (Hydrochloride) |

-continued

| Ex. No. | Ar¹ | A | Ar² | M.p. [°C.] |
|---|---|---|---|---|
| 627 | 5-methyl-1-phenyl-1H-imidazol-2-yl (H at 4) | —S—(CH$_2$)$_3$— | 2,6-di-tert-butyl-4-methylpyrimidin-... | 150 (Hydrochloride) |
| 628 | 3,5-dimethyl-1-phenyl-1H-imidazol-2-yl | —S—CH$_2$—C(=CH$_2$)—CH$_2$— | 2-tert-butyl-6-trifluoromethyl-4-methylpyrimidinyl | 140 (Hydrochloride) |
| 629 | 3,5-dimethyl-1-phenyl-1H-imidazol-2-yl | —S—(CH$_2$)$_3$— | 2-tert-butyl-6-trifluoromethyl-4-methylpyrimidinyl | 130 (Hydrochloride) |

-continued

| Ex. No. | Ar¹ | A | Ar² | M.p. [° C.] |
|---|---|---|---|---|
| 630 | 3-methyl-1-methyl-5-(pyrazin-2-yl)pyrazol-4-yl | —S—(CH₂)₃— | 2-tert-butyl-6-methyl-4-(trifluoromethyl)pyrimidin-5-yl | 98–104 (Hydrochloride) |
| 631 | 3-methyl-1-methyl-5-(pyrazin-2-yl)pyrazol-4-yl | —S—CH₂—C(=CH₂)—CH₂— | 2-tert-butyl-6-methyl-4-(trifluoromethyl)pyrimidin-5-yl | 65–68 (Hydrochloride) |
| 632 | 3-methyl-1-methyl-5-(pyrazin-2-yl)pyrazol-4-yl | —S—(CH₂)₃— | 2,6-di-tert-butyl-4-methylpyrimidin-5-yl | 131–136 (Hydrochloride) |

-continued

| Ex. No. | Ar¹ | A | Ar² | M.p. [°C.] |
|---|---|---|---|---|
| 633 | 3-methyl-5-(4-tert-butylphenyl)-1,2,4-triazol-1-yl with propyl-OCH₃ chain | —S—CH₂—C(=CH₂)—CH₂— | 2-tert-butyl-4-methyl-6-CF₃-pyrimidine | 105 (Hydrochloride) |
| 634 | 3-methyl-5-(4-tert-butylphenyl)-1,2,4-triazol-1-yl with propyl-OCH₃ chain | —S—CH₂—C(=CH₂)—CH₂— | 2-tert-butyl-4-methyl-6-CF₃-pyrimidine | 132 (Hydrochloride) |
| 635 | 5-methyl-1-phenyl-1,2,4-triazole-3-carboxylic acid ethyl ester | —S—CH₂—C(=CH₂)—CH₂— | 2-tert-butyl-4-methyl-6-CF₃-pyrimidine | 94 (Hydrochloride) |

-continued $$Ar^1-A-N\underset{\underset{Ar^2}{\underline{\qquad}}}{\overset{\overline{\qquad}}{N}}$$

| Ex. No. | Ar¹ | A | Ar² | M. p. [° C.] |
|---|---|---|---|---|
| 636 | 3-methyl-1H-imidazole (N-CH₃) | −S−CH₂−C(=CH₂)−CH₂− | 2-tert-butyl-6-CF₃-4-methylpyrimidine | 95 (Hydrochloride) |
| 637 | 3-methyl-1-phenyl-imidazole | −S−CH₂−C(=CH₂)−CH₂− | 2-tert-butyl-6-CF₃-4-methylpyrimidine | 102 (Hydrochloride) |
| 638 | 3-methyl-5-tert-butyl-1-methyl-imidazole | −S−(CH₂)₃− | 2-tert-butyl-6-CF₃-4-methylpyrimidine | 214–216 (Hydrochloride) |
| 639 | 3,4-dimethyl-5-(4-biphenyl)-imidazole | −S−(CH₂)₃− | 2-tert-butyl-6-CF₃-4-methylpyrimidine | 160–162 (Hydrochloride) |

-continued

| Ex. No. | Ar¹ | A | Ar² | M.p. [° C.] |
|---|---|---|---|---|
| 640 | 1,5-dimethyl-1H-pyrazol-3-amine group | —S—(CH$_2$)$_3$— | 2-tert-butyl-6-methyl-4-trifluoromethylpyrimidine | 73–75 (Fumarate) |
| 641 | ethyl 1,5-dimethyl-1H-imidazole-4-carboxylate | —CH$_2$—C(=CH$_2$)—CH$_2$—S— | 2-tert-butyl-6-methyl-4-trifluoromethylpyrimidine | 178 |
| 642 | 4-(4-tert-butylphenyl)-1,5-dimethyl-1H-imidazole | —S—(CH$_2$)$_3$— | 2-tert-butyl-6-methyl-4-trifluoromethylpyrimidine | 155 |

-continued

| Ex. No. | Ar¹ | A | Ar² | M. p. [° C.] |
|---|---|---|---|---|
| 643 | methyl 1-methyl-5-methyl-1H-imidazole-4-carboxylate (ethyl ester) | —S—(CH₂)₃— | 2-tert-butyl-6-CF₃-4-methylpyrimidine | 125–128 (Hydrochloride) |
| 644 | 3-methyl-5-(4-tert-butylphenyl)-1-(3-methoxypropyl)-1H-1,2,4-triazole | —S—(CH₂)₃— | 2-tert-butyl-6-CF₃-4-methylpyrimidine | 102 (Hydrochloride) |
| 645 | ethyl 5-methyl-1-phenyl-1H-imidazole-4-carboxylate | —S—(CH₂)₃— | 2-tert-butyl-6-CF₃-4-methylpyrimidine | 88 (Hydrochloride) |

-continued
| Ex. No. | Ar¹ | A | Ar² | M. p. [° C.] |
|---|---|---|---|---|
| 646 | 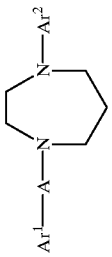 | —S—(CH$_2$)$_3$— | 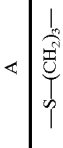 | 132 (Hydrochloride) |
| 647 | 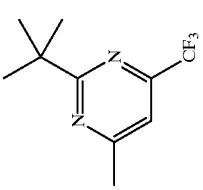 | 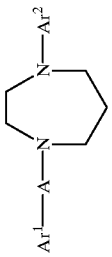 | 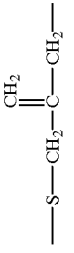 | 190 (Hydrochloride) |
| 648 | 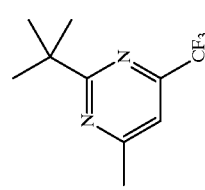 | —S—(CH$_2$)$_3$— | 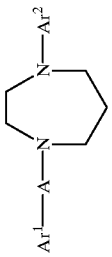 | 134–138 (Hydrochloride) |
| 649 |  | —S—(CH$_2$)$_3$— | 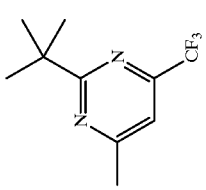 | 170–174 (Hydrochloride) |

-continued

| Ex. No. | Ar¹ | A | Ar² | M.p. [°C.] |
|---|---|---|---|---|
| 650 | 5-methyl-3-(methylamino)-1-methylpyrazole | —S—(CH$_2$)$_3$— | 2,6-di-tert-butyl-4-methylpyrimidine | 115 (Hydrochloride) |
| 651 | 5-methyl-3-(methylamino)-1-isopropylpyrazole | —S—(CH$_2$)$_3$— | 2-tert-butyl-4-methyl-6-trifluoromethylpyrimidine | 117 (Hydrochloride) |
| 652 | 5-methyl-3-(methylamino)-1-methylpyrazole | —S—CH$_2$—C(=CH$_2$)—CH$_2$— | 2-tert-butyl-4-methyl-6-trifluoromethylpyrimidine | 151–155 |
| 653 | 5-methyl-3-(methylamino)-1-isopropylpyrazole | —S—CH$_2$—C(=CH$_2$)—CH$_2$— | 2-tert-butyl-4-methyl-6-trifluoromethylpyrimidine | 158–161 (Hydrochloride) |

-continued

| Ex. No. | Ar¹ | A | Ar² | M.p. [°C.] |
|---|---|---|---|---|
| 654 | 3,5-dimethyl-4-phenyl-1-methylimidazole | —S—(CH$_2$)$_3$— | 2-tert-butyl-4-methyl-6-trifluoromethylpyrimidine | 184–185 (Hydrochloride) |
| 655 | 3,5-dimethyl-4-phenyl-1-methylimidazole | —S—CH$_2$—C(=CH$_2$)—CH$_2$— | 2-tert-butyl-4-methyl-6-trifluoromethylpyrimidine | 194–195 (Hydrochloride) |
| 656 | 3-tert-butyl-5-methyl-1-methylimidazole | —S—CH$_2$—C(=CH$_2$)—CH$_2$— | 2-tert-butyl-4-methyl-6-trifluoromethylpyrimidine | 114 (Hydrochloride) |

Ph = Phenyl

The compounds listed above which are not characterized by a melting point, have the following NMR spectra (d$_6$-DMSO):

Ex. no.

476 1,8–2,1 (m,4H); 2,6–2,7 (m,4H); 2,8 (t,2H); 3,2 (t,2H); 3,5–3,7 (b,2H); 3,7–3,9 (b,2H); 4,5 (d,2H); 5,1 (t,1H); 5,2 (s,1H); 6,1 (d,1H); 6,2 (m,2H); 7,3 (m,5H); 7,7 (m,2H); 7,8 (d,1H)

477 1,8–1,9 (m,4H); 2,5–2,6 (m,4H); 2,7 (t,2H); 3,0 (t,2H); 3,3 (s,3H); 3,5–3,8 (b,4H); 4,2 (s,2H); 4,5 (d,2H); 5,1 (t,1H); 5,2 (s,1H); 6,2 (m,2H); 7,3–7,4 (m,5H); 7,7 (m,2H)

481 Oxalate 2,1 (b,4H); 3,2–3,4 (m,8H); 3,6 (s,3H); 3,7 (b,2H); 6,6–6,8 (m,3H); 7,2 (t,1H); 7,6 (m,3H) 7,7 (m,2H)

484 Oxalate 2,0 (b,2H); 2,8–3,0 (b,4H); 3,4–3,5 (m,4H); 3,6–3,7 (b,2H); 3,9 (s,2H); 5,3 (d,2H); 6,1 (d,1H); 6,5–6,8 (m,3H); 7,21 (t,1H); 7,9 (d,1H);

491 Oxalate 2,0–2,3 (b,4H); 3,0–3,4 (b,8H); 3,6 (s,3H); 3,9 (b,2H); 4,1 (b,2H); 7,1–7,3 (b,1H); 7,5 (m,3H); 7,6 (m,2H); 8,6 (s,1H);

492 1,7–1,9 (m,4H); 2,6 (b,2H); 2,8 (b,2H); 3,1 (t,2H); 3,6–3,9 (b,4H); 6,1 (d,1H); 7,0 (d,1H); 7,8 (d,1H); 8,5 (s,1H);

493 Oxalate 1,9–2,1 (b,4H); 2,7 (s,3H); 2,8 (t,2H); 3,0–3,3 (b,6H); 3,3 (s,3H); 3,4 (t,2H); 3,7 (b,2H); 6,3 (b,1H); 6,4–6,5 (m,3H); 7,0 (m,1H);

495 Fumarate 1,6–1,8 (b,4H); 2,6 (m,2H); 2,7 (t,2H); 3,2 (s,3H); 3,3–3,5 (m,4H); 5,9 (s,2H); 6,2–6,5 (m,3H); 7,0 (M,1H);

497 Fumarate 1,6–1,8 (m,2H); 1,8–2,0 (b,2H); 2,5–2,7 (b,4H); 2,8–2,9 (m,4H); 3,2 (s,3H); 3,7–3,9 (m,4H); 5,9 (b,2H); 6,5 (s,2H); 7,4 (d,1H);

498 Fumarate 1,3 (s,9H); 1,8–2,1 (b,4H); 2,7–3,0 (b,6H); 3,3 (s,3H); 3,5–3,8 (b,6H); 6,1 (b,2H); 6,6 (s,2H); 6,7 (s,1H)i 499 Hydrochloride 1,3 (s,9H); 1,9 (b2H); 2,2 (s,2H); 2,5 (b,2H); 2,7 (b,2H); 3,1 (s,2H); 3,4 (s,3H); 3,7 (s,2H); 3,8 (s,3H); 3,9 (s,3H); 5,0 (d,2H); 6,5 (s,1H); 6,9 (d,1H); 7,5 (d,1H); 7,7 (s,1H);11,3 (b,1H);

500 Fumarate 1,3 (s,9H); 1,7–1,9 (b,4H); 2,5–2,7 (b,4H); 2,8–2,9 (b,2H); 3,1 (t,2H); 3,6–3,7 (b,2H); 3,8–4,0 (b,2H); 6,1 (d,1H); 6,6 (s,2H); 6,9 (d,1H); 7,8 (d,1H)

501 1,3 (s,9H); 1,8–2,0 (m,4H); 2,6 (m,4H); 2,8 (b,2H); 3,1 (t,2H); 3,4 (s,3H); 3,5 (b,2H); 3,9–4,1 (b,2H); 4,4 (b,2H); 6,5 (s,1H)

502 Fumarate 1,3 (s,9H); 1,8–1,9 (b,2H); 2,5–2,6 (b,2H); 2,7 (b,2H); 3,1 (s,2H); 3,6–3,7 (b,2H); 3,7–4,0 (m,4H); 5,1 (s,1H); 5,2 (s,1H); 6,1 (d,1H); 6,6 (s,2H); 6,9 (d,1H); 7,8 (d,1H)

503 Fumarate 1,3 (s,9H); 1,8–1,9 (b,2H); 2,5–2,6 (b,2H); 2,7–2,8 (b,2H); 3,2 (s,2H); 3,6 (s,3H); 3,6–3,7 (b,2H); 3,7 (s,2H); 3,8–4,0 (b,2H); 5,0 (s,1H); 5,1 (s,1H); 6,6 (s,2H); 6,9 (d,1H); 7,6 (m,3H); 7,7 (m,2H)

504 Fumarate 1,3 (s,9H); 1,8–1,9 (b,2H); 2,5 (b,2H); 2,6–2,7 (b,2H); 3,1 (s,2H); 3,3 (s,3H); 3,4 (s,2H); 3,5–3,7 (b,2H); 3,8–4,0 (b,2H); 4,9 (d,2H); 6,0 (s,2H); 6,6 (s,2H); 6,9 (d,1H)

505 Fumarate 1,3 (s,9H); 1,7–1,9 (b,4H); 2,5–2,7 (b,4H); 2,8 (t,2H); 3,1 (t,2H); 3,4–4,0 (b,4H); 6,1 (d,1H); 6,5 (d,1H); 6,6 (s,2H); 7,8 (d,1H); 8,2 (d,1H)

506 1,4 (s,9H); 1,8 (m,2H); 2,1–2,2 (b,2H); 2,6 (m,4H); 2,7 (t,2H); 3,0 (t,2H); 3,4 (s,3H); 3,5–4,0 (b,4H); 4,6 (b,2H); 6,2 (d,1H); 8,2 (d,1H)

507 0,9 (t,3H); 1,3 (s,9H); 1,4 (m,2H); 1,7 (m,2H); 2,1 (b,2H); 2,6 (t,2H); 2,7 (t,2H); 2,8 (t,2H); 3,3 (s,2H); 3,6–3,7 (b,2H); 3,8 (s,2H); 3,9–4,0 (b,2H); 5,1 (s,1H); 5,2 (s,1H); 6,1 (s,1H); 6,2 (d,1H); 7,8 (d,1H)

508 0,9 (t,3H); 1,3 (s,9H); 1,4 (m,2H); 1,7 (m,2H); 1,9 (m,2H); 2,6 (m,4H); 2,7 (t,2H); 3,1 (d,3H); 3,2 (s,2H); 3,3 (s,3H); 3,6 (m,1H); 3,7 (s,2H); 3,6–3,8 (b,4H); 5,0 (d,2H); 6,0 (s,1H)

509 Dihydrochloride 0,9 (t,3H); 1,3 (m,2H); 1,4 (s,9H); 1,7 (m,2H); 2,4–2,5 (b,2H); 2,9 (t,2H); 3,2–3,4 (b,4H); 3,5 (s,3H); 3,7–3,8 (b,2H); 3,9 (s,2H); 3,9–4,2 (b,2H); 4,1 (s,2H); 5,4 (s,2H); 6,9 (s,1H);8,5 (s,2H); 11,7 (b,1H); 14,0 (b,1H)

510 1,3 (s,9H); 2,0–2,1 (b,2H); 2,7 (t,2H); 2,8 (t,2H); 3,3 (s,2H); 3,5–3,8 (b,2H); 3,8 (s,2H) 3,8–4,1 (b,2H); 5,1 (s,1H); 5,2 (s,1H); 6,2 (m,2H); 7,8 (d,1H); 8,2 (d,1H)

511 1,3 (s,18H); 1,6–1,9 (b,4H); 2,4 (b,2H); 2,7 (b,2H); 2,8 (t,2H); 3,2 (s,3H); 3,7 (m,4H); 5,8 (s,1H);

512 1,3 (s,18H); 1,7–1,8 (m,4H); 2,5 (b,2H); 2,7 (b,2H); 3,0 (t,2H); 3,7–3,8 (m,4H); 6,0 (d,1H); 7,8 (d,1H);

513 1,6–2,1 (m,17H); 2,7 (s,2H); 3,1 (s,2H); 3,3–3,6 (b,6H); 3,4 (s,3H); 3,8–3,9 (b,2H); 4,8 (b,2H); 6,0 (b,2H); 6,8 (s,1H);

514 1,6–2,0 (m,17H); 2,5 (s,2H); 2,6 (s,2H); 3,0 (s,2H); 3,5–3,9 (b,6H); 5,0 (d,2H); 6,0 (d,1H) 6,8 (d,1H); 7,8 (d,1H);

515 1,7–2,0 (m,19H); 2,5 (b,2H); 2,7 (s,2H); 3,0 (t,2H); 3,5–3,8 (b,4H); 6,0 (d,1H); 6,8 (d,1LH); 7,8 (d,1H);

517 Dihydrochloride 1,4 (s,9H); 2,4–2,5 (b,2H); 3,3–3,6 (b,4H); 3,5 (s,3H); 3,7–3,8 (b,2H); 3,8–3,9 (b,2H); 3,9–4,2 (b,4H); 5,4 (s,2H); 7,1 (d,1H); 8,3 (d,1H); 8,5 (s,2H); 11,7 (b,1H); 14,5 (b,1H)

518 1,3 (s,9H); 1,8–2,0 (b,2H); 2,6 (t,2H); 2,7 (t,2H); 3,0 (d,3H); 3,2 (s,2H); 3,3 (s,3H); 3,6 (s,2H); 3,6–3,9 (b,5H); 5,0 (d,2H); 6,2 (s,1H); 6,3 (m,2H); 7,8 (m,2H)

519 1,4 (s,9H); 1,9 (m,2H); 2,6 (t,2H); 2,7 (t,2H); 3,0 (d,3H); 3,2 (s,2H); 3,3 (s,3H); 3,7 (s,2H); 3,6–3,9 (b,5H); 5,0 (d,2H); 6,1 (s,1H); 6,3 (m,2H); 7,6 (m,2H)

527 Hydrochloride 1,2–1,5 (b,1OH); 1,5–1,8 (b,4H); 3,1 (m,4H); 3,5 (m,4H); 3,8–4,0 (b,4H); 6,8 (t,1H); 6,9 (b,3H); 7,1 (t,1H); 10,5 (b,1H)

526 Oxalate 1,3 (s,9H); 1,9–2,1 (b,2H); 2,7–3,0 (b,4H); 3,4 (b,2H); 3,6 (s,3H); 3,6–3,8 (b,2H); 3,8 (s,2H); 3,9–4,1 (b,2H); 5,2 (d,2H); 6,2 (m,2H); 6,4 (s,1H); 7,6 (m,3H); 7,7 (m,4H)

528 Oxalate 0,9 (t,3H); 1,3 (s,9H); 1,4 (m,2H); 1,6 (m,2H); 1,9–2,2 (b,4H); 2,5 (m,2H); 3,0–3,2 (b,4H); 3,2–3,4 (b,4H); 3,5–3,7 (b,2H); 3,9–4,1 (b,2H); 6,1 (d,1H); 6,4 (s,1H); 7,8 (d,1H)

529 Dihydrochloride 0,9 (t,3H); 1,3 (m,2H); 1,4 (s,9H); 1,7 (m,2H); 2,2 (b,3H); 3,0 (t,2H); 3,2 (b,5H); 3,5 (s,3H); 3,5–4,2 (b,7H); 4,5–4,7 (b,1H); 7,0 (d,1H); 8,6 (s,2H); 11,7 (b,1H); 14,2 (b,1H)

530 Oxalate 1,3 (s,9H); 1,9–2,1 (b,2H); 2,7–3,0 (b,4H); 2,3–2,4 (b,2H); 2,6–4,1 (b,4H); 3,9 (s,2H); 5,2 (s,1H); 5,3 (s,1H); 6,1 (d,1H); 6,2 (m,2H); 6,4 (s,1H); 7,7 (m,2H); 7,8 (d,1H)

531 1,3 (s,9H); 1,9 (m,2H); 2,6 (t,2H); 2,7 (t,2H); 3,2 (s,2H); 3,3 (s,3H); 3,7 (s,2H); 3,6–3,9 (b,4H); 4,3 (s,2H); 5,0 (d,2H); 6,2 (s,1H); 6,3 (m,2H); 7,8 (m,2H)

533 1,3 (s,9H); 2,1 (m,2H); 2,7 (m,2H); 2,9 (m,2H); 3,3 (s,2H); 3,6–3,8 (b,2H); 3,8 (s,2H); 3,9–4,1 (b,2H); 5,1 (s,1H); 5,2 (s,1H); 6,1 (s,1H); 6,2 (d,1H); 6,3 (m,2H); 7,5 (m,2H); 7,8 (d,1H)

532 1,3 (s,9H); 1,9 (m,2H); 2,6 (t,2H); 2,7 (t,2H); 3,2 (s,2H); 3,3 (s,3H); 3,7 (s,2H); 3,6–3,6 (b,4H); 4,3 (s,2H); 5,0 (s,2H); 6,1 (s,1H); 6,3 (m,2H); 7,6 (m,2H)

539 Hydrochloride 2,2–2,3 (b,2H); 3,0–3,2 (b,2H); 3,5–4,0 (b,8H), 4,2 (s,2H); 5,5 (d,2H); 6,2 (d,1H); 6,9–7,0 (m,3H); 7,0 (t,1H); 7,4 (m,1H); 7,9 (d,1H); 10,9 (b,1H);

540 Hydrochloride 2,4 (b,2H); 3,2 (b,4H); 3,4 (s,3H); 3,5 (.m,2H); 3,7 (b,4H); 4,0 (s,2H); 5,3 (d,2H); 6,8–7,1 (m,4H); 7,2–7,4 (m,3H);

542 1,3 (s,9H); 1,9 (m,2H); 1,9–2,1 (b,2H); 2,6 (m,4H); 2,8 (b,2H); 3,2 (t,2H); 3,5–3,7 (b,2H); 3,9–4,2 (b,2H); 6,2 (d,1H); 6,5 (s,1H); 6,8 (d,1H)

543 1,3 (s,9H); 1,9 (m,2H); 1,9–2,0 (b,2H); 2,6–2,7 (b,4H); 2,8 (b,2H); 3,1 (t,2H); 3,2 (s,3H); 3,5–3,6 (b,2H); 3,9–4,1 (b,2H); 6,5 (s,1H); 10,8 (b,1H)

544 1,3 (s,9H); 1,8–2,0 (b,4H); 2,6 (m,4H); 2,7–2,8 (b,2H); 3,0 (m,5H); 3,3 (s,3H); 3,5–3,6 (b,2H) 3,9–4,1 (b,3H); 6,5 (s,1H)

545 Hydrochloride 1,3 (s,9H); 2,1–2,2 (b,3H); 2,5–2,6 (b,1H); 3,1–3,3 (b,6H); 3,4 (s,3H); 3,4–3,8 (b,4H); 4,0–4,1 (b,1H); 4,6–4,7 (b,1H); 7,0 (s,1H); 8,6 (s,2H); 11,3 (b,1H)

546 1,3 (s,9H); 1,9 (m,2H); 2,1 (m,2H); 2,7 (m,4H); 2,9 (m,2H); 3,2 (t,2H); 3,8–3,9 (b,2H); 3,9–4,0 (b,2H); 6,2 (d,2H); 6,3 (m,2H); 7,8 (m,3H)

547 1,3 (s,9H); 1,9 (m,4H); 2,6 (m,4H); 2,8 (t,2H); 3,1 (t,2H); 3,2 (s,3H); 3,6–4,0 (b,4H); 6,2 (s,1H); 6,3 (m,2H); 7,8 (m,2H); 9,2 (s,1H)

548 1,3 (s,9H); 1,9 (m,4H); 2,6 (t,4H); 2,8 (t,2H); 3,1 (t,2H); 3,3 (s,3H); 3,5–3,9 (b,4H); 4,1 (s,2H); 6,2 (s,1H); 6,3 (m,2H); 7,8 (m,2H)

549 1,4 (s,9H); 1,9 (m,2H); 2,0–2,1 (b,2H); 2,7 (m,4H); 2,9 (m,2H); 3,2 (t,2H); 3,6–3,8 (b,2H); 3,8–4,1 (b,2H); 6,1 (s,1H); 6,2 (d,1H); 6,3 (m,2H); 7,6 (m,2H); 7,8 (d,1H)

550 1,4 (s,9H); 1,9 (m,4H); 2,6 (m,4H); 2,8 (b,2H); 3,1 (t,2H); 3,2 (s,3H); 3,6–4,0 (b,4H); 6,1 (s,1H); 6,3 (m,2H); 7,5 (m,2H); 10,0 (b,1H)

551 1,4 (s,9H); 1,9 (m,4H); 2,6 (m,4H); 2,8 (b,2H); 3,1 (t,2H); 3,4 (s,3H); 3,5–4,0 (b,4H); 4,3 (s,2H); 6,1 (s,1H); 6,3 (m,2H); 7,5 (m,2H)

552 1,3 (s,9H); 2,1 (m,2H); 2,8 (m,2H); 2,9 (m,2H); 3,3 (s,2H); 3,8 (s,2H); 3,9 (t,2H); 4,1 (b,2H); 5,1 (s,1H); 5,2 (s,1H); 6,2 (d,1H); 6,5 (d,1H); 7,8 (d,1H); 8,2 (d,1H)

553 Hydrochloride 1,3 (s,9H); 2,2–2,3 (b,1H); 2,5–2,7 (b,1H); 3,1 (s,3H); 3,0–3,2 (b,2H); 3,5–3,7 (b,3H); 3,8–4,1 (m,6H); 4,4–4,5 (b,1H); 5,4 (d,2H); 6,8 (d,1H); 8,3 (d,1H); 11,2 (b,1H); 11,9 (s,1H)

554 1,3 (s,9H); 1,9 (m,2H); 2,6 (t,2H); 2,7 (t,2H); 3,2 (s,2H); 3,4 (s,3H); 3,7 (s,2H); 3,8 (m,4H); 4,4 (s,2H); 5,0 (s,2H); 6,5 (d,1H); 8,2 (d,1H)

555 1,3 (s,18H); 2,1 (m,2H); 2,8 (t,2H); 3,0 (t,2H); 3,3 (s,2H); 3,8 (s,2H); 3,9 (t,2H); 4,1 (t,2H); 5,1 (s,1H); 5,2 (s,1H); 6,2 (d,1H); 6,5 (s,1H); 7,8 (d,1H)

556 1,3 (s,18H); 1,9 (m,2H); 2,6 (t,2H); 2,7 (t,2H) 3,2 (s,2H); 3,4 (s,3H); 3,6 (s,2H); 3,9 (m,4H); 4,2 (s,2H); 5,0 (s,2H); 6,5 (s,1H)

557 Hydrochloride 1,3 (d,6H); 2,2 (b,1H); 2,6 (b,1H); 3,0 (b,4H)i 3,4 (s,3H); 3,5–3,7 (b,4H); 3,8 (s,2H); 4,1 (s,2H); 5,4 (s,2H); 6,8 (t,1H); 6,9 (s,1H); 8,5 (b,2H); 11,6 (b,1H);

559 Hydrochloride 1,2 (d,6H); 2,1 (b,4H); 3,0–3,2 (b,8H); 3,5–4,2 (b,4H); 6,1 (d,1H); 6,8 (t,1H); 6,9 (b,1H); 7,8 (d,1H); 11,3 (b,1H)

561 1,3 (s,18H); 1,9 (m,2H); 2,0 (m,2H); 2,7 (t,2H); 2,8 (t,2H); 3,0 (t,2H); 3,2 (t,2H); 3,9 (t,2H); 4,0 (t,2H); 6,1 (d,1H); 6,5 (s,1H); 7,8 (d,1H)

562 1,3 (s,18H); 1,9 (m,4H); 2,6 (m,4H); 2,8 (t,2H); 3,0 (t,2H); 3,4 (s,3H); 3,8 (t,2H); 3,9 (t,2H); 4,3 (s,2H); 6,5 (s,1H)

564 Oxalate 1,3 (s,9H); 2,0 (b,2H); 2,2 (b,2H); 3,1–3,4 (b,8H); 3,3 (b,2H); 3,8 (s,3H); 4,0 (b,2H); 6,1 (d,2H); 6,9 (s,1H); 7,0 (d,1H); 7,8 (d,1H); 8,1 (d,1H);

563 Oxalate 1,3 (s,9H); 1,9 (b,2H); 2,2 (b,2H); 2,9 (t,2H); 3,1 (t,2H); 3,3 (b,4H); 3,4 (s,3H); 3,7 (b,2H); 3,8 (s,3H); 4,0 (b,2H); 5,3 (s,2H); 6,8 (s,1H); 6,9 (s,2H); 8,0 (d,1H);

566 1,4 (s,9H); 1,9 (b,2H); 2,5 (b,2H); 2,8 (b,2H); 3,2 (s,2H); 3,3 (s,3H); 3,6 (s,2H); 3,6–3,8 (b,4H); 3,8 (s,3H); 4,8 (b,2H); 5,0 (s,2H); 6,5 (s,1H); 7,0 (d,1H); 8,0 (d,1H);

567 Oxalate 2,0 (b,2H); 2,8 (b,2H); 3,0 (b,2H); 3,3 (s,3H); 3,4 (s,2H); 3,6 (b,4H); 3,8 (b,2H); 5,1 (s,2H); 5,5 (b,2H); 7,0 (m,2H); 7,7 (t,1H);

568 Oxalate 2,0 (b,2H); 2,2 (b,2H); 3,0 (t,2H); 3,1 (m,2H); 3,2 (b,4H); 3,4 (s,3H); 3,6 (m,2H); 3,9 (b,2H); 6,7 (b,2H); 7,0 (t,2H); 7,7 (t,1H);

569 Oxalate 2,0–2,2 (b,4H); 3,0–3,4 (m,8H); 3,5 (m,2H); 3,9 (b,2H); 6,1 (d,1H); 6,5 (b,2H); 7,0 (t,2H); 7,7 (t,1H); 7,8 (d,1H);

570 Hydrochloride 1,3 (s,9H); 2,0–2,2 (b,3H); 2,3–2,4 (b,1H); 3,2 (m,6H); 3,4–4,0 (b,5H); 4,3–4,5 (b,1H); 6,2 (d,1H); 6,8 (d,1H); 7,9 (d,1H); 8,3 (d,1H); 10,8 (b,1H)

571 Hydrochloride 1,3 (s,9H); 2,0–2,2 (b,3H); 2,3–2,4 (b,1H); 3,1 (s,3H); 3,0–3,2 (m,6H); 3,4–4,0 (b,5H); 4,3–4,5 (b,1H); 6,8 (d,1H); 8,3 (d,1H); 10,9 (b,1H); 11,9 (s,1H)

572 1,3 (s,9H); 1,9–2,0 (m,4H); 2,6 (m,4H); 2,8 (t,2H); 3,0 (t,2H); 3,4 (s,3H); 3,8 (t,2H); 3,9 (b,2H); 4,6 (b,2H); 6,5 (d,1H); 8,2 (d,1H)

We claim:

1. A compound of the formula I $$Ar^1-A-B-Ar^2 \qquad (I)$$

where $Ar^1$ is a 6-membered heteroaromatic ring with 1 or 2 heteronitrogen atoms, where $Ar^1$ may have 1, 2, 3 or 4 substituents which are selected, independently of one another, from $OR^1$, alkyl which is unsubstituted or substituted by OH, $OC_1-C_8$-alkyl or halogen, or $C_2-C_6$-alkenyl, $C_2-C_6$-alkynyl, cycloalkyl, halogen, CN, $CO_2R^1$, $NO_2$, $NR^1R^2$, $SR^1$, $CF_3$, $CHF_2$, phenyl which is unsubstituted or substituted by $C_1-C_6$-alkyl, $OC_1-C_6$-alkyl, acyl, phenyl, amino, nitro, cyano or halogen, or phenoxy which is unsubstituted or substituted by $C_1-C_6$-alkyl, $OC_1-C_6$-alkyl or halogen, or $C_1-C_6$-alkanoyl or benzoyl;

$R^1$ is H, alkyl which is unsubstituted or substituted by OH, $OC_1-C_6$-alkyl, phenyl or halogen;

$R^2$ has the meanings stated for $R^1$ or is $COR^1$ or $CO_2R^1$;

A is a $C_4-C_{15}$-alkylene group or a $C_3-C_{15}$-alkylene group which comprises at least one group Z which is selected from O, S, $NR^1$, a double and a triple bond, where $R^1$ is as defined above, B is a 7- or 8-membered saturated ring with two nitrogen heteroatoms, the nitrogen heteroatoms being located in the 1,4 or 1,5 position and the ring being bonded in position 1 to the radical A and in position 4 or 5 to the radical $Ar^2$, and it additionally being possible for the ring to have a double bond in position 3 or 4;

$Ar^2$ is phenyl, pyridyl, or pyrimidinyl, it being possible for $Ar^2$ to have 1, 2, 3 or 4 substituents which are selected, independently of one another, from $OR^1$, alkyl, $C_2-C_6$-alkenyl, $C_2-C_6$-alkynyl, alkoxyalkyl, haloalkyl, halogen, CN, $CO_2 R^1$, $NO_2$, $SO_2 R^1$, $NR^1 R^2$, $SO_2N R^1 R^2$, $SR^1$, a 5- or 6-membered carbocyclic, aromatic or non-aromatic ring and a 5- or 6-membered heterocyclic aromatic or non-aromatic ring with 1 to 3 heteroatoms which are selected from O, S and N. the carbocyclic or heterocyclic ring being unsubstituted or substituted by $C_1-C_8$-alkyl, phenyl, halogen, $OC_1-C_8$-alkyl, OH, $NO_2$ or $CF_3$, and $Ar^2$ may also be fused to a carbocyclic ring of the type defined above, and where $Ar^2$ cannot be a pyrimidinyl radical substituted by 2 hydroxyl groups, and the salts thereof with physiologically tolerated acids.

2. A compound as claimed in claim 1 of the formula I where $Ar^1$ is

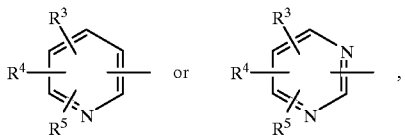

where
$R^3$ to $R^5$ are, independently of one another, H or the substituents mentioned in claim 1 for the radical $Ar^1$.

3. A compound as claimed in claim 1 of the formula I where $Ar^1$ is

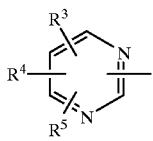

where $R^3$ to $R^5$ have the meanings stated in claim 2.

4. A compound as claimed in claim 3 of the formula I where $R^3$, $R^4$ and $R^5$ are, independently of one another, H, $OR^1$, alkyl, $NR^1R^2$, halogen, phenoxy, CN, phenyl which is unsubstituted or substituted by $C_1$–$C_6$-alkyl, acyl or halogen, or $COOR^1$;
$R^1$ and $R^2$ are, independently of one another, H, alkyl or benzyl.

5. A compound as claimed in claim 4, where $R^3$ to $R^6$ are selected, independently of one another, from H, $C_1$–$C_6$-alkyl, $OR^1$, $NR^1R^2$, phenyl which is unsubstituted or substituted by $C_1$–$C_6$-alkyl, acyl or halogen, and halogen, where $R^1$ and $R^2$ have the abovementioned meanings.

6. A compound as claimed in claim 5, where $Ar^1$ is pyrimidinyl which is unsubstituted or substituted by OH, Oalkyl or Obenzyl.

7. A compound as claimed in any of the preceding claims of the formula I, where A is —Z—$C_3$–$C_6$-alkylene, in particular —Z—$CH_2CH_2CH_2$—, —Z—$CH_2CH_2CH_2CH_2$—, —Z—$CH_2CH$=$CHCH_2$—, —Z—$CH_2C(CH_3)$=$CHCH_2$—, —Z—$CH_2C$(=$CH_2$)$CH_2$—, —Z—$CH_2CH(CH_3)CH_2$— or a linear —Z—$C_7$–$C_{10}$-alkylene radical, where Z is bonded to $Ar^1$ and is $CH_2$, O or S.

8. A compound as claimed in claim 1 of the formula I, where B is

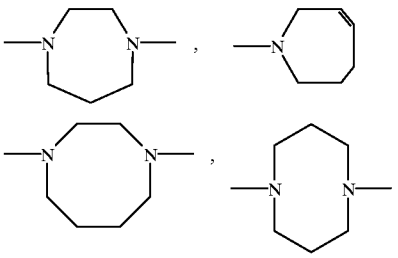

9. A compound as claimed in claim 1 of the formula I, where $Ar^2$ is phenyl, pyridinyl or pyrimidinyl, which may have one or two substituents which are selected, independently of one another, from $C_1$–$C_6$-alkyl, $C_2$–$C_6$-alkynyl, halogen, CN, haloalkyl, Oalkyl, $NO_2$, phenyl, pyrrolyl, imidazolyl, pyrazolyl, thienyl, cyclopentyl and cyclohexyl.

10. A compound as claimed in claim 9 of the formula I, where the substituent(s) are selected, independently of one another, from $C_1$–$C_6$-alkyl, $NO_2$ and haloalkyl, in particular $CF_3$, $CHF_2$ and $CF_2Cl$.

11. A pharmaceutical composition comprising at least one compound as claimed in any of claim 1, with or without physiologically acceptable vehicles and/or ancillary substances.

12. A method for treating a disorder which responds to dopamine $D_3$ receptor antagonists or agonists which comprises treating the disorder with a compound of claim 1.

* * * * *